United States Patent
Leigh et al.

(10) Patent No.: US 11,918,808 B2
(45) Date of Patent: Mar. 5, 2024

(54) MAGNET MANAGEMENT MRI COMPATIBILITY

(71) Applicants: Charles Roger Aaron Leigh, Macquarie University (AU); Grahame Michael David Walling, Macquarie University (AU); Mark Alan Von Huben, Macquarie University (AU); James Vandyke, Macquarie University (AU); Nam Long Tuong, Sadleir (AU)

(72) Inventors: Charles Roger Aaron Leigh, Macquarie University (AU); Grahame Michael David Walling, Macquarie University (AU); Mark Alan Von Huben, Macquarie University (AU); James Vandyke, Macquarie University (AU); Nam Long Tuong, Sadleir (AU)

(73) Assignee: Cochlear Limited, Macquarie University (AU)

(*) Notice: Subject to any disclaimer, the term of this patent is extended or adjusted under 35 U.S.C. 154(b) by 0 days.

(21) Appl. No.: 18/072,770

(22) Filed: Dec. 1, 2022

(65) Prior Publication Data

US 2023/0089429 A1 Mar. 23, 2023

Related U.S. Application Data

(63) Continuation of application No. 17/509,842, filed on Oct. 25, 2021, which is a continuation of application No. 16/195,655, filed on Nov. 19, 2018, now Pat. No. 11,154,711, which is a continuation of application No. 15/010,410, filed on Jan. 29, 2016, now Pat. No. 10,130,807.

(60) Provisional application No. 62/174,788, filed on Jun. 12, 2015.

(51) Int. Cl.
*A61N 1/08* (2006.01)
*A61F 11/00* (2022.01)
(Continued)

(52) U.S. Cl.
CPC ..... *A61N 1/36038* (2017.08); *A61N 1/37518* (2017.08); *A61N 1/0541* (2013.01); *A61N 1/3718* (2013.01)

(58) Field of Classification Search
CPC ...... A61N 1/0541; A61N 1/3718; A61N 1/08; A61N 1/375; A61N 1/36036
See application file for complete search history.

(56) References Cited

U.S. PATENT DOCUMENTS 3,043,000 A 7/1962 Hatfield
3,487,403 A 12/1969 Pihl
(Continued)

FOREIGN PATENT DOCUMENTS

AU 2009101370 A4 3/2013
CN 2411869 Y 12/2000
(Continued)

OTHER PUBLICATIONS

Med-El, "FDA Hands MED-EL Approval for MRI Compatible Cochlear Implant (Video)," believed to be available in Jan. 2015.
(Continued)

*Primary Examiner* — Christine H Matthews
*Assistant Examiner* — Joshua D Lannu
(74) *Attorney, Agent, or Firm* — Pilloff Passino & Cosenza LLP; Martin J. Cosenza

(57) ABSTRACT

An implantable medical device, including a magnet and a body encompassing the magnet, wherein the implantable medical device includes structural components in the body configured to move away from one another upon initial rotation of the magnet relative to the body when the magnet is subjected to an externally generated magnetic field, thereby limiting rotation of the magnet beyond the initial rotation.

30 Claims, 57 Drawing Sheets

(51) Int. Cl.
  *A61N 1/36* (2006.01)
  *A61N 1/375* (2006.01)
  *A61N 5/06* (2006.01)
  *A61N 1/05* (2006.01)
  *A61N 1/37* (2006.01)

(56) References Cited

U.S. PATENT DOCUMENTS

| | | |
|---|---|---|
| 3,573,812 A | 4/1971 | Pihl |
| D227,118 S | 6/1973 | Muraoka |
| 3,771,685 A | 11/1973 | Micallef |
| 3,801,767 A | 4/1974 | Marks |
| 3,987,967 A | 10/1976 | Kuznetsov et al. |
| 4,003,521 A | 1/1977 | Hess |
| 4,038,990 A | 8/1977 | Thompson |
| 4,197,840 A | 4/1980 | Beck et al. |
| 4,199,741 A | 4/1980 | Paulet |
| 4,226,164 A | 10/1980 | Carter |
| 4,240,428 A | 12/1980 | Akhavi |
| 4,257,936 A | 3/1981 | Matsumoto et al. |
| 4,317,969 A | 3/1982 | Riegler et al. |
| 4,352,960 A | 10/1982 | Dormer et al. |
| D267,541 S | 1/1983 | Kanemitsu |
| 4,414,701 A | 11/1983 | Johnson |
| 4,596,971 A | 6/1986 | Hirabayashi et al. |
| 4,606,329 A | 8/1986 | Hough |
| 4,610,621 A | 9/1986 | Taber et al. |
| 4,628,907 A | 12/1986 | Epley |
| 4,634,191 A | 1/1987 | Studer |
| 4,676,772 A | 6/1987 | Hooven |
| 4,726,378 A | 2/1988 | Kaplan |
| 4,731,718 A | 3/1988 | Sheu |
| 4,736,747 A | 4/1988 | Drake |
| 4,743,264 A | 5/1988 | Sherva-Parker |
| 4,792,368 A | 12/1988 | Sagawa et al. |
| 4,817,607 A | 4/1989 | Tatge |
| RE32,947 E | 6/1989 | Dormer et al. |
| 4,868,530 A | 9/1989 | Ahs |
| 4,917,504 A | 4/1990 | Scott et al. |
| 4,918,745 A | 4/1990 | Hutchison |
| 4,920,679 A | 5/1990 | Sarles et al. |
| 5,014,592 A | 5/1991 | Zweig et al. |
| 5,015,224 A | 5/1991 | Maniglia |
| 5,096,763 A | 3/1992 | Ogata et al. |
| 5,105,811 A | 4/1992 | Kuzma |
| 5,183,056 A | 2/1993 | Dalen et al. |
| 5,196,710 A | 3/1993 | Kalfaian |
| 5,282,858 A | 2/1994 | Bisch et al. |
| 5,314,453 A | 5/1994 | Jeutter |
| D348,067 S | 6/1994 | Lucey et al. |
| 5,338,287 A | 8/1994 | Miller et al. |
| 5,360,388 A | 11/1994 | Spindel et al. |
| 5,423,317 A | 6/1995 | Ijima et al. |
| 5,456,654 A | 10/1995 | Ball |
| 5,554,096 A | 9/1996 | Ball |
| 5,603,726 A | 2/1997 | Schulman et al. |
| 5,624,376 A | 4/1997 | Ball et al. |
| 5,630,835 A | 5/1997 | Brownlee |
| 5,716,407 A | 2/1998 | Knapp et al. |
| 5,746,897 A | 5/1998 | Heimanson et al. |
| 5,749,912 A | 5/1998 | Zhang et al. |
| 5,757,183 A | 5/1998 | Smith et al. |
| 5,775,652 A | 7/1998 | Crawshaw et al. |
| 5,785,477 A | 7/1998 | McGuffey et al. |
| 5,800,336 A | 9/1998 | Ball et al. |
| 5,857,958 A | 1/1999 | Ball et al. |
| 5,877,664 A | 3/1999 | Jackson, Jr. |
| 5,897,486 A | 4/1999 | Ball et al. |
| 5,913,815 A | 6/1999 | Ball et al. |
| 5,945,762 A | 8/1999 | Chen et al. |
| 5,965,282 A | 10/1999 | Baermann |
| 5,971,334 A | 10/1999 | Crawshaw et al. |
| 6,040,762 A | 3/2000 | Tompkins |
| 6,073,973 A | 6/2000 | Boscaljon et al. |
| 6,101,417 A | 8/2000 | Vogel et al. |
| 6,138,681 A | 10/2000 | Chen et al. |
| 6,157,278 A | 12/2000 | Katznelson et al. |
| 6,157,281 A | 12/2000 | Katznelson et al. |
| 6,175,767 B1 | 1/2001 | Doyle, Sr. |
| 6,178,079 B1 | 1/2001 | Renger |
| 6,178,353 B1 | 1/2001 | Griffith et al. |
| 6,190,305 B1 | 2/2001 | Ball et al. |
| 6,208,235 B1 | 3/2001 | Trontelj |
| 6,208,882 B1 | 3/2001 | Lenarz et al. |
| 6,217,508 B1 | 4/2001 | Ball et al. |
| 6,219,580 B1 | 4/2001 | Faltys et al. |
| 6,244,142 B1 | 6/2001 | Swanson |
| 6,259,951 B1 | 7/2001 | Kuzma et al. |
| 6,263,230 B1 | 7/2001 | Haynor et al. |
| 6,272,382 B1 | 8/2001 | Faltys et al. |
| 6,292,678 B1 | 9/2001 | Hall et al. |
| 6,295,472 B1 | 9/2001 | Rubinstein et al. |
| 6,295,473 B1 | 9/2001 | Rosar |
| 6,308,101 B1 | 10/2001 | Altys et al. |
| 6,313,551 B1 | 11/2001 | Hazelton |
| 6,348,070 B1 | 2/2002 | Teissl et al. |
| 6,355,998 B1 | 3/2002 | Schöb et al. |
| 6,358,281 B1 | 3/2002 | Berrang et al. |
| 6,401,723 B1 | 6/2002 | Garibaldi et al. |
| 6,475,134 B1 | 11/2002 | Ball et al. |
| 6,505,062 B1 | 1/2003 | Ritter et al. |
| 6,506,987 B1 | 1/2003 | Woods |
| 6,522,909 B1 | 2/2003 | Garibaldi et al. |
| 6,542,777 B1 | 4/2003 | Griffith et al. |
| 6,571,676 B1 | 6/2003 | Folsom et al. |
| 6,643,378 B2 | 11/2003 | Schumaier |
| 6,668,065 B2 | 12/2003 | Lee et al. |
| 6,838,963 B2 | 1/2005 | Zimmerling et al. |
| 6,857,612 B2 | 2/2005 | Goodbred |
| D512,416 S | 12/2005 | Malaver |
| 6,991,594 B2 | 1/2006 | Holcomb |
| 7,038,565 B1 | 5/2006 | Chell |
| 7,091,806 B2 | 8/2006 | Zimmerling et al. |
| 7,190,247 B2 | 3/2007 | Zimmerling |
| 7,191,007 B2 | 3/2007 | Desai et al. |
| 7,200,504 B1 | 4/2007 | Fister |
| 7,225,028 B2 | 5/2007 | Della Santina et al. |
| 7,231,252 B2 | 6/2007 | Duncan et al. |
| 7,266,208 B2 | 9/2007 | Charvin et al. |
| 7,338,028 B2 | 3/2008 | Zimmerling et al. |
| 7,386,143 B2 | 6/2008 | Easter et al. |
| 7,532,937 B2 | 5/2009 | Horio et al. |
| 7,566,296 B2 | 7/2009 | Zimmerling et al. |
| 7,610,096 B2 | 10/2009 | McDonald, III |
| 7,642,887 B2 | 1/2010 | Zimmerling |
| 7,647,120 B2 | 1/2010 | Della Santina et al. |
| 7,695,427 B2 | 4/2010 | Kugler et al. |
| 7,762,998 B2 | 7/2010 | Birk et al. |
| 7,808,348 B2 | 10/2010 | Fullerton et al. |
| 7,856,986 B2 | 12/2010 | Darley |
| 7,976,453 B2 | 7/2011 | Zimmerling et al. |
| 7,991,477 B2 | 8/2011 | McDonald, III |
| 8,013,699 B2 | 9/2011 | Zimmerling |
| 8,118,725 B2 | 2/2012 | Zimmerling et al. |
| 8,211,174 B2 | 7/2012 | Park et al. |
| 8,246,533 B2 | 8/2012 | Chang et al. |
| 8,255,058 B2 | 8/2012 | Gibson et al. |
| 8,260,435 B2 | 9/2012 | Johnson et al. |
| 8,270,647 B2 | 9/2012 | Crawford et al. |
| 8,340,774 B2 | 12/2012 | Hochmair et al. |
| 8,400,038 B2 | 3/2013 | Smith et al. |
| 8,406,443 B2 | 3/2013 | Westerkull et al. |
| 8,515,112 B2 | 8/2013 | Crawford et al. |
| 8,515,544 B2 | 8/2013 | Daly et al. |
| 8,532,783 B2 | 9/2013 | Zimmerling et al. |
| 8,634,909 B2 | 1/2014 | Zimmerling et al. |
| 8,734,475 B2 | 5/2014 | Ekvall et al. |
| 8,744,106 B2 | 6/2014 | Ball |
| 8,758,394 B2 | 6/2014 | Zimmerling et al. |
| 8,768,480 B2 | 7/2014 | Charvin |
| 8,811,643 B2 | 8/2014 | Crawford et al. |
| 8,829,462 B2 | 9/2014 | Clarke et al. |
| 8,829,752 B2 | 9/2014 | Chen et al. |
| 8,897,475 B2 | 11/2014 | Ball et al. |

(56) References Cited

U.S. PATENT DOCUMENTS

| | | |
|---|---|---|
| 8,983,102 B2 | 3/2015 | Crawford et al. |
| 8,987,951 B2 | 3/2015 | Park |
| 9,002,469 B2 | 4/2015 | D'Ambrosio |
| 9,014,782 B2 | 4/2015 | Miyoshi |
| 9,022,917 B2 | 5/2015 | Kasic et al. |
| 9,042,995 B2 | 5/2015 | Dinsmoor et al. |
| 9,058,962 B2 | 6/2015 | Endo et al. |
| 9,113,268 B2 | 8/2015 | Ball et al. |
| RE45,701 E | 9/2015 | Zimmerling et al. |
| 9,136,728 B2 | 9/2015 | Dinsmoor et al. |
| 9,144,676 B2 | 9/2015 | Gibson et al. |
| 9,179,228 B2 | 11/2015 | Ruppersberg et al. |
| 9,210,521 B2 | 12/2015 | Kasic et al. |
| 9,258,656 B2 | 2/2016 | Ruppersberg et al. |
| 9,392,384 B2 | 7/2016 | Crawford et al. |
| 9,420,388 B2 | 8/2016 | Ball |
| 9,526,810 B2 | 12/2016 | Ruppersberg |
| 9,627,120 B2 | 4/2017 | Scott et al. |
| 9,736,601 B2 | 8/2017 | Kasic et al. |
| 9,739,842 B2 | 8/2017 | Holm et al. |
| 9,788,125 B2 | 10/2017 | Ruppersberg et al. |
| RE46,624 E | 12/2017 | Zimmerling et al. |
| 9,872,115 B2 | 1/2018 | Kennes |
| 9,872,993 B2 | 1/2018 | Zimmerling |
| 10,130,807 B2 | 11/2018 | Eigh et al. |
| 10,186,360 B2 | 1/2019 | Shimbo et al. |
| 10,405,891 B2 | 9/2019 | Pool et al. |
| 10,646,712 B2 | 5/2020 | Smith et al. |
| 10,917,730 B2 | 2/2021 | Kennes et al. |
| 10,942,042 B2 | 3/2021 | Bidaux et al. |
| 11,012,796 B2 | 5/2021 | Andersson et al. |
| 11,097,095 B2 | 8/2021 | Smith et al. |
| 2001/0021805 A1 | 9/2001 | Blume et al. |
| 2002/0076071 A1 | 6/2002 | Single |
| 2002/0103430 A1 | 8/2002 | Hastings |
| 2002/0116033 A1 | 8/2002 | Greatbatch et al. |
| 2002/0116034 A1 | 8/2002 | Miller et al. |
| 2002/0120332 A1 | 8/2002 | Law et al. |
| 2003/0034039 A1 | 2/2003 | Schmid et al. |
| 2003/0034705 A1 | 2/2003 | Hakansson |
| 2003/0089933 A1 | 5/2003 | Janesky et al. |
| 2003/0120202 A1 | 6/2003 | Gordon |
| 2003/0139782 A1 | 7/2003 | Duncan |
| 2003/0161481 A1 | 8/2003 | Miller et al. |
| 2003/0161482 A1 | 8/2003 | Miller et al. |
| 2003/0163021 A1 | 8/2003 | Miller et al. |
| 2003/0163022 A1 | 8/2003 | Miller et al. |
| 2003/0171787 A1 | 9/2003 | Money et al. |
| 2003/0171792 A1 | 9/2003 | Zarinetchi et al. |
| 2003/0181956 A1 | 9/2003 | Duncan et al. |
| 2004/0012470 A1 | 1/2004 | Zimmerling et al. |
| 2004/0032962 A1 | 2/2004 | Westerkull |
| 2004/0059423 A1 | 3/2004 | Barnes et al. |
| 2004/0136558 A1 | 7/2004 | Usuki et al. |
| 2004/0147804 A1 | 7/2004 | Schneider et al. |
| 2004/0148025 A1 | 7/2004 | Schneider et al. |
| 2004/0260361 A1 | 12/2004 | Gibson |
| 2004/0260362 A1 | 12/2004 | Darley |
| 2005/0001703 A1 | 1/2005 | Zimmerling |
| 2005/0004629 A1 | 1/2005 | Gibson et al. |
| 2005/0062567 A1 | 3/2005 | Zimmerling et al. |
| 2005/0070346 A1 | 3/2005 | Pan |
| 2005/0101830 A1 | 5/2005 | Aster et al. |
| 2005/0159791 A1 | 7/2005 | Daly et al. |
| 2005/0165471 A1 | 7/2005 | Wang et al. |
| 2005/0171579 A1 | 8/2005 | Tasche et al. |
| 2005/0197715 A1 | 9/2005 | Kugler et al. |
| 2005/0216075 A1 | 9/2005 | Wang et al. |
| 2005/0228214 A1 | 10/2005 | Schneider et al. |
| 2005/0228215 A1 | 10/2005 | Schneider et al. |
| 2005/0240098 A1 | 10/2005 | Zhong et al. |
| 2006/0030905 A1 | 2/2006 | Malaver |
| 2006/0045298 A1 | 3/2006 | Westerkull |
| 2006/0056649 A1 | 3/2006 | Schumaier |
| 2006/0084857 A1 | 4/2006 | Massengill et al. |
| 2006/0119356 A1 | 6/2006 | Rabe et al. |
| 2006/0184212 A1 | 8/2006 | Faltys et al. |
| 2006/0217792 A1 | 9/2006 | Hussein et al. |
| 2006/0241746 A1 | 10/2006 | Shaoulian et al. |
| 2006/0244560 A1 | 11/2006 | Zimmerling et al. |
| 2006/0247488 A1 | 11/2006 | Waldmann |
| 2007/0053536 A1 | 3/2007 | Westerkull |
| 2007/0083078 A1 | 4/2007 | Easter et al. |
| 2007/0100197 A1 | 5/2007 | Perkins et al. |
| 2007/0126540 A1 | 6/2007 | Zimmerling |
| 2007/0170533 A1 | 7/2007 | Doogue et al. |
| 2007/0179333 A1 | 8/2007 | Bove |
| 2007/0208403 A1 | 9/2007 | Della Santina et al. |
| 2008/0009920 A1* | 1/2008 | Gibson ................ A61N 1/3787 607/57 |
| 2008/0044049 A1 | 2/2008 | Ho et al. |
| 2008/0071353 A1 | 3/2008 | Weber et al. |
| 2008/0221641 A1 | 9/2008 | Hochmair |
| 2008/0293998 A1 | 11/2008 | Andrews |
| 2008/0304686 A1 | 12/2008 | Meskens et al. |
| 2009/0030529 A1 | 1/2009 | Berrang et al. |
| 2009/0043149 A1 | 2/2009 | Abel |
| 2009/0069869 A1 | 3/2009 | Stouffer et al. |
| 2009/0138062 A1 | 5/2009 | Balslev |
| 2009/0237080 A1 | 9/2009 | Kato et al. |
| 2009/0248155 A1 | 10/2009 | Parker |
| 2009/0251264 A1 | 10/2009 | Fullerton et al. |
| 2009/0281367 A1 | 11/2009 | Cho et al. |
| 2009/0287036 A1 | 11/2009 | Shapiro et al. |
| 2009/0287278 A1 | 11/2009 | Charvin |
| 2009/0295521 A1 | 12/2009 | Fullerton et al. |
| 2010/0145135 A1 | 6/2010 | Ball et al. |
| 2010/0219712 A1 | 9/2010 | Kogure et al. |
| 2010/0237969 A1 | 9/2010 | Crawshaw |
| 2010/0272299 A1 | 10/2010 | Van Schuylenbergh et al. |
| 2010/0292759 A1 | 11/2010 | Hahn et al. |
| 2011/0004278 A1 | 1/2011 | Aghassian |
| 2011/0022120 A1 | 1/2011 | Ball et al. |
| 2011/0031839 A1 | 2/2011 | Fullerton et al. |
| 2011/0054237 A1 | 3/2011 | Shapiro et al. |
| 2011/0077502 A1 | 3/2011 | Rofougaran |
| 2011/0106210 A1 | 5/2011 | Meskens |
| 2011/0112607 A1 | 5/2011 | Zierhofer |
| 2011/0130622 A1 | 6/2011 | Ilberg |
| 2011/0152603 A1 | 6/2011 | Perkins et al. |
| 2011/0224789 A1 | 9/2011 | Griffith |
| 2011/0264172 A1* | 10/2011 | Zimmerling ....... A61N 1/36036 607/60 |
| 2011/0268303 A1 | 11/2011 | Ahsani |
| 2011/0285488 A1 | 11/2011 | Scott et al. |
| 2011/0291507 A1 | 12/2011 | Post |
| 2011/0295053 A1 | 12/2011 | Ball |
| 2012/0022616 A1 | 1/2012 | Garnham et al. |
| 2012/0022647 A1 | 1/2012 | Leigh et al. |
| 2012/0029267 A1 | 2/2012 | Ball |
| 2012/0062992 A1 | 3/2012 | Kimoto |
| 2012/0078035 A1 | 3/2012 | Andersson et al. |
| 2012/0080039 A1 | 4/2012 | Siegert |
| 2012/0088956 A1 | 4/2012 | Asnes et al. |
| 2012/0095283 A1 | 4/2012 | Andersson et al. |
| 2012/0104875 A1 | 5/2012 | Park |
| 2012/0108887 A1 | 5/2012 | Vermeiren |
| 2012/0172659 A1 | 7/2012 | Ball et al. |
| 2012/0237067 A1 | 9/2012 | Asnes |
| 2012/0238799 A1 | 9/2012 | Ball et al. |
| 2012/0256715 A1 | 10/2012 | Fullerton et al. |
| 2012/0262019 A1 | 10/2012 | Smith et al. |
| 2012/0262020 A1 | 10/2012 | Smith et al. |
| 2012/0284969 A1 | 11/2012 | Fullerton et al. |
| 2012/0296155 A1 | 11/2012 | Ball |
| 2012/0313473 A1 | 12/2012 | Chen et al. |
| 2012/0319809 A1 | 12/2012 | Fullerton |
| 2012/0323066 A1 | 12/2012 | Cho et al. |
| 2012/0330378 A1 | 12/2012 | Crawford et al. |
| 2013/0004003 A1 | 1/2013 | Tada |
| 2013/0006044 A1 | 1/2013 | Menzl |
| 2013/0018218 A1 | 1/2013 | Haller et al. |
| 2013/0023954 A1 | 1/2013 | Meskens |
| 2013/0046131 A1 | 2/2013 | Ball et al. |

(56) References Cited

U.S. PATENT DOCUMENTS

| | | |
|---|---|---|
| 2013/0046360 A1 | 2/2013 | Gibson et al. |
| 2013/0053874 A1 | 2/2013 | Ekvall et al. |
| 2013/0096366 A1 | 4/2013 | Bervoets et al. |
| 2013/0099703 A1 | 4/2013 | Epstein et al. |
| 2013/0110198 A1 | 5/2013 | Stoffaneller |
| 2013/0114834 A1 | 5/2013 | Bern |
| 2013/0165738 A1 | 6/2013 | Ball et al. |
| 2013/0190552 A1 | 7/2013 | Leblans |
| 2013/0195304 A1 | 8/2013 | Andersson |
| 2013/0199031 A1 | 8/2013 | Fullerton et al. |
| 2013/0202140 A1 | 8/2013 | Asnes |
| 2013/0207760 A1 | 8/2013 | Clarke et al. |
| 2013/0214631 A1 | 8/2013 | Smith et al. |
| 2013/0261701 A1 | 10/2013 | Kuratle et al. |
| 2013/0268012 A1 | 10/2013 | Sison |
| 2013/0278254 A1 | 10/2013 | Reeder et al. |
| 2013/0281764 A1 | 10/2013 | Björn et al. |
| 2013/0289384 A1 | 10/2013 | Jenison et al. |
| 2013/0305522 A1 | 11/2013 | Fullerton et al. |
| 2014/0005522 A1 | 1/2014 | Zurovcik |
| 2014/0012069 A1 | 1/2014 | Ball |
| 2014/0012070 A1 | 1/2014 | Nagl et al. |
| 2014/0012071 A1 | 1/2014 | Nagl et al. |
| 2014/0012349 A1 | 1/2014 | Zimmerling |
| 2014/0064531 A1 | 3/2014 | Andersson et al. |
| 2014/0094876 A1 | 4/2014 | Wingeier et al. |
| 2014/0121447 A1 | 5/2014 | Kasic et al. |
| 2014/0121450 A1 | 5/2014 | Kasic et al. |
| 2014/0121451 A1 | 5/2014 | Kasic et al. |
| 2014/0163308 A1 | 6/2014 | Miller et al. |
| 2014/0163309 A1 | 6/2014 | Bernhard et al. |
| 2014/0213139 A1 | 7/2014 | Ferguson |
| 2014/0242140 A1 | 8/2014 | Neu et al. |
| 2014/0257081 A1 | 9/2014 | Rapoport |
| 2014/0270297 A1 | 9/2014 | Gustafsson et al. |
| 2014/0275731 A1 | 9/2014 | Andersson et al. |
| 2014/0275736 A1 | 9/2014 | Ruppersberg et al. |
| 2014/0292321 A1 | 10/2014 | Yamazaki et al. |
| 2014/0293073 A1 | 10/2014 | Okamura et al. |
| 2014/0300437 A1 | 10/2014 | Fullerton et al. |
| 2014/0302741 A1 | 10/2014 | Whittaker |
| 2014/0321681 A1 | 10/2014 | Ball et al. |
| 2014/0336447 A1 | 11/2014 | Björn et al. |
| 2014/0343626 A1 | 11/2014 | Thenuwara et al. |
| 2014/0364681 A1 | 12/2014 | Hillbratt et al. |
| 2014/0364682 A1 | 12/2014 | Hillbratt et al. |
| 2014/0364922 A1 | 12/2014 | Garham et al. |
| 2014/0375829 A1 | 12/2014 | Nishihara et al. |
| 2014/0379103 A1 | 12/2014 | Shikawa et al. |
| 2015/0022298 A1 | 1/2015 | Fullerton |
| 2015/0032186 A1 | 1/2015 | Cushing et al. |
| 2015/0045607 A1 | 2/2015 | Håkansson |
| 2015/0045855 A1 | 2/2015 | Griffith |
| 2015/0087892 A1 | 3/2015 | Tourrel et al. |
| 2015/0092969 A1 | 4/2015 | Meskens et al. |
| 2015/0104052 A1 | 4/2015 | Gustafsson et al. |
| 2015/0117689 A1 | 4/2015 | Bergs et al. |
| 2015/0156595 A1 | 6/2015 | Zhong et al. |
| 2015/0157778 A1 | 6/2015 | Ishiyama et al. |
| 2015/0160426 A1 | 6/2015 | Chao et al. |
| 2015/0160470 A1 | 6/2015 | Terajima |
| 2015/0173468 A1 | 6/2015 | Stevenson |
| 2015/0192432 A1 | 7/2015 | Noguchi et al. |
| 2015/0201290 A1 | 7/2015 | Nikles et al. |
| 2015/0215708 A1 | 7/2015 | Meskens et al. |
| 2015/0265842 A1 | 9/2015 | Ridler et al. |
| 2015/0281860 A1 | 10/2015 | Johansson et al. |
| 2015/0312686 A1 | 10/2015 | Gustafsson et al. |
| 2015/0382114 A1 | 12/2015 | Andersson et al. |
| 2016/0021470 A1 | 1/2016 | Gustafsson |
| 2016/0037273 A1 | 2/2016 | Gustafsson |
| 2016/0058555 A1 | 3/2016 | Andersson et al. |
| 2016/0084920 A1 | 3/2016 | Liu et al. |
| 2016/0100260 A1 | 4/2016 | Ruppersberg et al. |
| 2016/0112813 A1 | 4/2016 | Hillbratt et al. |
| 2016/0161288 A1 | 6/2016 | Lu |
| 2016/0198270 A9 | 7/2016 | Nagl et al. |
| 2016/0205484 A1 | 7/2016 | Nagl et al. |
| 2016/0234613 A1 | 8/2016 | Westerkull |
| 2016/0247616 A1 | 8/2016 | Smith et al. |
| 2016/0361537 A1 | 12/2016 | Leigh et al. |
| 2016/0381473 A1 | 12/2016 | Gustafsson |
| 2016/0381474 A1 | 12/2016 | Gustafsson et al. |
| 2017/0078808 A1 | 3/2017 | Kennes |
| 2017/0111728 A1 | 4/2017 | Kim et al. |
| 2017/0162311 A1 | 6/2017 | Shmbo et al. |
| 2017/0162367 A1 | 6/2017 | Yokota et al. |
| 2017/0216523 A1 | 8/2017 | Neftel et al. |
| 2017/0251313 A1 | 8/2017 | Gustafsson |
| 2018/0160241 A1 | 6/2018 | Gustafsson et al. |
| 2018/0252228 A1 | 9/2018 | Henseler et al. |
| 2018/0270591 A1 | 9/2018 | Kennes |
| 2018/0288538 A1 | 10/2018 | Andersson et al. |
| 2018/0352349 A1 | 12/2018 | Fung et al. |
| 2018/0369586 A1 | 12/2018 | Lee et al. |
| 2019/0046797 A1 | 2/2019 | Calixto et al. |
| 2019/0076649 A1 | 3/2019 | Lee et al. |
| 2019/0151653 A1 | 5/2019 | Leigh et al. |
| 2019/0215623 A1 | 7/2019 | Bodvarsson |
| 2019/0239007 A1 | 8/2019 | Kennes et al. |
| 2019/0293454 A1 | 9/2019 | Bidaux et al. |
| 2020/0114151 A1 | 4/2020 | Smith et al. |
| 2020/0197702 A1 | 6/2020 | Eigentler |
| 2021/0046318 A1 | 2/2021 | Gibson et al. |
| 2021/0106815 A1 | 4/2021 | Smith et al. |
| 2021/0235209 A1 | 7/2021 | Kennes et al. |
| 2021/0257139 A1 | 8/2021 | Nellessen |
| 2021/0316136 A1 | 10/2021 | Smith et al. |
| 2022/0072302 A1 | 3/2022 | Zimmerling |

FOREIGN PATENT DOCUMENTS

| | | |
|---|---|---|
| EP | 2720480 A2 | 4/2014 |
| EP | 3307383 B1 | 3/2020 |
| GB | 414579 A | 8/1934 |
| GB | 2196855 A | 5/1988 |
| GB | 2205999 A | 12/1988 |
| GB | 2266045 A | 10/1993 |
| JP | 2010075394 A | 4/2010 |
| JP | 2012191448 A | 10/2012 |
| JP | 2013232860 A | 11/2013 |
| KR | 101743793 A | 5/2013 |
| KR | 101297828 B1 | 8/2013 |
| KR | 101537380 B1 | 7/2015 |
| WO | 9716835 A1 | 5/1997 |
| WO | 9939769 A1 | 8/1999 |
| WO | 2007024657 A1 | 3/2007 |
| WO | 2014008169 A1 | 1/2014 |
| WO | 2014011582 A2 | 1/2014 |
| WO | 2015065442 A2 | 5/2015 |
| WO | 2016207856 A1 | 12/2016 |
| WO | 2016207860 A1 | 12/2016 |
| WO | 2017046650 A1 | 3/2017 |
| WO | 2017105510 A1 | 6/2017 |
| WO | 2017105511 A1 | 6/2017 |
| WO | 2018200347 A1 | 11/2018 |
| WO | 2021059163 A1 | 4/2021 |

OTHER PUBLICATIONS

Daniel Rutter, "Comparison: Lightwave 2000, 3000, 4000, Illuminator and Pocket-Bright, and Petzl Tikka" pp. 1-30, Feb. 14, 2002. http://www.dansdata.com/ledlights7.htm.

* cited by examiner

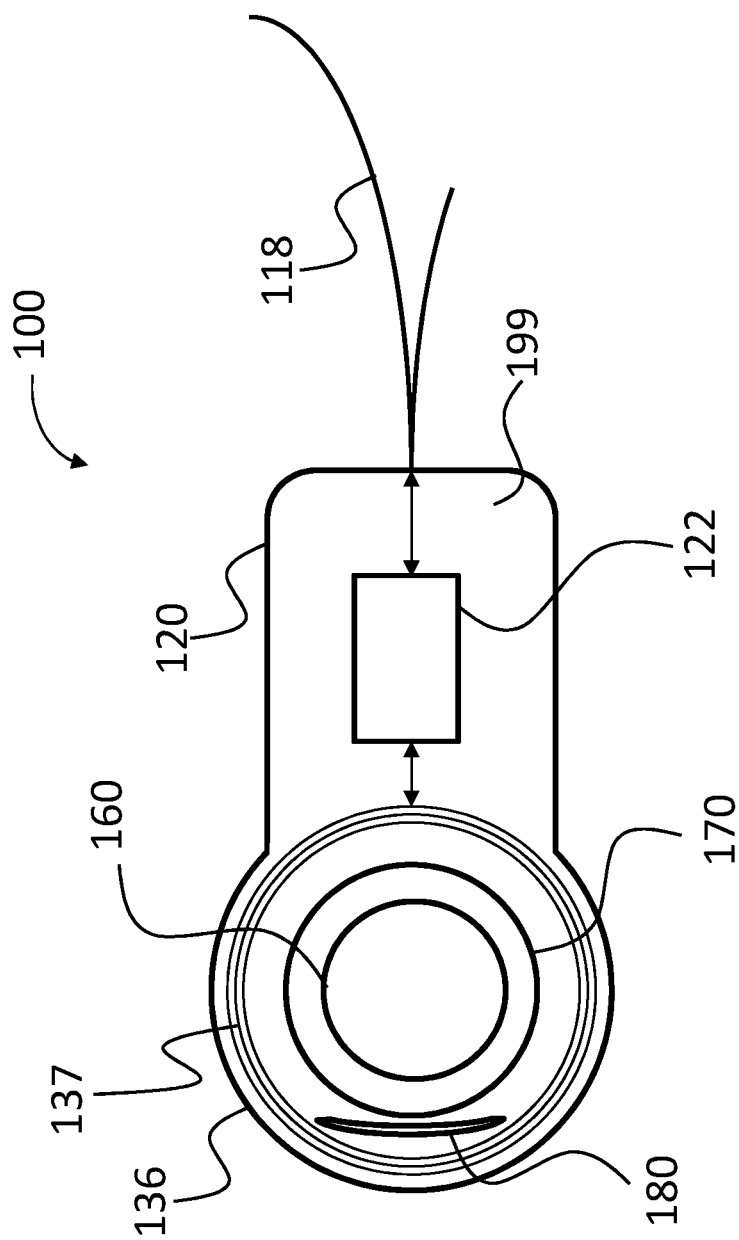

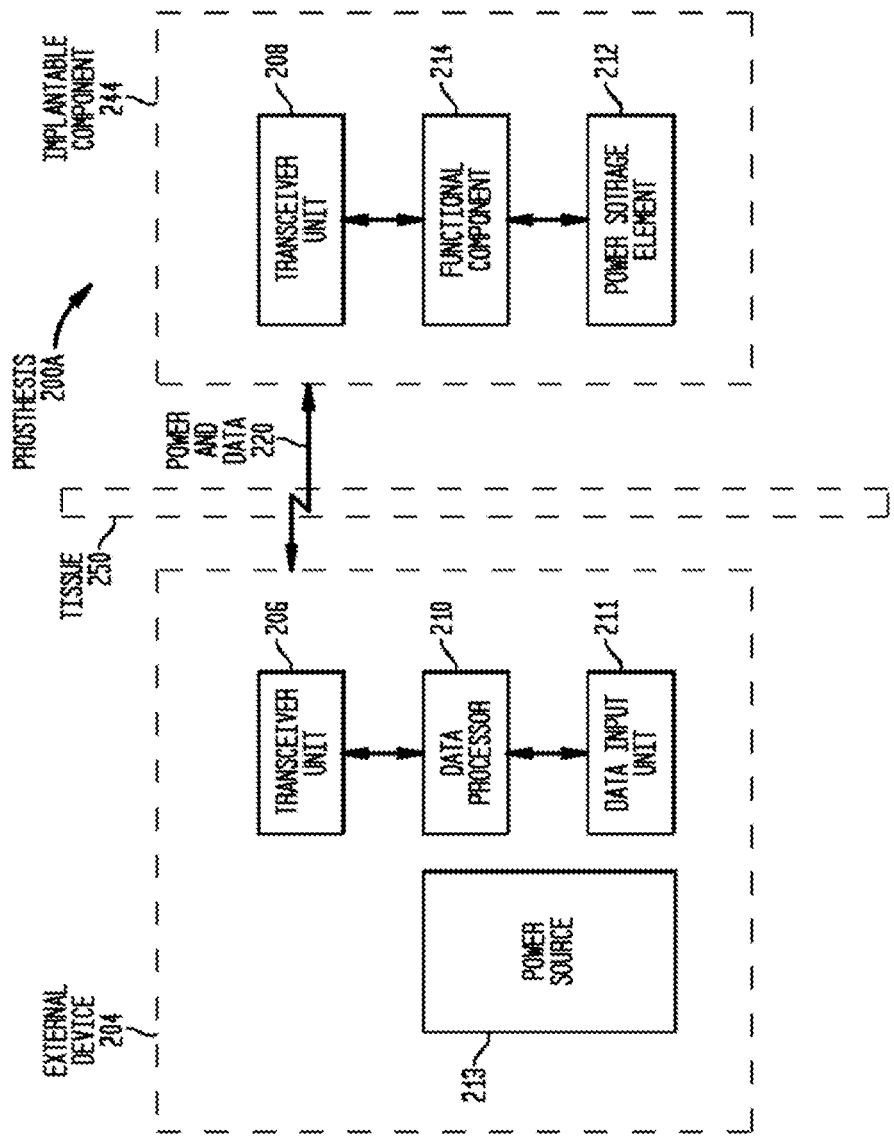

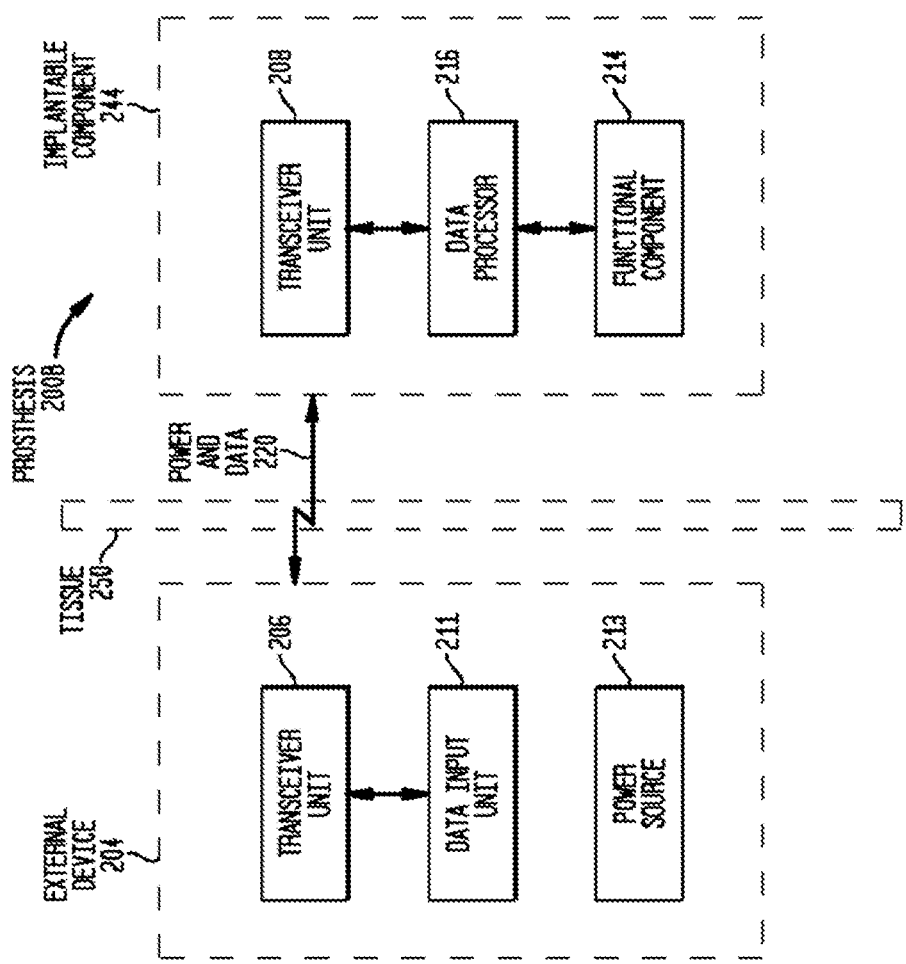

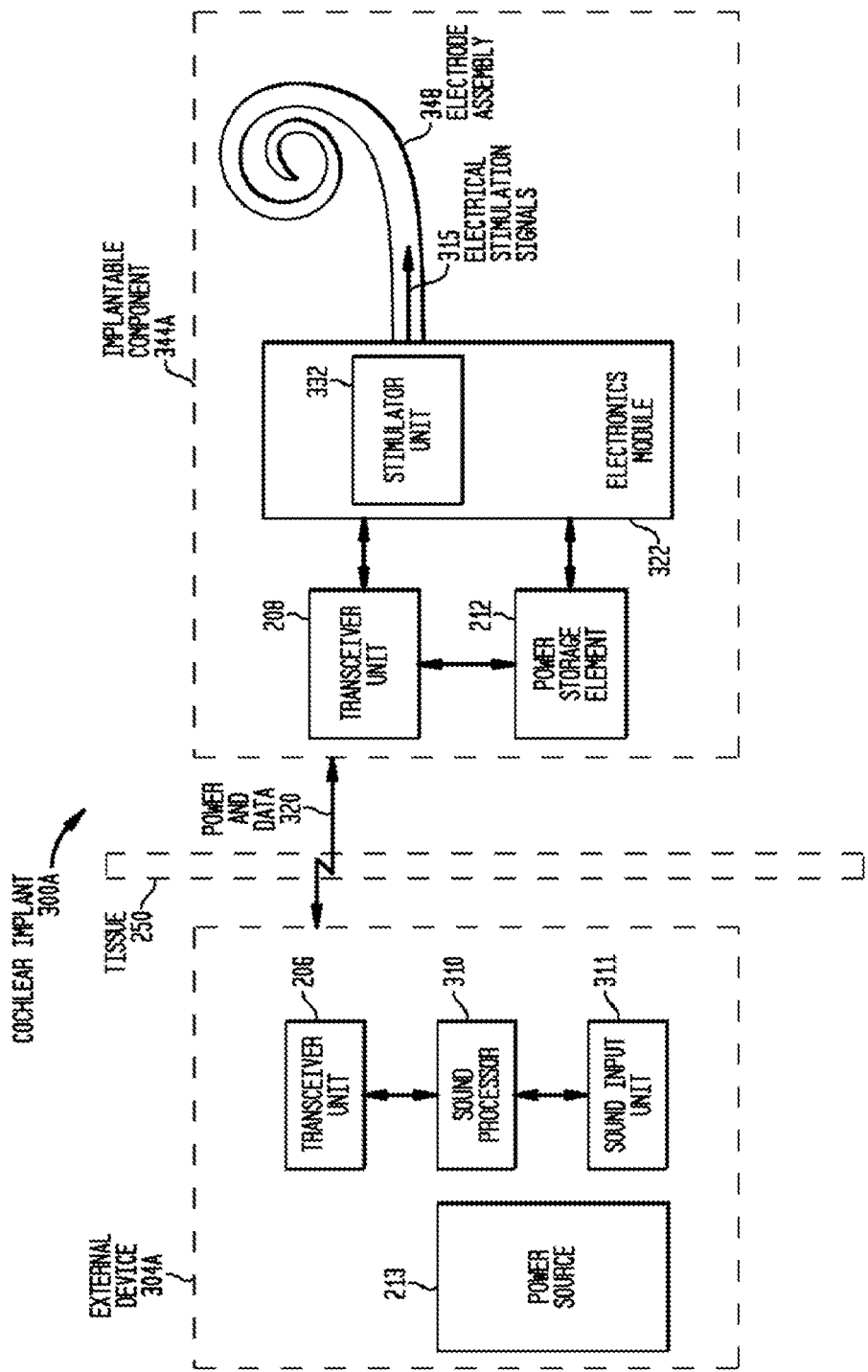

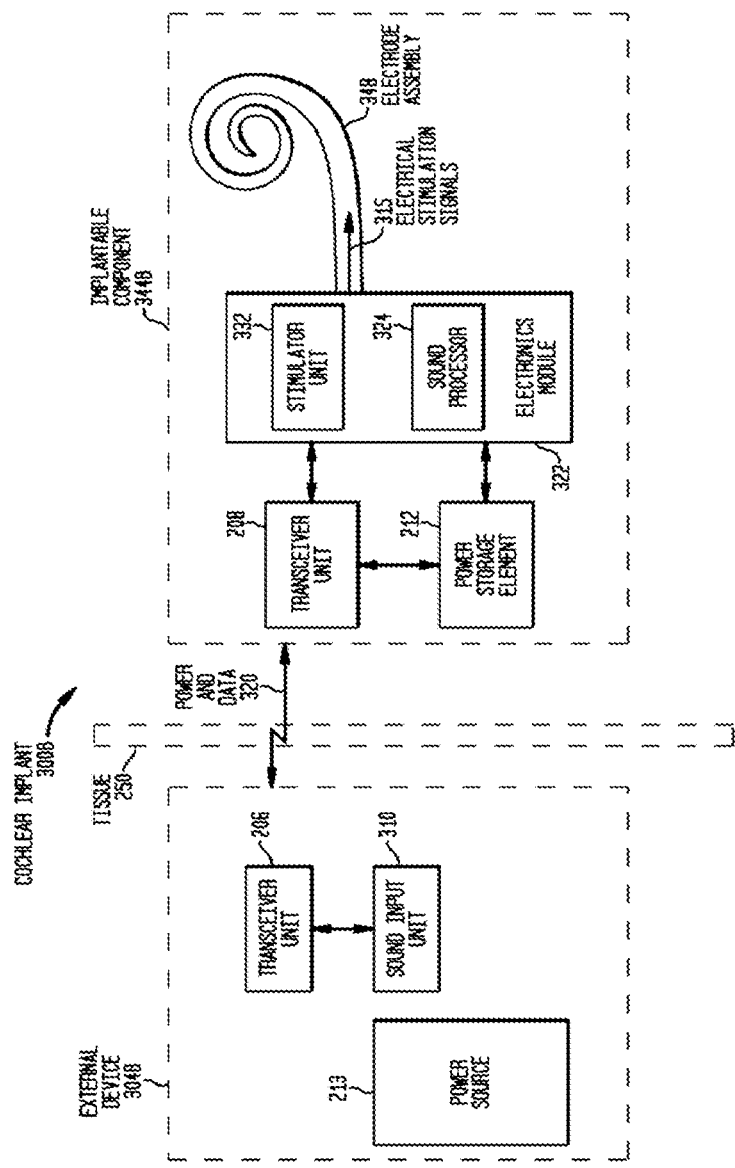

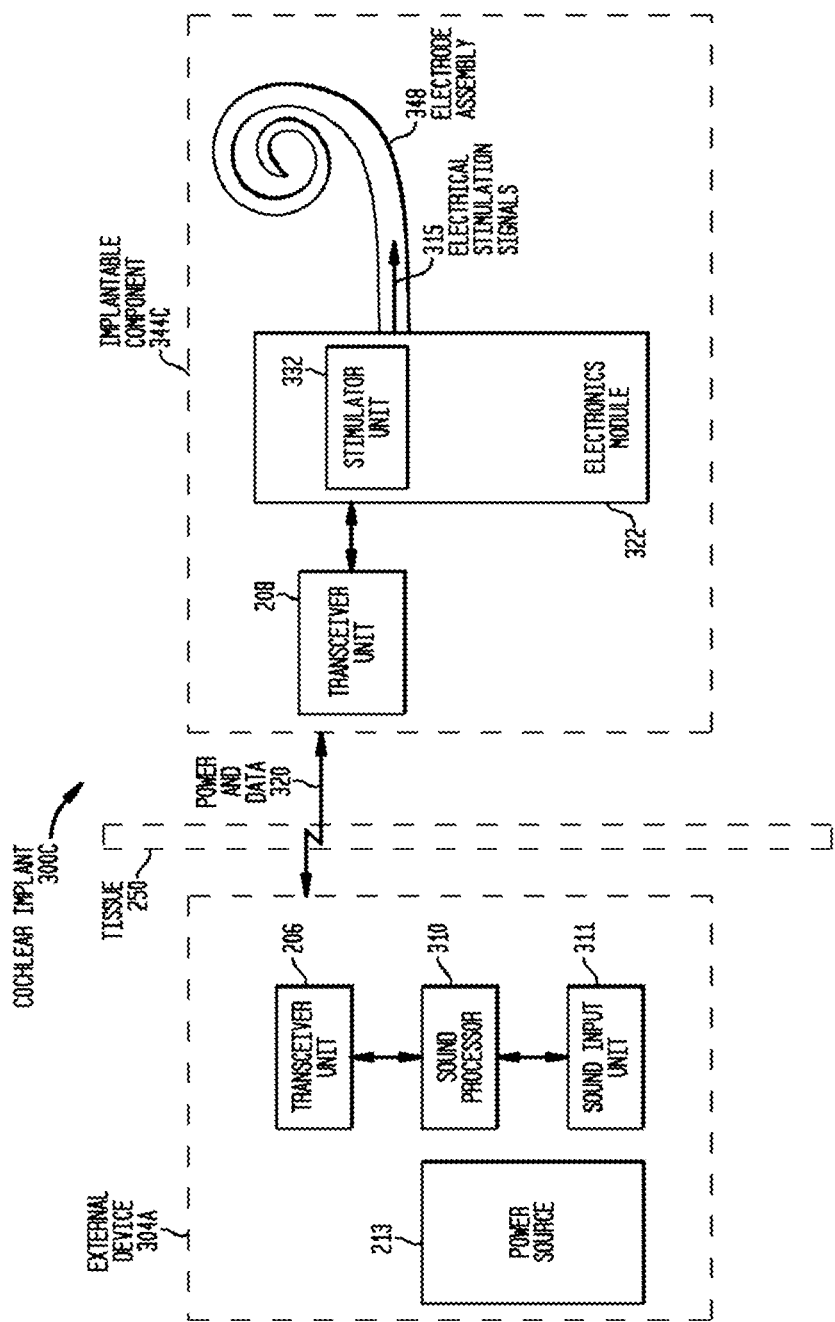

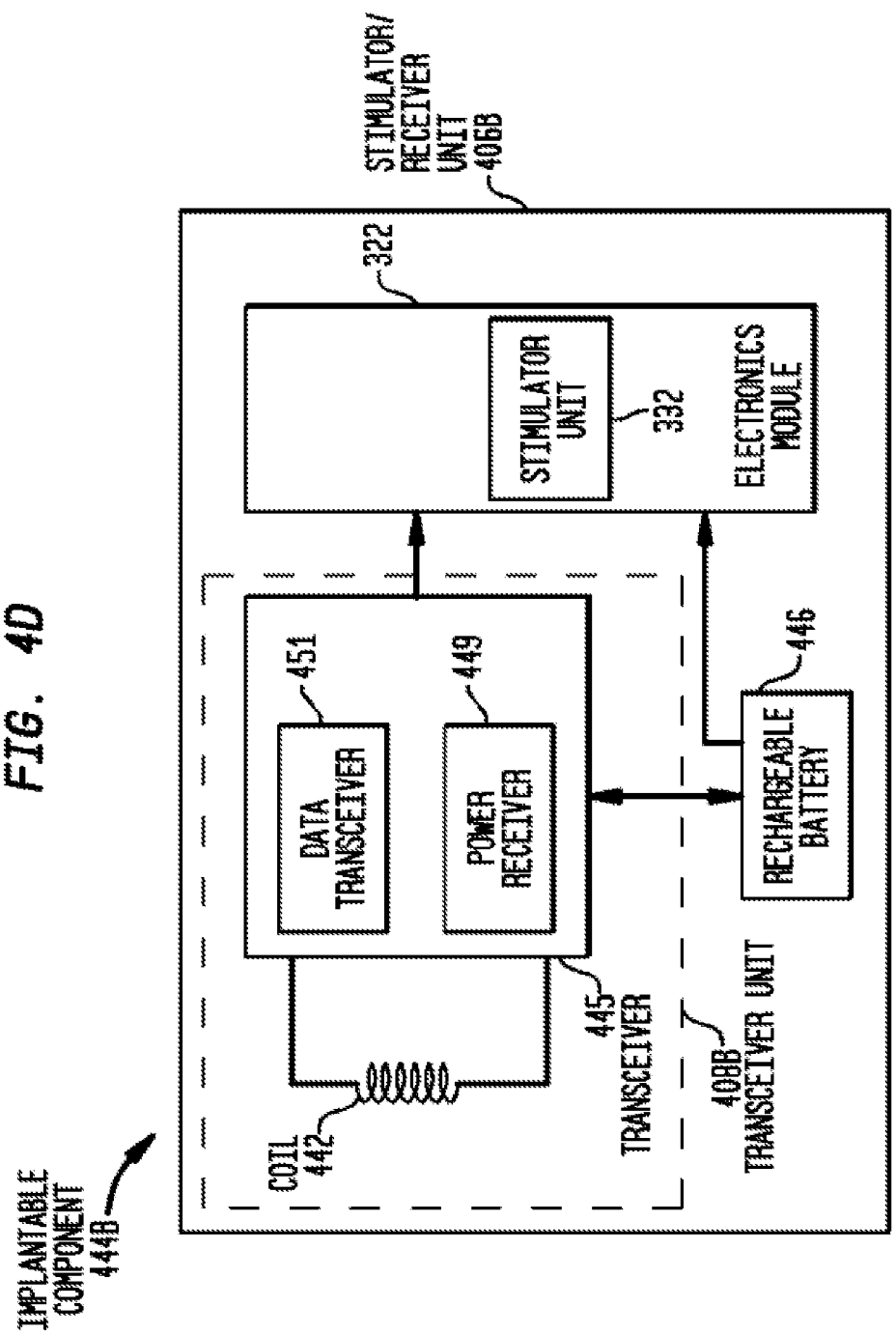

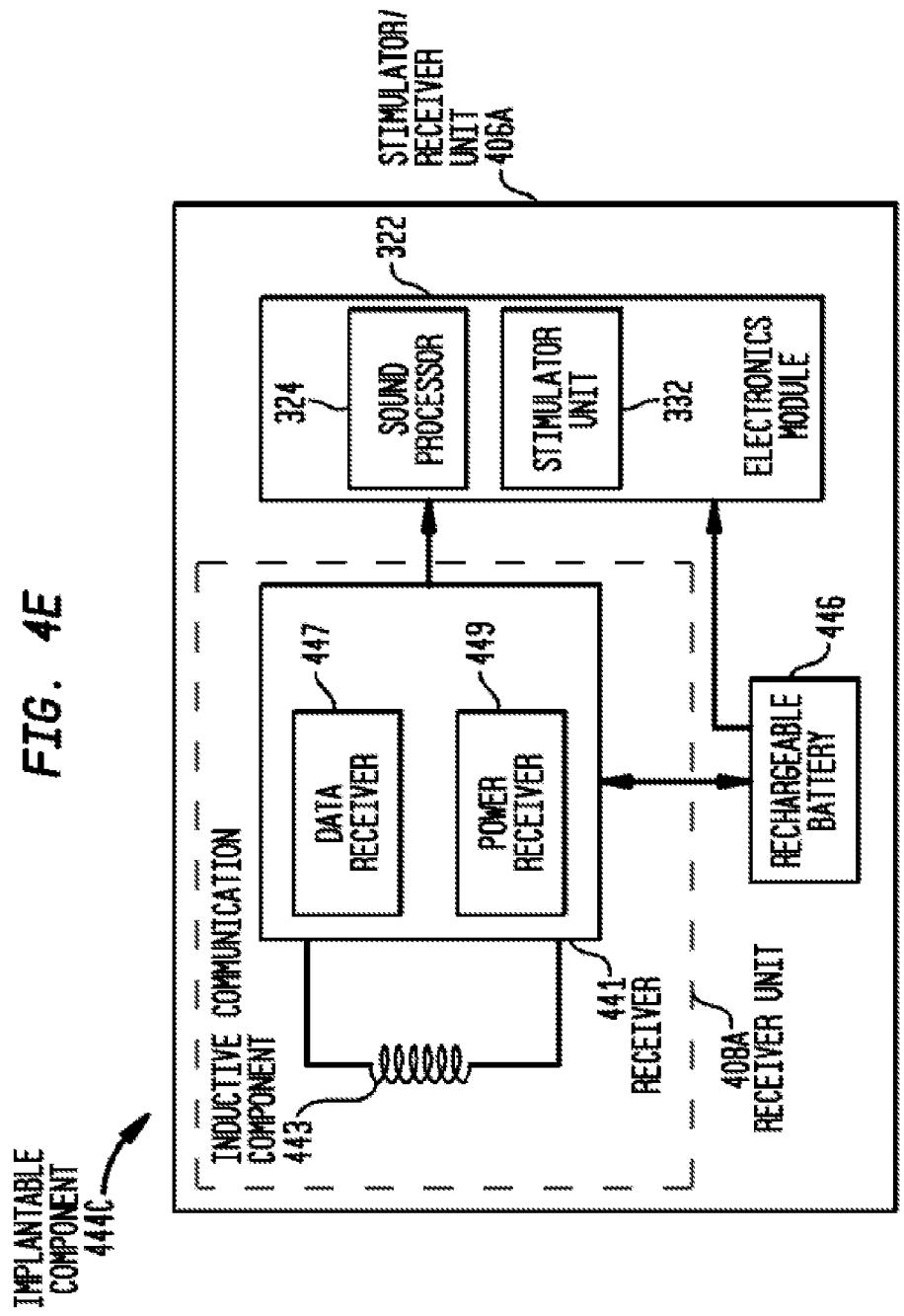

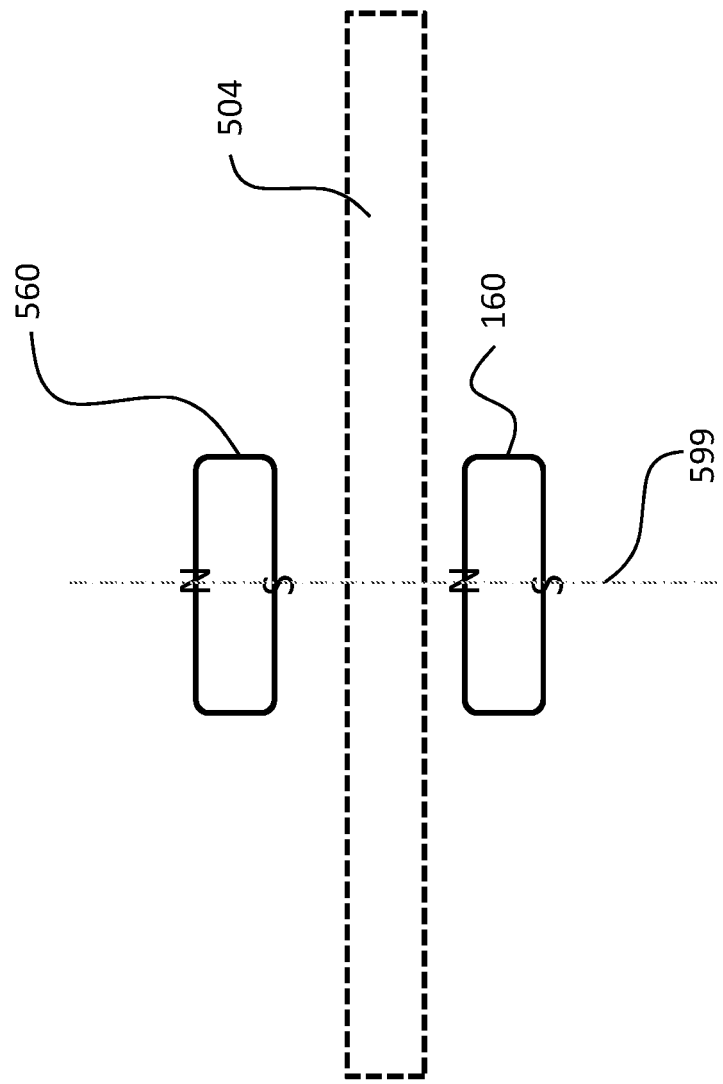

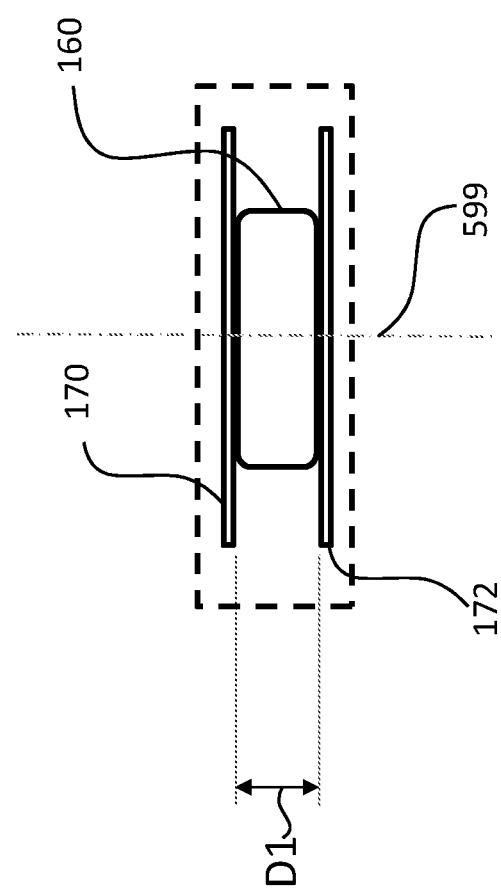

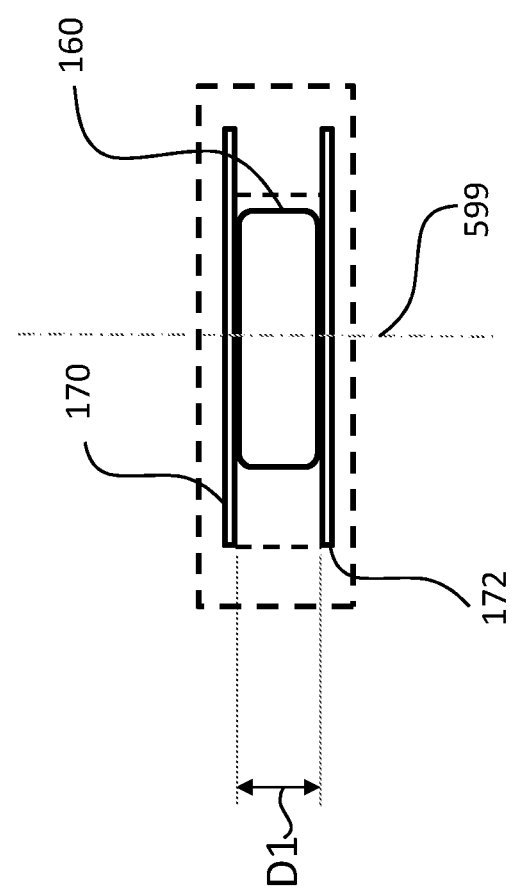

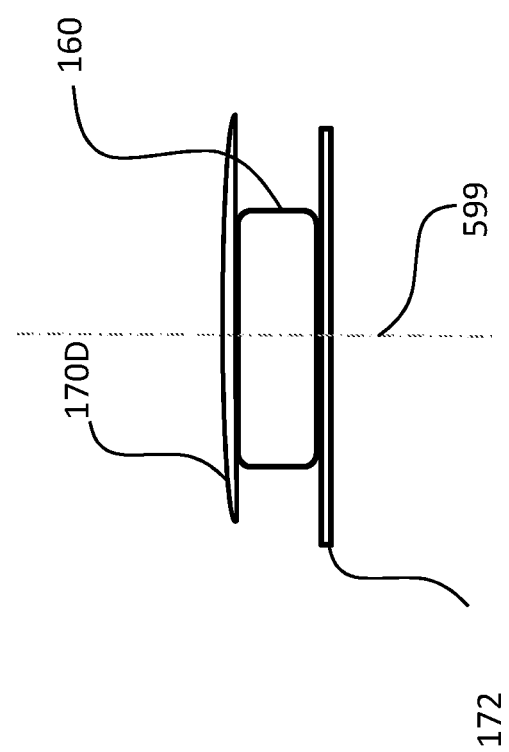

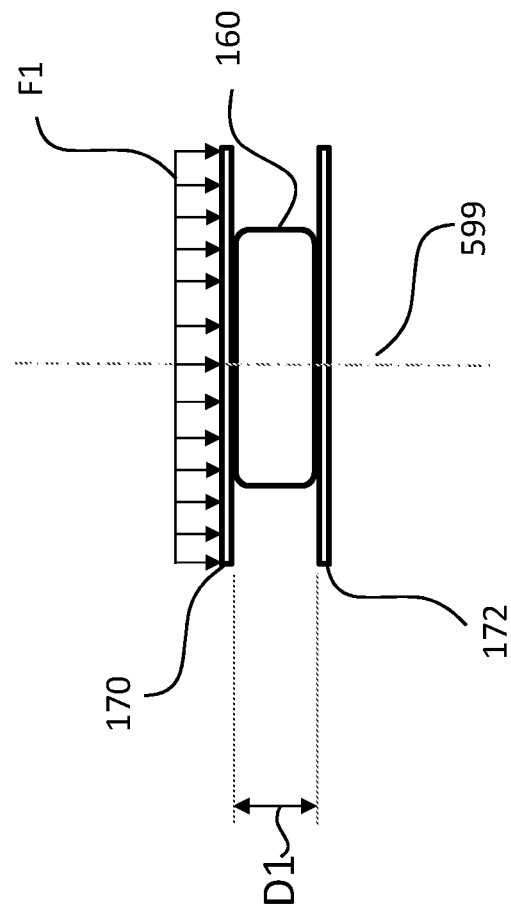

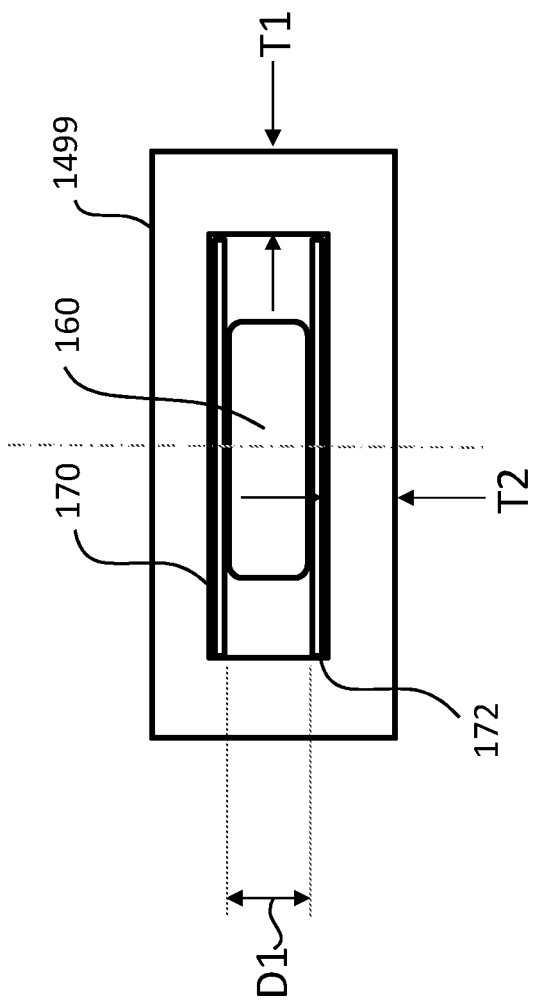

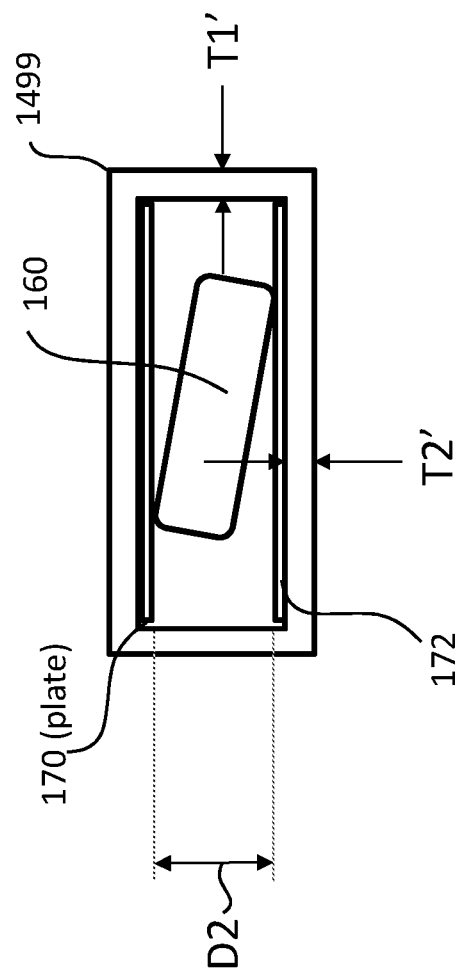

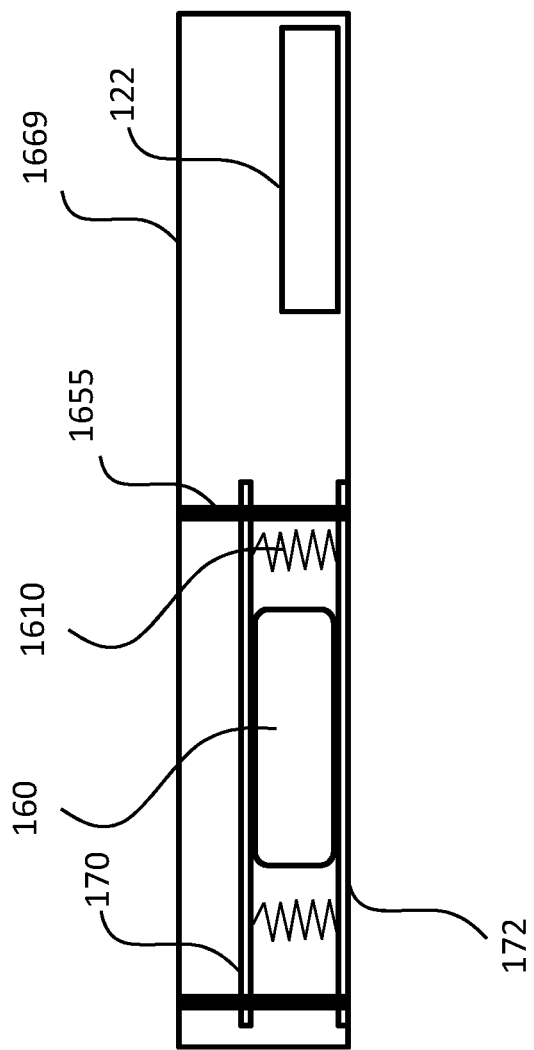

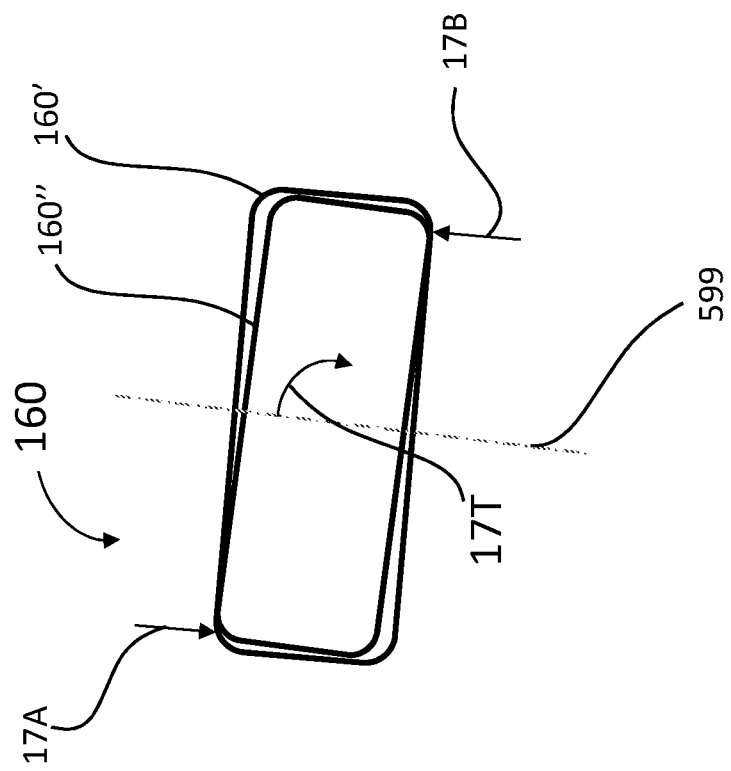

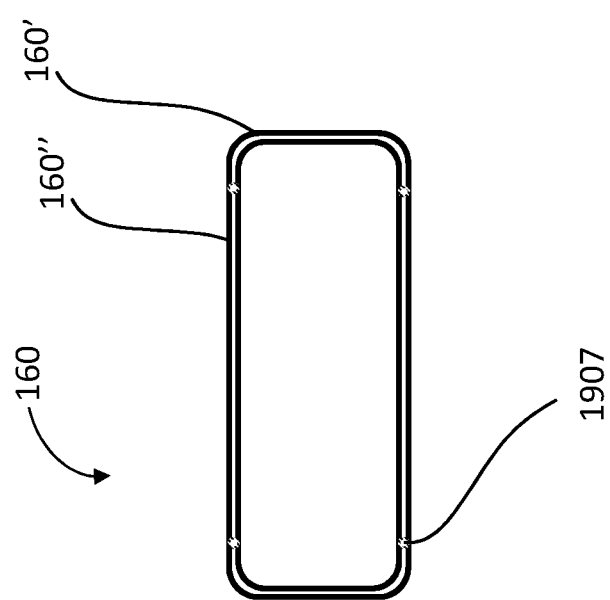

MAGNET MANAGEMENT MRI COMPATIBILITY

CROSS-REFERENCE TO RELATED APPLICATIONS

This application is a Continuation application of U.S. patent application Ser. No. 17/509,842, filed Oct. 25, 2021, which is a Continuation application of U.S. patent application Ser. No. 16/195,655, filed Nov. 19, 2018, now U.S. Pat. No. 11,154,711, which is a Continuation application of U.S. patent application Ser. No. 15/010,410, filed Jan. 29, 2016, now U.S. Pat. No. 10,130,807, which claims priority from Provisional U.S. Patent Application No. 62/174,788, entitled MAGNET MANAGEMENT MRI COMPATIBILITY, filed on Jun. 12, 2015, naming Charles Roger LEIGH of Australia as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is an implantable medical device, comprising a magnet, and a body encompassing the magnet, wherein the implantable medical device includes structural components in the body configured to move away from one another upon initial rotation of the magnet relative to the body when the magnet is subjected to an externally generated magnetic field that imparts a torque onto the magnet, thereby limiting rotation of the magnet beyond the initial rotation.

In accordance with another exemplary embodiment, there is an implantable medical device, comprising a magnet apparatus, and a body encompassing the magnet apparatus, wherein the implantable medical device resists rotation of the magnet apparatus relative to the body in at least one plane when subjected to an externally generated magnetic field that imparts a torque onto the magnet apparatus due to a component relative to which the magnet apparatus is slidable, wherein the component located within the body.

In accordance with another exemplary embodiment, there is an implantable medical device, comprising a magnet and an elastomeric body encompassing the magnet, wherein the body has a slit configured to enable passage of the magnet therethrough.

In according with another exemplary embodiment, there is a method, comprising subjecting a subcutaneous medical device containing a magnet to a magnetic field of at least 0.2 T, thereby imparting a torque onto the magnet, the torque having a component in a plane normal to a surface of skin of the recipient, and limiting at least a portion of the torque of the magnet that is imparted to a support apparatus of the medical device supporting the magnet via structure of the subcutaneous medical device.

BRIEF DESCRIPTION OF THE DRAWINGS

Embodiments are described below with reference to the attached drawings, in which:

FIG. 1B is a top view of an exemplary hearing prosthesis in which at least some of the teachings detailed herein are applicable;

FIG. 2A is a functional block diagram of a prosthesis, in accordance with embodiments of the present invention;

FIG. 2B is an alternate functional block diagram of a prosthesis, in accordance with embodiments of the present invention;

FIG. 3A is a functional block diagram of a cochlear implant, in accordance with embodiments of the present invention:

FIG. 3B is an alternate functional block diagram of a cochlear implant, in accordance with embodiments of the present invention;

FIG. 3C is yet another alternate functional block diagram of a cochlear implant, in accordance with embodiments of the present invention;

FIG. 4D is a simplified schematic diagram of a stimulator/receiver unit including a data transceiver of an implantable device in accordance with embodiments of the present invention;

FIG. 4E is a simplified schematic diagram of a stimulator/receiver unit including a data receiver and a communication component configured to vary the effective coil area of an implantable device in accordance with embodiments of the present invention;

FIG. 5 is an exemplary conceptual schematic of a magnet system arrangement according to an exemplary embodiment;

FIGS. 7A-7D represent exemplary conceptual schematics of an assembly according to an exemplary embodiment;

FIG. 8 depicts a functional schematic of an exemplary scenario resulting from use of an exemplary embodiment;

FIG. 14 represents an exemplary conceptual schematic of an assembly according to an exemplary embodiment;

FIG. 15 represents an exemplary scenario of conceptual use according to an exemplary embodiment;

FIGS. 16A-D present exemplary conceptual schematics of various assemblies according to various exemplary embodiments;

FIG. 17 represents an exemplary scenario of conceptual use according to an exemplary embodiment;

FIG. 19 represents an exemplary conceptual schematic of an assembly according to an exemplary embodiment;

DETAILED DESCRIPTION

Exemplary embodiments will be described in terms of a cochlear implant. That said, it is noted that the teachings detailed herein and/or variations thereof can be utilized with other types of hearing prosthesis, such as by way of example, bone conduction devices, DACI/DACS/middle ear implants, etc. Still further, it is noted that the teachings detailed herein and/or variations thereof can be utilized with other types of prostheses, such as pacemakers, muscle stimulators, etc. In some instances, the teachings detailed herein and/or variations thereof are applicable to any type of implanted component (herein referred to as a medical device) having a magnet that is implantable in a recipient.

Figure 1A:
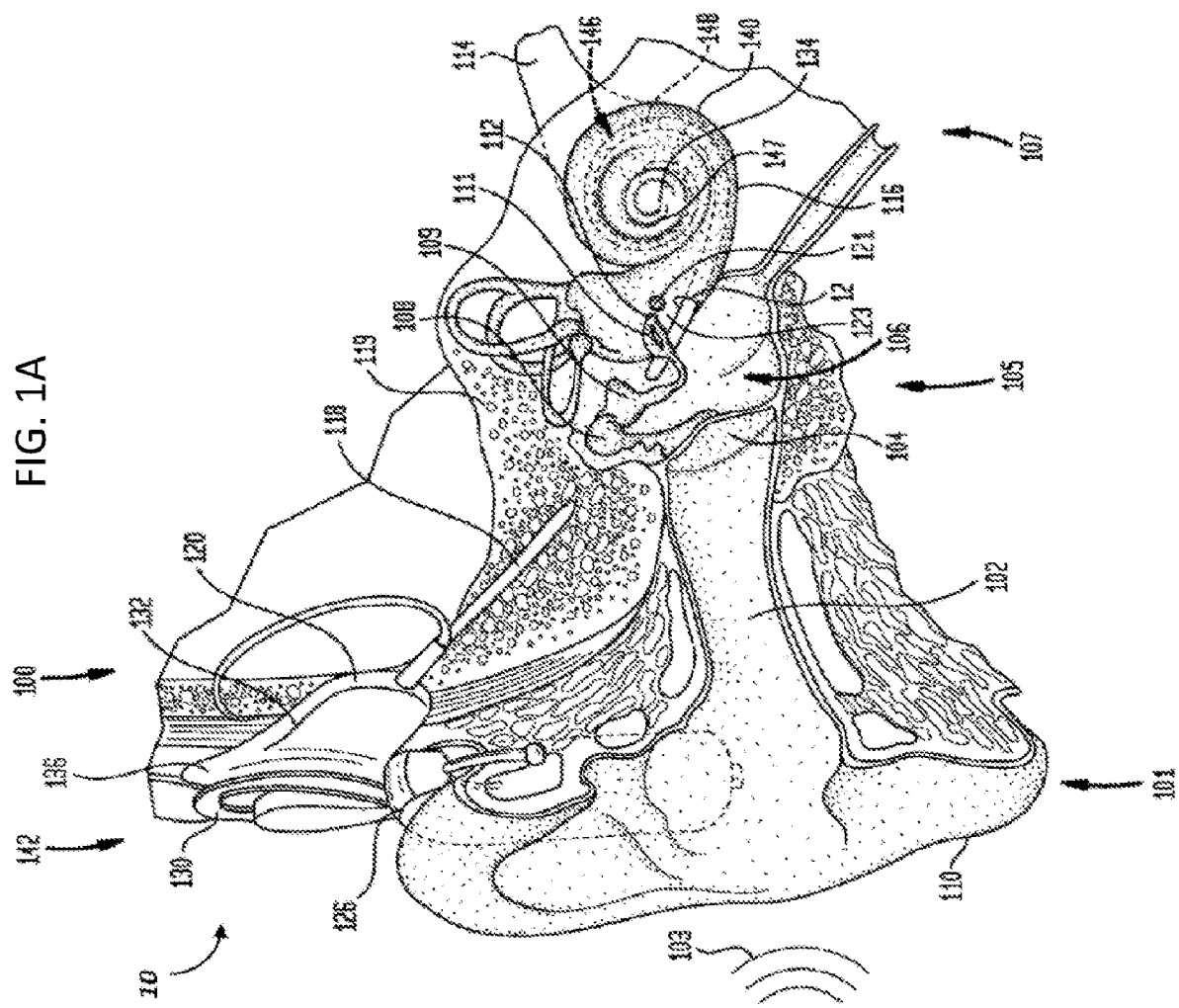
FIG. 1A is a perspective view of an exemplary hearing prosthesis in which at least some of the teachings detailed herein are applicable.

FIG. 1A is a perspective view of a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below. It is noted that the teachings detailed herein are applicable, in at least some embodiments, to partially implantable and/or totally implantable cochlear implants (i.e., with regard to the latter, such as those having an implanted microphone). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prosthesis, such as by way of example only and not by way of limitation, bone conduction devices, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1A, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1A with an external device 142, that is part of system 10 (along with cochlear implant 100), which, as described below, is configured to provide power to the cochlear implant, and where the implanted cochlear implant includes a battery, that is recharged by the power provided from the external device 142.

In the illustrative arrangement of FIG. 1A, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1A, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1A is merely illustrative, and other external devices may be used with embodiments of the present invention.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil assembly 136. Internal coil assembly 136 typically includes a wire antenna coil comprised of multiple turns of electrically insulated single-strand or multi-strand platinum or gold wire, as will be described in greater detail below.

Cochlear implant 100 further comprises a main implantable component 120 and an elongate electrode assembly 118. Collectively, the coil assembly 136, the main implantable component 120, and the electrode assembly 118 correspond to the implantable component of the system 10.

In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone or via internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown in FIG. 1A) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123 or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Figure 1C:
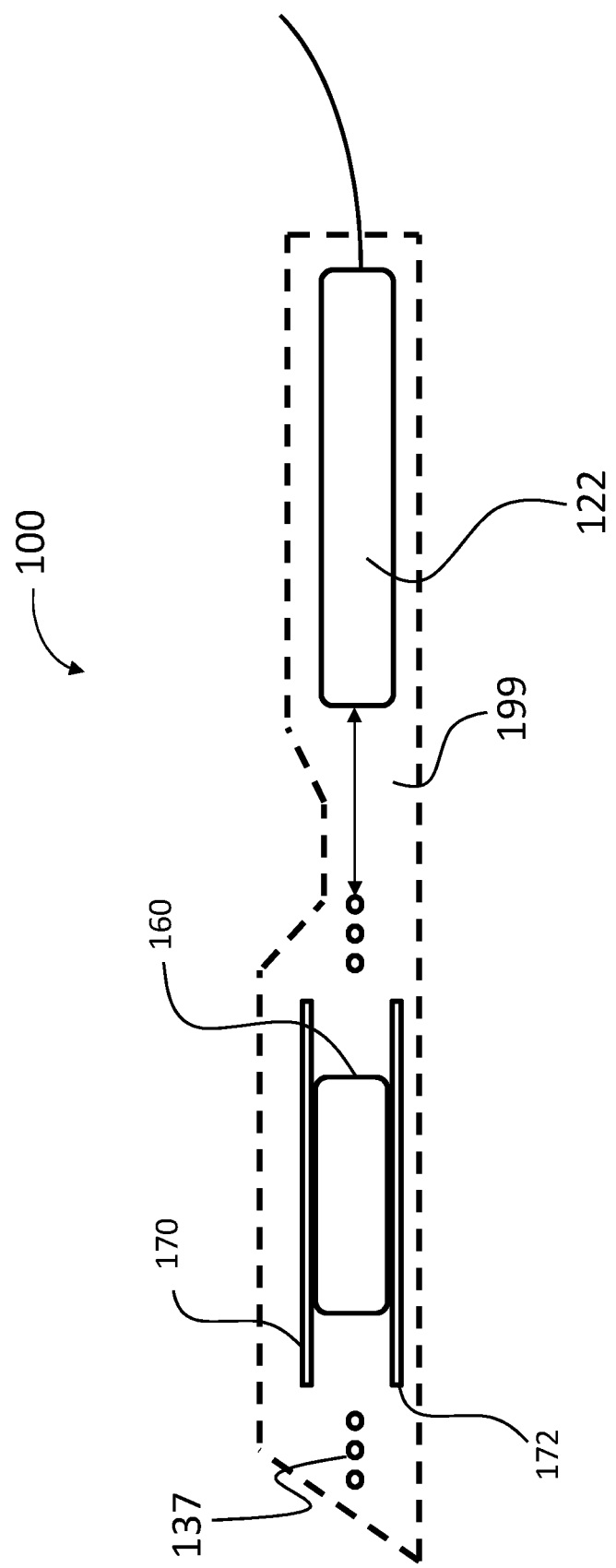
FIG. 1C is a side view of an exemplary hearing prosthesis in which at least some of the teachings detailed herein are applicable.

FIG. 1B depicts an exemplary high-level diagram of the implantable component 100 of the system 10, looking downward from outside the skull towards the skull. As can be seen, implantable component 100 includes a magnet 160 that is surrounded by a coil 137 that is in two-way communication (although in other embodiments, the communication is one-way) with a stimulator unit 122, which in turn is in communication with the electrode assembly 118. Implantable component 100 further includes a plate 170 that is located above the magnet 160 (relative to the view of FIG. 1B). In the exemplary embodiment presented in FIG. 1B, the longitudinal axis of the plate 170 is at least generally aligned (including aligned) with the magnet apparatus 160, although in other embodiments, such alignment is not present. Not seen in FIG. 1B, but as can be seen in FIG. 1C (representing a side cross-sectional view of the implantable component 100 of FIG. 1B taken down the center of the implantable component 100), is another plate 172 located on the opposite side of the magnet apparatus 160, resulting in, in this exemplary embodiment, the magnet apparatus 160 being sandwiched by the plates. In at least some embodiments, plate 172 is identical to the plate 170, while in other embodiments, the plates are different. Additional features of these plates will be described in greater detail below.

Still with reference to FIG. 1B, it is noted that the plate 170 (and the bottom plate), the stimulator unit 122, and the magnet apparatus 170 are located in a housing made of an elastomeric material 199, such as by way of example only and not by way of limitation, silicone. Hereinafter, the elastomeric material 199 of the housing will be often referred to as silicone. However, it is noted that any reference to silicone herein also corresponds to a reference to any other type of component that will enable the teachings detailed herein and/or variations thereof, such as, by way of example and not by way of limitation only, bio-compatible rubber, etc.

As can be seen in FIG. 1B, the housing made of elastomeric material 199 includes a slit 180 (not shown in FIG. 1C, as, in some embodiments, the slit is not utilized). In an exemplary embodiment, the slit 180 has utilitarian value in that it can enable insertion and/or removal of the magnet apparatus 160 from the housing made of elastomeric material 199.

It is noted that magnet apparatus 160 is presented in a conceptual manner. In this regard, it is noted that in at least some embodiments, the magnet apparatus 160 is an assembly that includes a magnet surrounded by a biocompatible coating. Still further, in an exemplary embodiment, magnet apparatus 160 is an assembly where the magnet is located within a container having interior dimensions generally corresponding to the exterior dimensions of the magnet. This container can be hermetically sealed, thus isolating the magnet in the container from body fluids of the recipient that penetrate the housing (the same principle of operation occurs with respect to the aforementioned coated magnet). In an exemplary embodiment, this container permits the magnet to revolve or otherwise move relative to the container. Additional details of the container will be described below. In this regard, it is noted that while sometimes the term magnet is used as shorthand for the phrase magnet apparatus, and thus any disclosure herein with respect to a magnet also corresponds to a disclosure of a magnet apparatus according to the aforementioned embodiments and/or variations thereof and/or any other configuration that can have utilitarian value according to the teachings detailed herein.

With reference now to FIG. 1C, it is noted that the outlines of the housing made from elastomeric material 199 are presented in dashed line format for ease of discussion. In an exemplary embodiment, silicone or some other elastomeric material fills the interior within the dashed line, other than the other components of the implantable device (e.g., plates, magnet, stimulator, etc.). That said, in an alternative embodiment, silicone or some other elastomeric material substantially fills the interior within the dashed lines other than the components of the implantable device (e.g., there can be pockets within the dashed line in which no components and no silicone is located).

It is noted that FIGS. 1B and 1C are conceptual FIGS. presented for purposes of discussion. Commercial embodiments corresponding to these FIGS. can be different from that depicted in the figures.

Additional details of the plates, magnets, and housing made of elastomeric material will be described in greater detail below. First, however, additional functional details of the cochlear implant 100 will now be described.

FIG. 2A is a functional block diagram of a prosthesis 200A in accordance with embodiments of the present invention. Prosthesis 200A comprises an implantable component 244 configured to be implanted beneath a recipient's skin or other tissue 250 and an external device 204. For example, implantable component 244 may be implantable component 100 of FIG. 1A, and external device may be the external device 142 of FIG. 1A. Similar to the embodiments described above with reference to FIG. 1A, implantable component 244 comprises a transceiver unit 208 which receives data and power from external device 204. External device 204 transmits power and data 220 via transceiver unit 206 to transceiver unit 208 via a magnetic induction data link 220. As used herein, the term receiver refers to any device or component configured to receive power and/or data such as the receiving portion of a transceiver or a separate component for receiving. The details of transmission of power and data to transceiver unit 208 are provided below. With regard to transceivers, it is noted at this time that while embodiments of the present invention may utilize transceivers, separate receivers and/or transmitters may be utilized as appropriate. This will be apparent in view of the description below.

Implantable component 244 may comprises a power storage element 212 and a functional component 214. Power storage element 212 is configured to store power received by transceiver unit 208, and to distribute power, as needed, to the elements of implantable component 244. Power storage element 212 may comprise, for example, a rechargeable battery 212. An example of a functional component may be a stimulator unit 120 as shown in FIG. 1B.

In certain embodiments, implantable component 244 may comprise a single unit having all components of the implantable component 244 disposed in a common housing. In other embodiments, implantable component 244 comprises a combination of several separate units communicating via wire or wireless connections. For example, power storage element 212 may be a separate unit enclosed in a hermetically sealed housing. The implantable magnet apparatus and plates associated therewith may be attached to or otherwise be a part of any of these units, and more than one of these units can include the magnet apparatus and plates according to the teachings detailed herein and/or variations thereof.

In the embodiment depicted in FIG. 2A, external device 204 includes a data processor 210 that receives data from data input unit 211 and processes the received data. The processed data from data processor 210 is transmitted by transceiver unit 206 to transceiver unit 208. In an exemplary embodiment, data processor 210 may be a sound processor, such as the sound processor of FIG. 1A for the cochlear implant thereof, and data input unit 211 may be a microphone of the external device.

FIG. 2B presents an alternate embodiment of the prosthesis 200A of FIG. 2A, identified in FIG. 2B as prosthesis 200B. As may be seen from comparing FIG. 2A to FIG. 2B, the data processor can be located in the external device 204 or can be located in the implantable component 244. In some embodiments, both the external device 204 and the implantable component 244 can include a data processor.

As shown in FIGS. 2A and 2B, external device 204 can include a power source 213. Power from power source 213 can be transmitted by transceiver unit 206 to transceiver unit 208 to provide power to the implantable component 244, as will be described in more detail below.

While not shown in FIGS. 2A and 2B, external device 204 and/or implantable component 244 include respective inductive communication components. These inductive communication components can be connected to transceiver unit 206 and transceiver unit 208, permitting power and data 220 to be transferred between the two units via magnetic induction.

As used herein, an inductive communication component includes both standard induction coils and inductive communication components configured to vary their effective coil areas.

As noted above, prosthesis 200A of FIG. 2A may be a cochlear implant. In this regard, FIG. 3A provides additional details of an embodiment of FIG. 2A where prosthesis 200A is a cochlear implant. Specifically, FIG. 3A is a functional block diagram of a cochlear implant 300 in accordance with embodiments of the present invention.

It is noted that the components detailed in FIGS. 2A and 2B may be identical to the components detailed in FIG. 3A, and the components of 3A may be used in the embodiments depicted in FIGS. 2A and 2B.

Cochlear implant 300A comprises an implantable component 344A (e.g., implantable component 100 of FIG. 1) configured to be implanted beneath a recipient's skin or other tissue 250, and an external device 304A. External device 304A may be an external component such as external component 142 of FIG. 1.

Similar to the embodiments described above with reference to FIGS. 2A and 2B, implantable component 344A comprises a transceiver unit 208 (which may be the same transceiver unit used in FIGS. 2A and 2B) which receives data and power from external device 304A. External device 304A transmits data and/or power 320 to transceiver unit 208 via a magnetic induction data link. This can be done while charging module 202.

Implantable component 344A also comprises a power storage element 212, electronics module 322 (which may include components such as sound processor 126 and/or may include a stimulator unit 322 corresponding to stimulator unit 122 of FIG. 1B) and an electrode assembly 348 (which may include an array of electrode contacts 148 of FIG. 1A). Power storage element 212 is configured to store power received by transceiver unit 208, and to distribute power, as needed, to the elements of implantable component 344A.

As shown, electronics module 322 includes a stimulator unit 332. Electronics module 322 can also include one or more other functional components used to generate or control delivery of electrical stimulation signals 315 to the recipient. As described above with respect to FIG. 1A, electrode assembly 348 is inserted into the recipient's cochlea and is configured to deliver electrical stimulation signals 315 generated by stimulator unit 332 to the cochlea.

In the embodiment depicted in FIG. 3A, the external device 304A includes a sound processor 310 configured to convert sound signals received from sound input unit 311 (e.g., a microphone, an electrical input for an FM hearing system, etc.) into data signals. In an exemplary embodiment, the sound processor 310 corresponds to data processor 210 of FIG. 2A.

FIG. 3B presents an alternate embodiment of a cochlear implant 300B. The elements of cochlear implant 300B correspond to the elements of cochlear implant 300A except that external device 304B does not include sound processor 310. Instead, the implantable component 344B includes a sound processor 324, which may correspond to sound processor 310 of FIG. 3A.

As will be described in more detail below, while not shown in the figures, external device 304A/304B and/or implantable component 344A/344B include respective inductive communication components.

FIGS. 3A and 3B illustrate that external device 304A/304B can include a power source 213, which may be the same as power source 213 depicted in FIG. 2A. Power from power source 213 can be transmitted by transceiver unit 306 to transceiver unit 308 to provide power to the implantable component 344A/344B, as will be detailed below. FIGS. 3A and 3B further detail that the implantable component 344A/344B can include a power storage element 212 that stores power received by the implantable component 344 from power source 213. Power storage element 212 may be the same as power storage element 212 of FIG. 2A.

In contrast to the embodiments of FIGS. 3A and 3B, as depicted in FIG. 3C, an embodiment of the present invention of a cochlear implant 300C includes an implantable component 344C that does not include a power storage element 212. In the embodiment of FIG. 3C, sufficient power is supplied by external device 304A/304B in real time to power implantable component 344C without storing power in a power storage element. In FIG. 3C, all of the elements are the same as FIG. 3A except for the absence of power storage element 212.

Some of the components of FIGS. 3A-3C will now be described in greater detail.

Figure 4A:
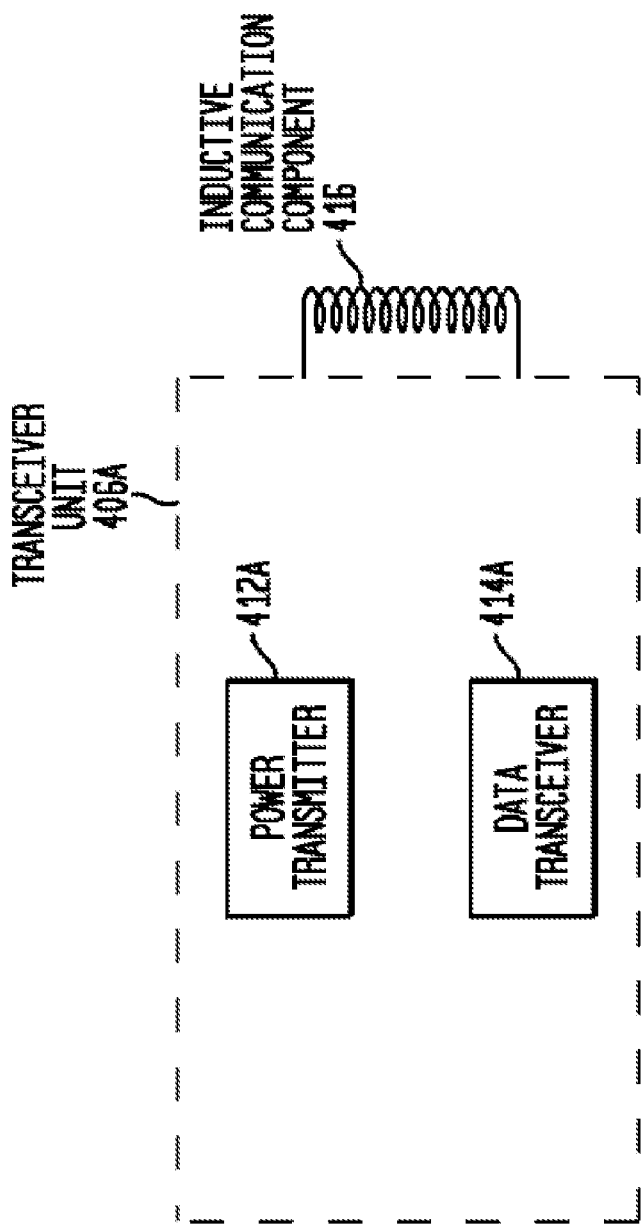
FIG. 4A is a simplified schematic diagram of a transceiver unit of an external device in accordance with embodiments of the present invention.

FIG. 4A is a simplified schematic diagram of a transceiver unit 406A in accordance with an embodiment of the present invention. An exemplary transceiver unit 406A may correspond to transceiver unit 206 of FIGS. 2A-3C. As shown, transceiver unit 406A includes a power transmitter 412 a, a data transceiver 414A and an inductive communication component 416.

In an exemplary embodiment, as will be described in more detail below, inductive communication component 416 comprises one or more wire antenna coils (depending on the embodiment) comprised of multiple turns of electrically insulated single-strand or multi-strand platinum or gold wire (thus corresponding to coil 137 of FIG. 1B). Power transmitter 412A comprises circuit components that inductively transmit power from a power source, such as power source 213, via an inductive communication component 416 to implantable component 344A/B/C (FIGS. 3A-3C). Data transceiver 414A comprises circuit components that cooperate to output data for transmission to implantable component 344A/B/C (FIGS. 3A-3C). Transceiver unit 406A can receive inductively transmitted data from one or more other components of cochlear implant 300A/B/C, such as telemetry or the like from implantable component 344A (FIG. 3A).

Transceiver unit 406A can be included in a device that includes any number of components which transmit data to implantable component 334A/B/C. For example, the transceiver unit 406A may be included in a behind-the-ear (BTE) device having one or more of a microphone or sound processor therein, an in-the-ear device, etc.

Figure 4B:
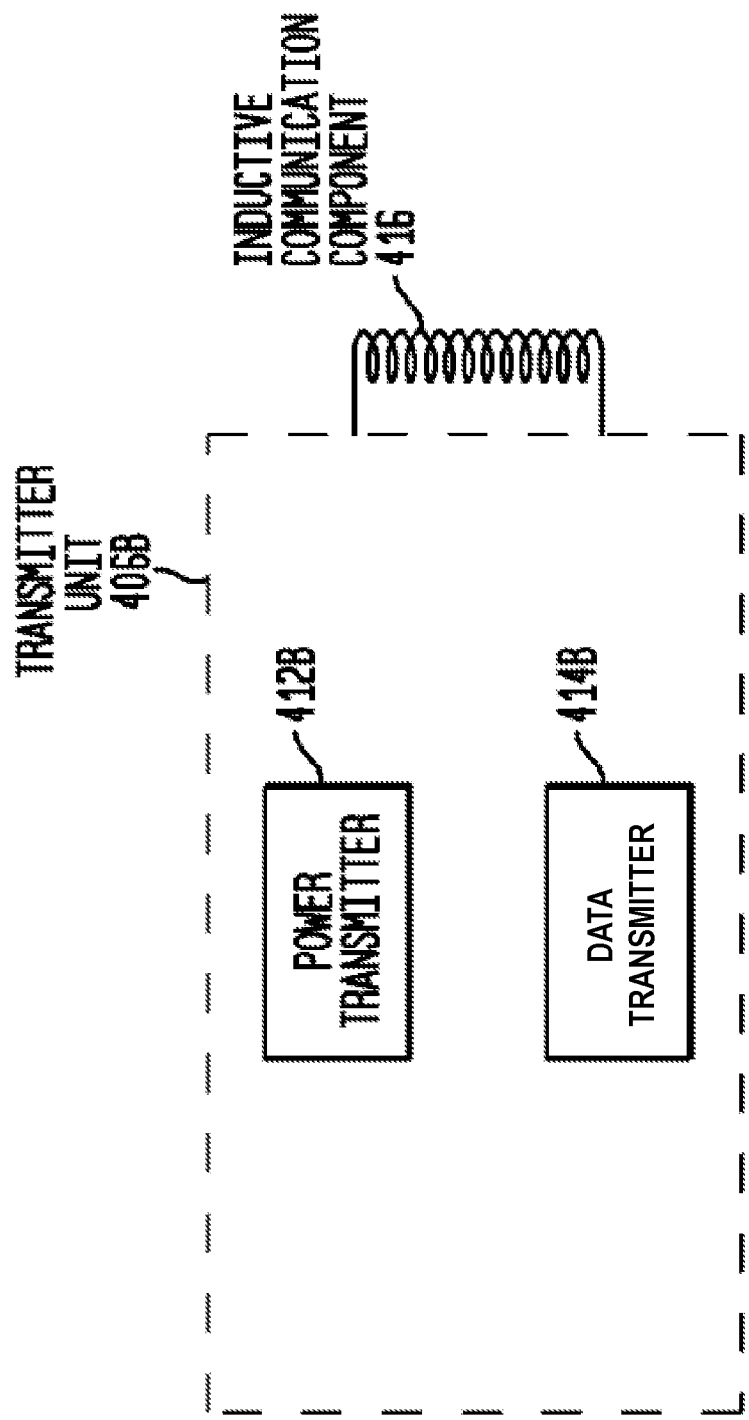
FIG. 4B is a simplified schematic diagram of a transmitter unit of an external device in accordance with embodiments of the present invention.

FIG. 4B depicts a transmitter unit 406B, which is identical to transceiver unit 406A, except that it includes a power transmitter 412B and a data transmitter 414B.

It is noted that for ease of description, power transmitter 412A and data transceiver 414A/data transmitter 414B are shown separate. However, it should be appreciated that in certain embodiments, at least some of the components of the two devices may be combined into a single device.

Figure 4C:
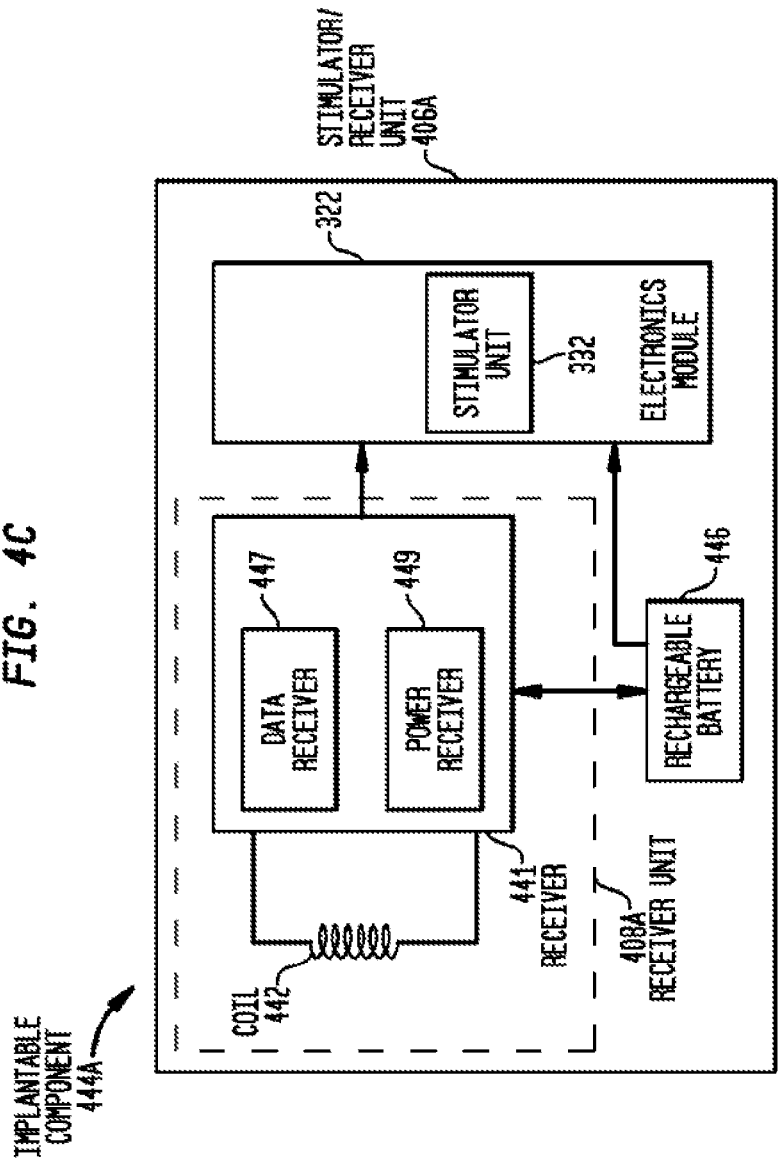
FIG. 4C is a simplified schematic diagram of a stimulator/receiver unit including a data receiver of an implantable device in accordance with embodiments of the present invention.

FIG. 4C is a simplified schematic diagram of one embodiment of an implantable component 444A that corresponds to implantable component 344A of FIG. 3A, except that transceiver unit 208 is a receiver unit. In this regard, implantable component 444A comprises a receiver unit 408A, a power storage element, shown as rechargeable battery 446, and electronics module 322, corresponding to electronics module 322 of FIG. 3A. Receiver unit 408A includes an inductance coil 442 connected to receiver 441. Receiver 441 comprises circuit components which receive via an inductive communication component corresponding to an inductance coil 442 inductively transmitted data and power from other components of cochlear implant 300A/B/C, such as from external device 304A/B. The components for receiving data and power are shown in FIG. 4C as data receiver 447 and power receiver 449. For ease of description, data receiver 447 and power receiver 449 are shown separate. However, it should be appreciated that in certain embodiments, at least some of the components of these receivers may be combined into one component.

In the illustrative embodiments of the present invention, receiver unit 408A and transceiver unit 406A (or transmitter unit 406B) establish a transcutaneous communication link over which data and power is transferred from transceiver unit 406A (or transmitter unit 406B), to implantable component 444A. As shown, the transcutaneous communication link comprises a magnetic induction link formed by an inductance communication component system that includes inductive communication component 416 and coil 442.

The transcutaneous communication link established by receiver unit 408A and transceiver unit 406A (or whatever other viable component can so establish such a link), in an exemplary embodiment, may use time interleaving of power and data on a single radio frequency (RF) channel or band to transmit the power and data to implantable component 444A. A method of time interleaving power according to an exemplary embodiment uses successive time frames, each having a time length and each divided into two or more time slots. Within each frame, one or more time slots are allocated to power, while one or more time slots are allocated to data. In an exemplary embodiment, the data modulates the RF carrier or signal containing power. In an exemplary embodiment, transceiver unit 406A and transmitter unit 406B are configured to transmit data and power, respectively, to an implantable component, such as implantable component 344A, within their allocated time slots within each frame.

The power received by receiver unit 408A can be provided to rechargeable battery 446 for storage. The power received by receiver unit 408A can also be provided for distribution, as desired, to elements of implantable component 444A. As shown, electronics module 322 includes stimulator unit 332, which in an exemplary embodiment corresponds to stimulator unit 322 of FIGS. 3A-3C, and can also include one or more other functional components used to generate or control delivery of electrical stimulation signals to the recipient.

In an embodiment, implantable component 444A comprises a receiver unit 408A, rechargeable battery 446 and electronics module 322 integrated in a single implantable housing, referred to as stimulator/receiver unit 406A. It would be appreciated that in alternative embodiments, implantable component 344 may comprise a combination of several separate units communicating via wire or wireless connections.

FIG. 4D is a simplified schematic diagram of an alternate embodiment of an implantable component 444B. Implantable component 444B is identical to implantable component 444A of FIG. 4C, except that instead of receiver unit 408A, it includes transceiver unit 408B. Transceiver unit 408B includes transceiver 445 (as opposed to receiver 441 in FIG. 4C). Transceiver unit 445 includes data transceiver 451 (as opposed to data receiver 447 in FIG. 4C).

Figure 4F:
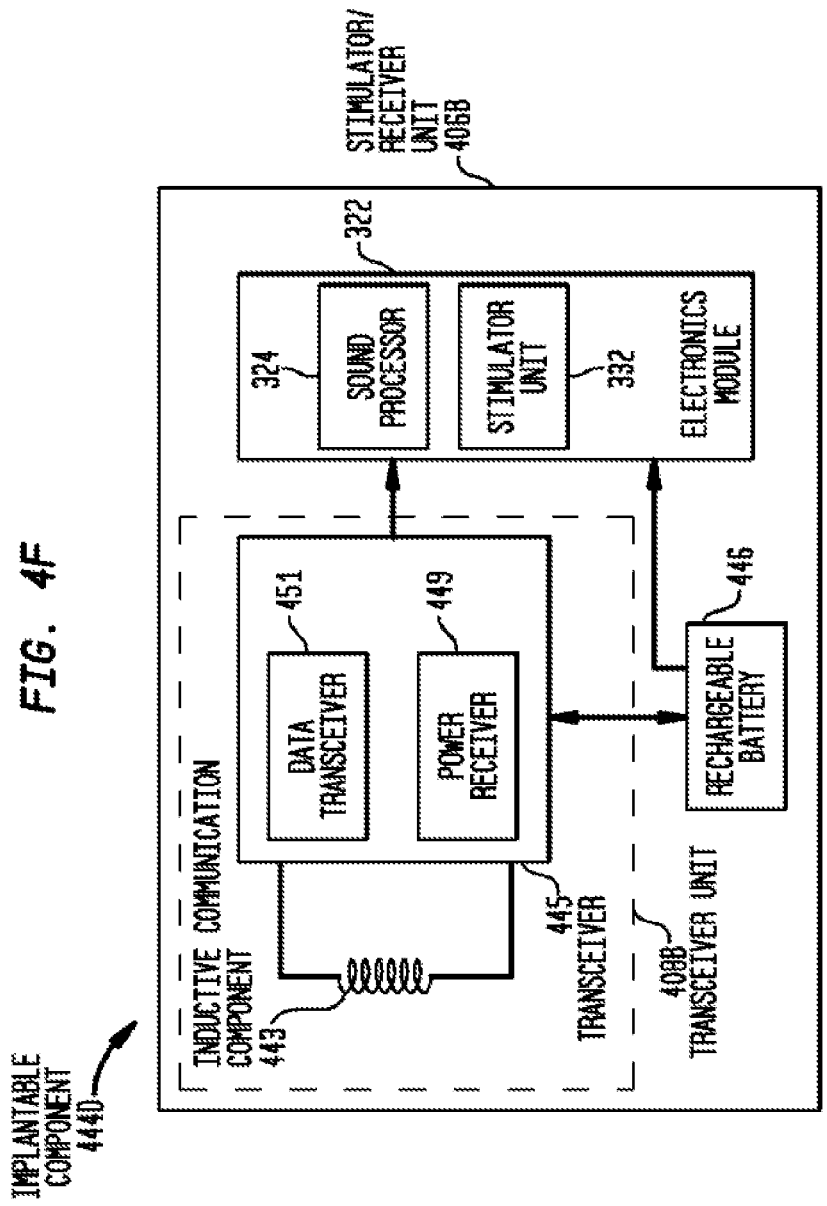
FIG. 4F is a simplified schematic diagram of a stimulator/receiver unit including a data transceiver and a communication component configured to vary the effective coil area of an implantable device in accordance with embodiments of the present invention.

FIGS. 4E and 4F depict alternate embodiments of the implantable components 444A and 444B depicted in FIGS. 4C and 4D, respectively. In FIGS. 4E and 4F, instead of coil 442, implantable components 444C and 444D (FIGS. 4E and 4F, respectively) include inductive communication component 443. Inductive communication component 443 is configured to vary the effective coil area of the component, and may be used in cochlear implants where the exterior device 304A/B does not include a communication component configured to vary the effective coil area (i.e., the exterior device utilizes a standard inductance coil). In other respects, the implantable components 444C and 444D are substantially the same as implantable components 444A and 444B. Note that in the embodiments depicted in FIGS. 4E and 4F, the implantable components 444C and 444D are depicted as including a sound processor 342. In other embodiments, the implantable components 444C and 444D may not include a sound processor 342.

FIG. 5 represents a high level conceptual exemplary magnetic coupling arrangement according to an exemplary embodiment. Specifically, FIG. 5 presents the magnet apparatus 160 of the implantable component 100 having a longitudinal axis 599 aligned with the magnet 560 of the external device 142, along with a functional representation of the tissue 504 of the recipient located between the two components. All other components of the external device and implantable component are not shown for purposes of clarity. As can be seen, the magnet apparatus 160 as a north-south polar axis aligned with the longitudinal axis 599, and magnet apparatus 560 also has a north-south polar axis aligned with the longitudinal axis of that magnet apparatus. In the exemplary embodiment, owing to the arrangements of the magnets, the resulting magnetic field aligns the magnets such that the longitudinal axes of the magnets are aligned. In an exemplary embodiment, because the various coils of the devices are aligned with the various longitudinal axes of the magnets, the alignment of the magnets aligns the coils.

Figure 6:
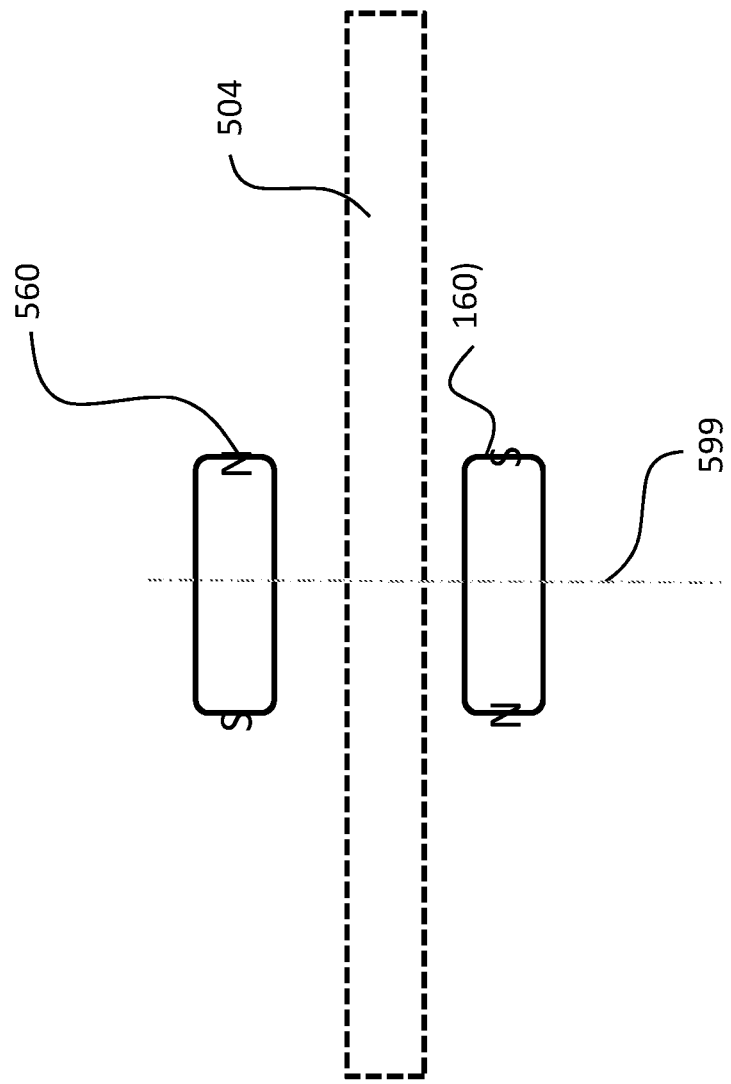
FIG. 6 is another exemplary conceptual schematic of a magnet system arrangement according to an exemplary embodiment.

FIG. 6 presents an alternative embodiment, where the magnet apparatus 160 of the implantable component 100 has a north-south axis aligned with the lateral axis of the magnet apparatus, as can be seen. In this exemplary embodiment, the magnet 560 also has a north-south axis also aligned with the lateral axis of that magnet.

As can be inferred from FIGS. 1B and 1C, the magnet apparatus of the implantable component 100 is a disk magnet apparatus/has the form of a short cylinder. The magnet of the external device 142 can also have such a form. That said, in an alternative embodiment, the magnets can have another configuration (e.g., a plate magnet, a bar magnet, etc.). Moreover, in an alternative embodiment, two or more magnets can be used in the implantable device and/or in the external device. The magnets could be located outboard of the coil. Any arrangement of magnet(s) of any configuration that can have utilitarian value according to the teachings detailed herein and/or variations thereof can be utilized in at least some embodiments.

Figure 7B:
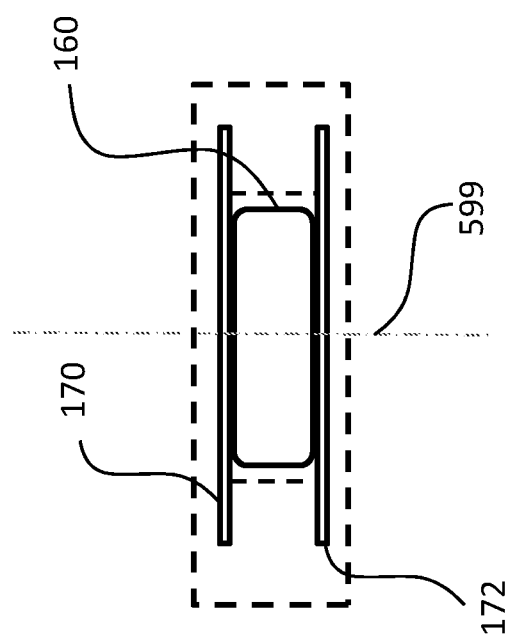

FIG. 7A presents a portion of the view of FIG. 1C (side view of FIG. 1B), showing the magnet apparatus 160 sandwiched by plates 170 and 172. All other components are removed for purposes of clarity. FIG. 7B depicts an rectangular-shaped dashed line structure, which conceptually represents a volume that is generally filled with an elastomeric material, such as silicone, thus conceptually representing the housing made from elastomeric material 199 of FIG. 1B. In an exemplary embodiment, the space is basically filled with silicone. That said, in an alternate embodiment, there are locations where there is no elastomeric material. FIG. 7B-7C present some examples, where the volume between the magnet apparatus 160 and the vertical dashed lines is devoid of silicone. (Note that these views represent only the sides of the magnet apparatus and housing with respect to the cross-section taken along the longitudinal axis of the implantable device 100—the elastomeric material can be closer to the magnet apparatus on the lateral sides/away from the longitudinal axis of the implantable device 100, thus still maintaining the position of the magnet apparatus 160.)

In an exemplary embodiment, the elastomeric material surrounding the plates holds the plates in place against the magnet. In this regard, with reference back to FIG. 7A, as can be seen, the plates 170 and 172 are located a distance D1 from each other. In an exemplary embodiment, distance D1 corresponds to the thickness of the magnet (as differentiated from the width of the magnet, which corresponds to the diameter of a disc magnet, which can be a disk magnet, as measured on a plane normal to the longitudinal axis 599). That is, in an exemplary embodiment, the plates are located in direct contact with the opposite faces of the magnet apparatus 160. In an exemplary embodiment where the opposite faces of the magnet apparatus are parallel, the surfaces of the plates 170 and 172 facing each other are also parallel, as those surfaces are also flat surfaces. It is briefly noted at this time that while the embodiments of the plates detailed herein are presented in terms of circular disks having uniform flat surfaces on either side thereof, in an alternate embodiment, the plates can be of different configurations, especially with respect to the surfaces thereof facing away from one another. Briefly, FIG. 7D depicts an exemplary alternate embodiment, where the upper plate 170D has a flat bottom surface, but a curved top surface. Note further that upper plate 170D has an outer diameter that is smaller than that of the bottom plate 172. Note also that the upper plate 170D is offset relative to the longitudinal axis 599 of the magnet apparatus 160. Any or all of these features can be utilized separately and/or together, on the upper plate and/or on the bottom plate. Additional details of the plates will be described below.

As noted above, the elastomeric material surrounding the plates holds the plates against the magnet apparatus 160. That is, in an exemplary embodiment, the housing made from elastomeric material 199 is arranged such that when the magnet apparatus 160 is located between the plates, the elastomeric material can impart a downwards and upwards force, respectively, onto the plate 170 and plate 172, thereby imparting a downward and upward force on to the opposite faces of the magnet apparatus 160. FIG. 8 represents a conceptual diagram of a force profile F1 applied by the resilience material of the housing to the plate 170 when the magnet apparatus 160 is located between the plates 170 and 172. In an exemplary embodiment, an equal and opposite force F1 is also present on the bottom surface of the plate 172. In an exemplary embodiment, this imparts a compressive force onto the magnet apparatus 160. That said, it is noted that in an alternate embodiment, the force profile F1 can corresponds to a zero force (in the absence of an external magnetic field). That is, an exemplary embodiment can entail a housing made of elastomeric material 199 that positions the plates 170 and 172 such that there is little to no compressive force onto the magnet apparatus 160. Still further, in an exemplary embodiment, there can be a gap between the magnet apparatus 160 and one or both of the plates 170 and 172, such that irrespective of the force profile F1 in the absence of an external magnetic field, no compressive force is applied to the magnet apparatus 160. That said, embodiments detailed herein will be presented in terms of a configuration where the housing made of elastomeric material 199 applies a compressive force through the plates onto the magnet apparatus 160 in the absence of an external magnetic field.

Figure 9:
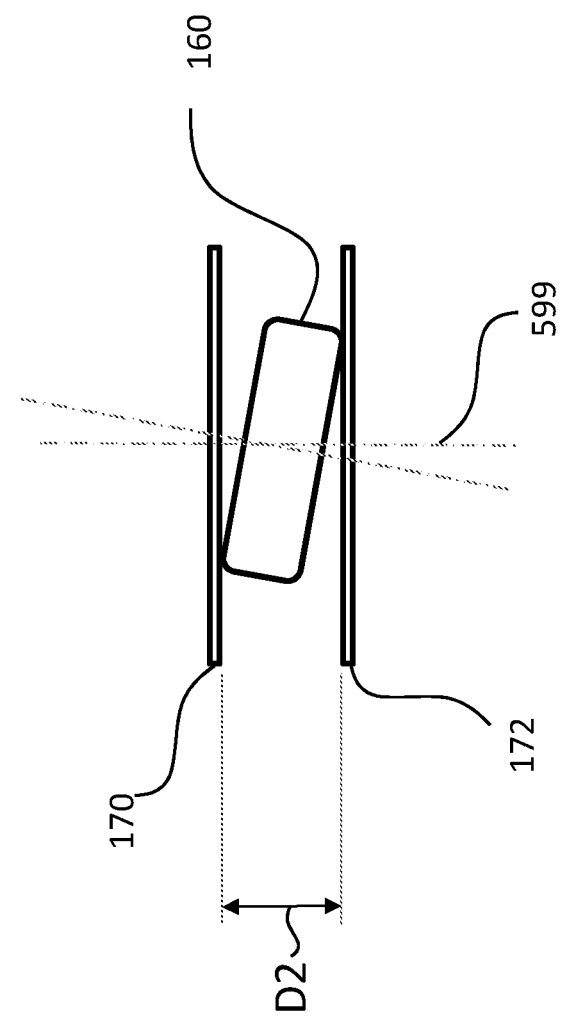
FIG. 9 depicts another functional schematic of an exemplary scenario resulting from use of an exemplary embodiment.

Referring now to FIG. 9, FIG. 9 depicts an exemplary scenario where an external magnetic field is applied to the magnet apparatus 160 while the magnet apparatus 160, and thus the implantable component 100, is implanted in a recipient at a location in the recipient corresponding to that which is where the implantable component would be implanted for normal use thereof (e.g., the magnet apparatus 160 can be located above the mastoid bone of the recipient and beneath the skin of the recipient for a cochlear implant). In an exemplary embodiment, the external magnetic field is that which results from an MRI machine during MRI imaging of the recipient's head (with the implantable component 100, and thus the magnet apparatus 160, implanted therein), where the magnetic field generated by the MRI machine interacts with the magnetic field of the magnet apparatus 160 to impart a significant torque onto the magnet apparatus 160. In an exemplary embodiment, the torque is up to 0.38 Newton meters, and the MRI machine applies a magnetic field such that the implanted magnet apparatus 160 is subjected to a 3 T magnetic field. The explanation below refers to a 3 T magnetic field, but is applicable to any applied field, such as by way of example only and not by way of example, a field of 0.2 T, 1.5 T, 3 T, 4 T, 5 T, 6 T and 7 T or more in some embodiments.

In an exemplary embodiment, the magnetic field is generated by a bore MRI machine. That said, in some embodiments, the magnetic field is generated by an open MRI. The teachings detailed herein are applicable to any MRI that imparts a magnetic field onto the magnet of the magnet apparatus 160 that imparts a torque onto the magnet.

As can be seen from FIG. 9, in an exemplary embodiment, the implantable component 100 is configured such that the plates 170 and 172 are pushed apart from one another due to rotation of the magnet apparatus 160 as a result of the torque applied thereto due to the 3 T magnetic field. As can be seen, the magnet apparatus 160 rotates such that its longitudinal axis moves from its normal position (the position where the magnet is located in the absence of an external magnetic field—as seen in FIGS. 7A and 8, where the longitudinal axis 599 of the magnet apparatus 160 is at least generally normal to the major surface of the plates). Owing to the rotation of the magnet 160, the magnet 160 is tilted between the plates 170 and 172. This is the result of pushing the plates 170 and 172 away from each other. This is represented by the distance D2 depicted in FIG. 9. As can be seen by visual inspection of FIG. 9 as compared to FIG. 7A, distance D2 is larger than distance D1. In an exemplary embodiment, distance D1 is 2.2 mm (corresponding to the thickness of the magnet 160, which can have a 12 mm diameter (width)). In an exemplary embodiment, distance D2 can be about 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm, 4.0 mm, 4.1 mm, 4.2 mm, 4.3 mm, 4.4 mm, 4.5 mm, 4.6 mm, 4.7 mm, 4.8 mm, 4.9 mm, 5.0 mm or more or any value or range of values therebetween in about 0.01 mm increments (e.g., about 2.44 mm to about 4.37 mm, 3.89 mm, etc.). Still further, in an exemplary embodiment, the difference between D2 and D1 (D2−D1) is about 0.01 mm, 0.1 mm, 0.2 mm, 0.3 mm, 0.4 mm 0.5 mm, 0.6 mm, 0.7 mm, 0.8 mm, 0.9 mm, 1.0 mm, 1.1 mm, 1.2 mm, 1.3 mm 1.4 mm, 1.5, mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm or more or any value or range of values therebetween in about 0.01 mm increments).

FIG. 9 shows the longitudinal axis 599 of the magnet 160 shifted from its normal position (599'). In an exemplary embodiment, shift from the normal position in degrees is about 5.0, 6.0, 7.0, 8.0, 9.0, 10.0, 11.0, 12.0, 13.0, 14.0, 15.0, 16.0, 17.0, 18.0, 19.0, 20.0, 21.0, 22.0, 23.0, 24.0, 25.0, 26.0, 27.0, 28.0, 29.0, 30.0, 31.0, 32.0, 33.0, 34.0, or 35.0 or more or any value or range of values therebetween in about 0.1 increments (e.g., about 11.3 to about 24.1 degrees, 15.3 degrees, etc.).

Figure 10:
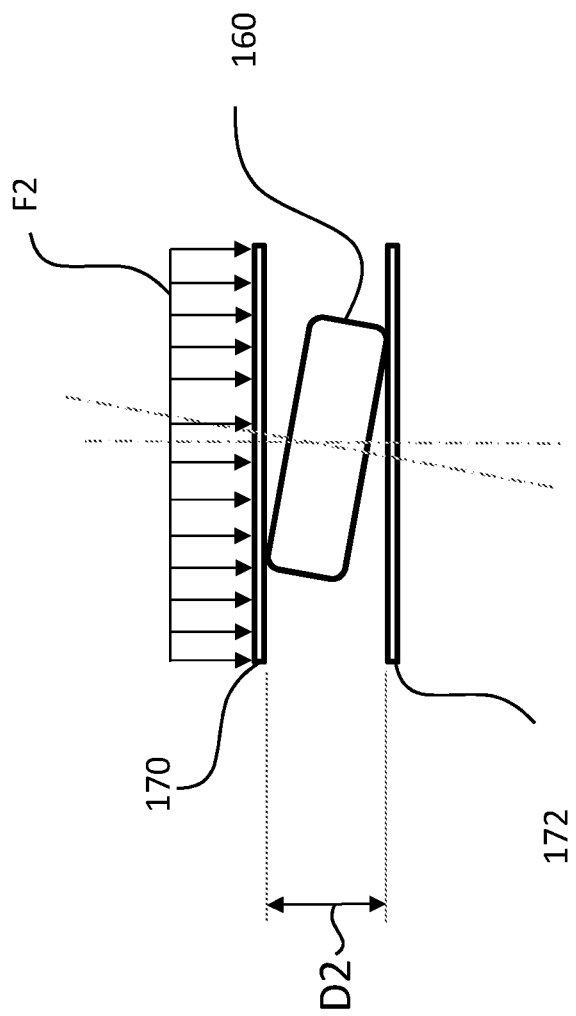
FIG. 10 depicts another functional schematic of an exemplary scenario resulting from use of an exemplary embodiment.

In an exemplary embodiment, owing to the housing made of elastomeric material 199, as the plates 170 and 172 are pushed apart from one another, the force applied to the outer surfaces of the plates by the material of the housing increases from the profile F1. The force on the outer surface of the plates will be considered in this explanation for clarity. It should be noted that the elastomeric material between the plates will exert a force on the inner surface of the plates. This force will act in the same direction as the force on the outside of the plates (i.e., toward the magnet). Hence, such can increase the effect described. In this regard, FIG. 10 presents a conceptual schematic representing a force profile F2 on the upper surface of the upper plate 170 resulting from the elastomeric material 199 having been stretched/displaced due to the expansion of the distance between the plates from D1 to D2, where, in an exemplary embodiment, an equal and opposite force profile is also located on the bottom surface of the bottom plate 172. The arrows of force profile F2 are presented longer than those of force profile F1 of FIG. 8, representing the fact that force profile F2 constitutes a larger force profile than that of FIG. 8.

Thus, in an exemplary embodiment, the increase in the distance between the plates increases the force profile on those plates imparted by the material of the housing. This increase in the force profile on the plates is in turn applied to the magnet 160 by the plates, as magnet 160 contacts the plates 170 and 172 (directly or indirectly, as will be described in greater detail below). The increase in the force profile counteracts the torque applied to the magnet 160 due to the 3 T magnetic field of the MRI machine. When the forces resulting from the torque applied to the magnet 160 are in equilibrium with the resulting force profile applied to the plates due to deformation of the elastomeric material of the housing, further rotation of the magnet 160 is prevented.

Figure 11:
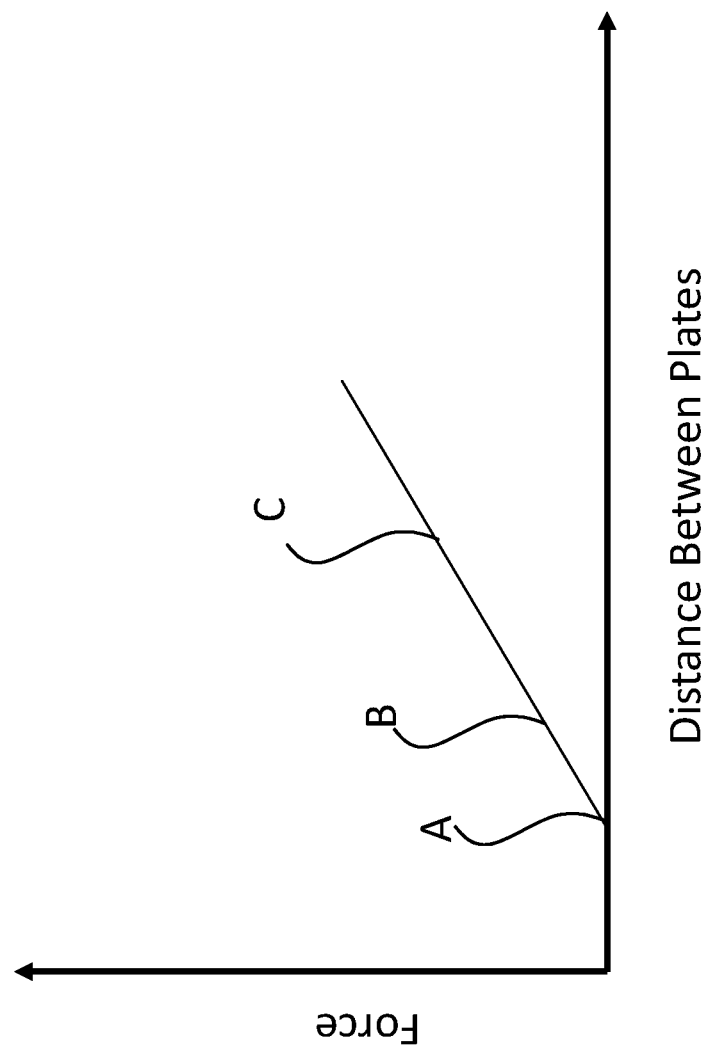
FIGS. 11-13 depict exemplary conceptual data charts according to an exemplary embodiment relating force to distance between plates.
Figure 12:
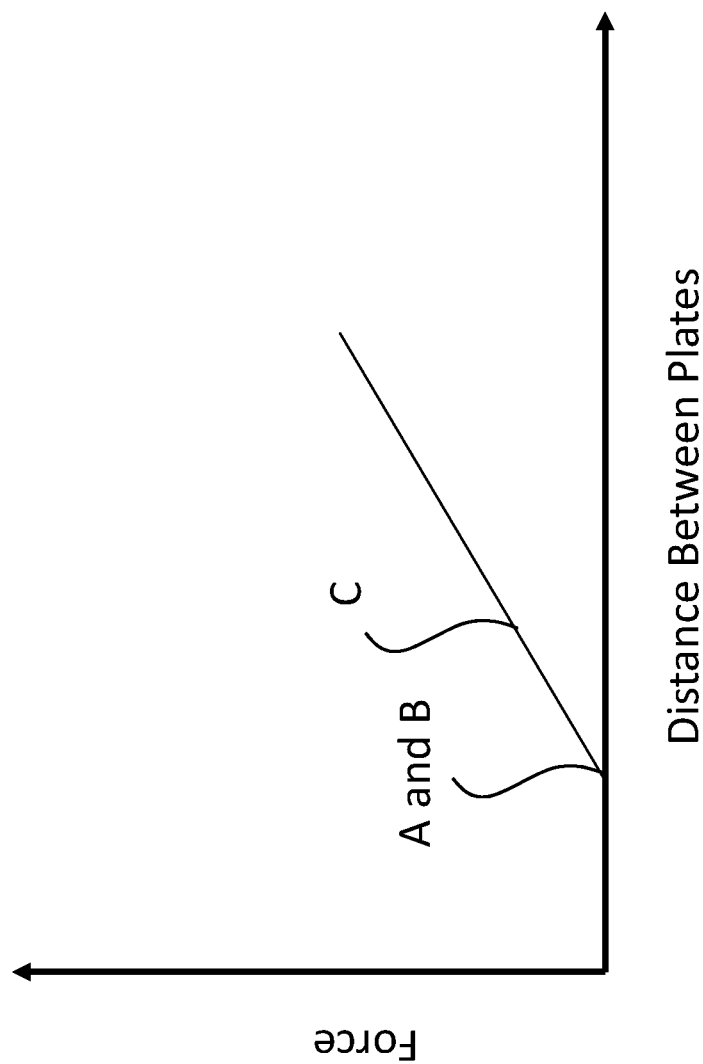
Figure 13:
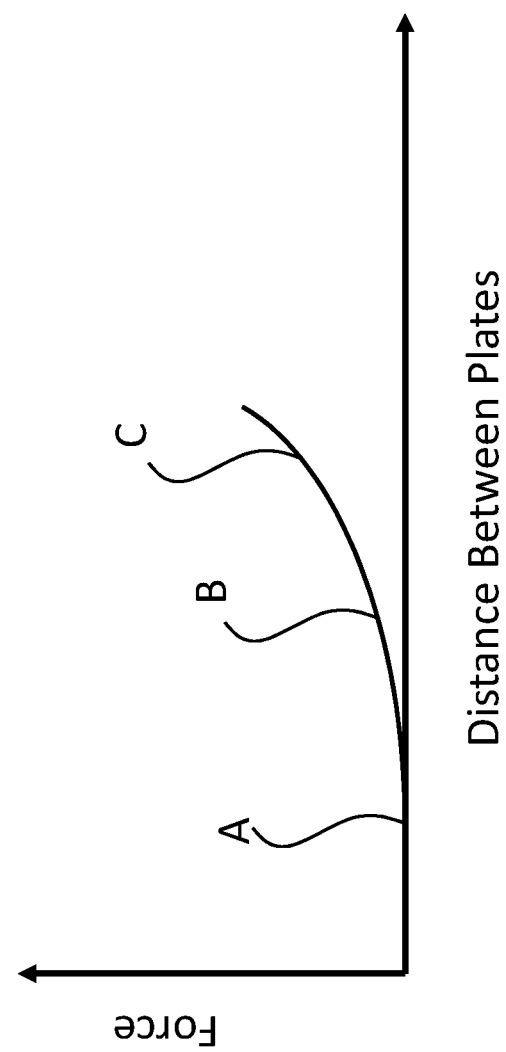

FIG. 11 provides an exemplary conceptual chart presenting a force (force on the plates) versus distance between plates curve, where point A corresponds to the location of the plates in a relaxed state (e.g., without magnet 160 located there between), point B corresponds to the force resulting from the magnet being located between the plates in the normal location without an external magnetic field (the force profile F1, where the magnet 160 itself pushes the plates away from each other), and point C representing the maximum plate separation resulting from the 3 T magnetic field. As can be seen, in the exemplary embodiment, the increase in forces is linear. FIG. 12 presents a force versus distance between plate curve for an alternate embodiment, where points A and B are located at the same location (the location of the plates in the relaxed state is the same with or without the magnet 160 being located therebetween—the plates provide a negligible, if not no force onto the magnet in the absence of an external magnetic field). As with the chart of FIG. 11, the curve is linear. FIG. 13 presents an alternate embodiment where the force is nonlinear with respect to the distance between the plates. It is noted that these charts are but examples with respect to force versus distance between plates curves. Other configurations of exemplary embodiments will result in other curves. Any relationship between force and distance between plates that will enable the teachings detailed herein and/or variations thereof to be practiced can be utilized in at least some embodiments.

An exemplary principle of operation of some exemplary embodiments will now be described in conceptual terms. It is noted that these principle of operations are but exemplary, and to the extent that embodiments can be practiced utilizing the teachings detailed herein and/or variations thereof that results in other principles of operations being utilized in a manner having utilitarian value, such other principles of operations can also be utilized to implement the teachings detailed herein. That said, FIG. 14 presents an exemplary conceptual arrangement with the plates 170 and 172 and the magnet 160 located in a conceptual housing 1499 made of elastomeric material having wall thicknesses T1 and T2 as seen, where the magnet 160 is not exposed to an external magnetic field. In some exemplary embodiments, the conceptual housing 1499 applies a compressive force onto the magnet through the plates 170 and 172 in the absence of an external magnetic field. In some exemplary embodiments, the conceptual housing 1499 does not apply compressive force onto the magnet through the plates in the absence of an external magnetic field. FIG. 15 represents the magnet 160 being subjected to an external magnetic field of 3 T, where the magnet 160 has rotated due to the torque applied thereto resulting from the magnetic field. As can be seen, the wall thicknesses of the housing 1499, T1' and T2', are thinner than that of T1 and T2 of FIG. 14, owing to the fact that the plates 170 and 172 have been a pushed away from one another relative to that which was the case in FIG. 14 owing to the torque applied to the magnet 160. In essence, the housing has stretched, or, more accurately, the elastomeric material of the housing 1499 has stretched. Because the elastomeric material of the housing has a memory such that the housing 1499 seeks to return to the state at which it was in in FIG. 14 (with the wall thickness returning to T1 and T2, or at least to something close to T1 and T2 and/or less than T1' and T2', the force profile F2 is developed on the plates as detailed above, thus countering further rotation of the magnet. By way of example only and not by way of limitation, the effect of the housing 1499 on the plates 170 and 172 can be considered analogous to the principle of operation of a rubber band. In this regard, the elastomeric material of the housing 1499 imparts a compressive force onto the plates 170 and 172, where the compressive force increases with increased separation of the plates from each other due to the rotation of the magnet 160.

In an exemplary embodiment, the elastomeric material utilized to fabricate the housing is made of silicone MED4860 (from Nusil). In an exemplary embodiment, T1 is about 0.3 mm (which also includes 0.3 mm—all uses of about and substantially and other qualifiers also include the exact amount unless otherwise specified), and the maximum thickness of the housing, as measured parallel to the longitudinal axis of the magnet 599 at any location above and below the plates, is about 4 mm (which includes 4 mm or less).

It is noted that FIGS. 14 and 15 are simply conceptual figures. It is noted that the thicknesses are depicted as changing by an exaggerated amount. Moreover, it is possible that in at least some embodiments, the thickness T2 may not change and/or may change less than the thickness T1 (by ratio and/or in total), and/or vice versa.

Figure 16A:
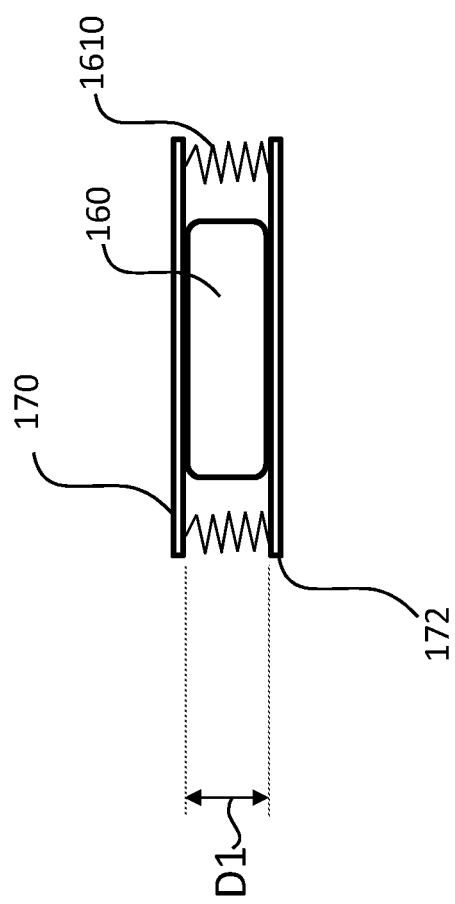

FIG. 16A represents an alternate embodiment that utilizes components located between the plates 170 and 172 to provide a reaction force against the rotation of the magnet 160, more specifically, the embodiment of FIG. 16A includes resilient components/elastomeric components 1610 located outboard of the magnet 160 between the plates 170 and 172. In the embodiments of FIG. 16A, resilient component 1610 is presented as springs extending from the bottom plate 172 to the top plate 170. In an alternative embodiment, these can be pillars of silicone adhered to the surfaces of the plates. The pillars (springs or resilient components) can be arrayed uniformly (or non-uniformly) about the magnet. The number of resilient component 1610 can correspond to any number that can enable the teachings detailed herein and/or variations thereof to be practiced. Still further, in an exemplary embodiment, the resilient component 1610 can be a ring or a partial ring about magnet 160. That is, the resilient component 1610 can be a single component. Any device, system, and/or method that can provide tensile force between the plates 1720 and 1722 that can enable the teachings detailed herein and/or variations thereof to be practiced, can be utilized in at least some embodiments.

It is noted that some exemplary embodiments can be practiced without utilizing an elastomeric material to interact with or otherwise provide reactive force on the plates, or at least without utilizing an elastomeric material that makes up the housing or the like of the implant 100. The plates can be attached rigidly at a number of locations around the edge thereof. By way of example, in effect, the plate provides the rigid component and the spring component providing the restoring force.

Further, by way of example only and not by way of limitation, utilizing as a basis for discussion the device of FIG. 16A, with reference now to FIG. 16B, it can be seen that the magnet apparatus 160 and the plates 170 and 172 and the springs 1610 are located in a housing 1669. In this exemplary embodiment, the housing 1669 is a housing that also encompasses stimulator unit 122, while in other embodiments, the housing does not encompass stimulator unit 122 and/or only encompasses the plates, the magnet apparatus and the associated components. The embodiment of FIG. 16B is depicted as having a housing 1669 including the stimulator unit 122 as that will provide a larger footprint/area to react against any torque induced into the system. Any housing arrangement that will enable the teachings detailed herein and/or variations thereof to be practiced can be utilized in at least some embodiments.

In an exemplary embodiment, the housing 1669 is a rigid housing (e.g., it can have a rigidity of that of the plates or more or less). Additional details of this will be described below. As can be seen in FIG. 16B, there are two rails that extend from the bottom portion of the housing 1669 to the top portion of the housing 1669, which rails extends through plates 170 and 172. In an exemplary embodiment, the arrangement is such that the relationship between the rails 1655 and the plates is such that the plates move with translational motion along the rails 1655 and cannot substantially move (e.g., rotate) to a position where they are no longer parallel to each other. This can be achieved via close-fitting holes through the plates relative to the rails 1655. Alternatively and/or in addition to this, extension tubes can be located on the plates in a manner that provides additional reaction torque against any rotation of the plates. Here, the springs 1610 provide a reaction force against the plates 170 and 172, moving away from each other, or at least plate 170 moving away from plate 172 in the case where plate 172 is fixed to the bottom surface of the housing 1669, in the presence of a magnetic field that imparts a torque onto the magnet apparatus 160. The plates operate, in at least some embodiments, according to the same general principles detailed herein, except that instead of utilizing the elastomeric material of the housing to provide a force against the plates moving away from each other, the housing does not provide a force against the plates, but instead the springs 1610 provides the entire force. In an exemplary embodiment, there is utilitarian value with respect utilizing a rigid housing in the sense that the rigid housing can hold the rails 1655 in a proper position/properly aligned so that the system can operate in accordance to the principles detailed herein.

It is noted that in an alternate embodiment, compression springs instead of or in addition to the extension springs can be utilized. The compression springs can be located between the plate(s) and the housing 1669 wall(s).

Figure 16C:
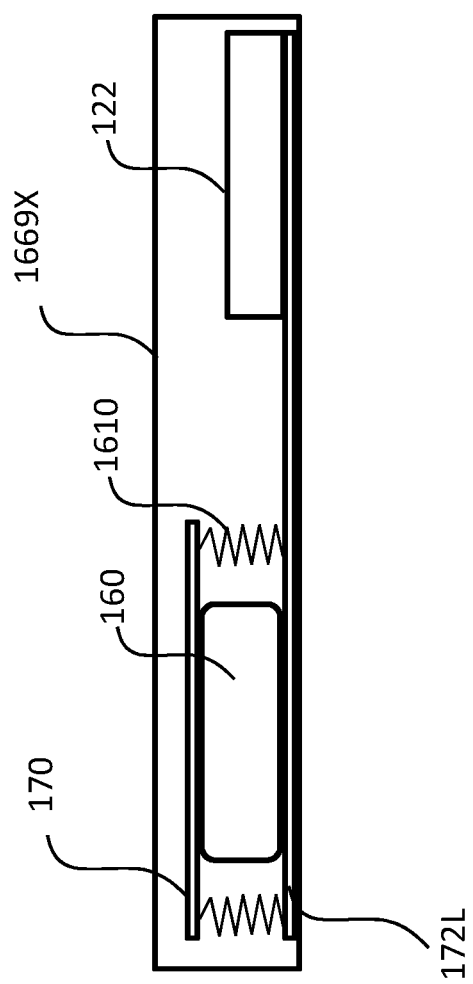

FIG. 16C depicts an alternate embodiment utilizing concepts similar to those of FIG. 16B. In this regard, a plate 172L is utilized that extends from the stimulator unit 122 to the magnet apparatus 160. In this exemplary embodiment, the length of the plate 172L provides sufficient reaction against any torque imparted into the system resulting from the magnetic field applied to the magnet apparatus 160. Housing 1669X is presented as being a rigid housing concomitant with housing 1660 of FIG. 16B. However, in alternate embodiments, housing 1669X can be a housing made of an elastomeric material. In such an exemplary embodiment, according to an exemplary embodiment thereof, there is sufficient space provided for the plate 170 to move accordingly. That said, in an alternate embodiment, the elastomeric material can act in combination with the springs 1610.

Figure 16D:
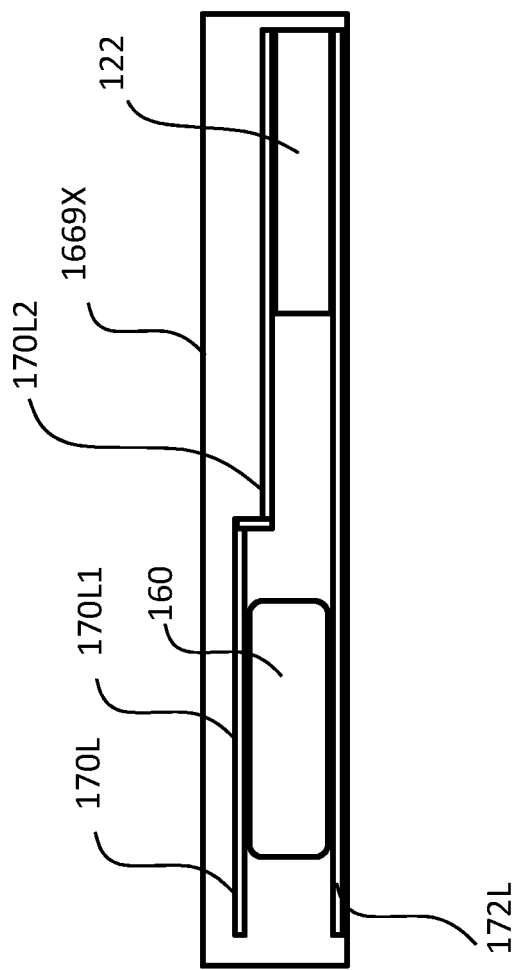

FIG. 16D presents an alternate embodiment utilizing concepts similar to those of FIG. 16B. Here, the system utilizes a long plate 170L on the top and a long plate 172L on the bottom. These plates extend from the stimulator unit 122 to the magnet apparatus 160 as can be seen. In an exemplary embodiment, owing to the fact that the plates have a modicum of resiliency over the long span owing to their length, while having localized rigidity in the locations proximate to the magnet apparatus 160, the arrangement of FIG. 16D can be used to practice the principles detailed herein and/or variations thereof. While it will be understood that the configuration of 16D may not result in the plates being parallel to each other in some instances, in an exemplary embodiment, plate 170L can be a composite plate such that the portion that interfaces with magnet 160, is permitted to rotate relative to the other portions of plate 170L when the plates separate from each other owing to the torque applied to the magnet apparatus 160, so that the portion that interfaces with magnet 160 remains parallel. In an exemplary embodiment, portion 170L1 can be hinged to portion 170L2, and an arrangement can be provided that imparts a force onto 170L1 as the plates are pushed apart to force the portion 170L1 to remain at least generally parallel to 170L. Again, housing 1669X can be a rigid housing or a flexible housing.

Any arrangement that can enable the teachings detailed herein and/or variations thereof to be practiced can be utilized in at least some embodiments.

In this regard, the plates have been shown flat even when under load such as in FIG. 15. Some embodiments utilize plates which have some compliance so the plates bend to a limited extent when under load. In some embodiments, this will put the plate in tension such that there is a restoring force tending to make the plate substantially flat again. This unbending force from the plate will add to the force on the magnet apparatus.

In view of the above, it will be understood that in an exemplary embodiment, there is an implantable medical device, such as a cochlear implant, or any other type of medical device that utilizes an implantable magnet (irrespective of what the implantable magnet is used for/irrespective of whether or not the implantable magnet is utilized to retain an external component to the recipient), comprising a magnet apparatus, such as magnet 160 detailed above by itself or encased in a housing (e.g., a titanium housing) and/or coated in a biocompatible material, and a body (e.g., body 199/housing conceptually represented by element 1499 as detailed above) encompassing the magnet, the body made of an elastomeric material, such as silicone (biocompatible/implantable), rubber (biocompatible/implantable rubber), or incorporating resilient elements (e.g. springs) as part of the housing or any other material, such as a polymer body that will enable the teachings detailed herein and/or variations thereof. The implantable medical device resists rotation of the magnet relative to the body in at least one plane when subjected to an externally generated magnetic field due to a component (e.g., one or both of the plates 170 and 172) relative to which the magnet apparatus is slidable, wherein the component located within the body.

It is noted that by slidable, this means that the magnet changes a global position relative to the component. This as contrasted to the magnet revolving/spinning relative to the plates, where the magnet is in the same position, except that points on the magnet's surface are at a different location. By analogy, a car tire can slide on ice when the car tire moves location. A car tire spinning on the ice is not sliding across the ice.

In an exemplary embodiment, the medical device includes a plurality of separate structural components (e.g., plates 170 and 172) of greater rigidity than the body/material of the body, at least partially embedded in the body, wherein one of the plurality of structural components corresponds to the component relative to which the magnet apparatus slides, and wherein the structural components resists rotation of the magnet apparatus within the body, as detailed above (which resistance is achieved through interaction between the plates and the magnet apparatus). In an exemplary embodiment, the medical device includes a first structural component and a second structural component (again, plates 170 and 172), where the first and second structural components collectively are sandwiching the magnet apparatus, wherein the structural components resist rotation of the magnet apparatus in at least one plane within the body. In this regard, in an exemplary embodiment, the structural components resist rotation of the magnet apparatus in the plane used for the cross-sectional view shown in FIGS. 7A, 8, 9, etc. That is, a plane on which the longitudinal axis of the magnet 160 lies.

In an exemplary embodiment, the plates are about ½, 1, 1.5, 2 or 3 or more orders of magnitude more rigid than the body. By way of example only and not by way of limitation, silicone has a young's modulus of 0.001 to 0.05 GPa while PEEK has a young's modulus of 3.6 GPa.

By "resists rotation," as detailed herein the medical device is configured to permit a modicum of rotation of the magnet apparatus. Indeed, in at least some exemplary embodiments, some initial rotation is required so as to push the plates apart thereby creating the above-detailed force F2, so as to resist further rotation. Accordingly, in an exemplary embodiment, the first and second plates, which are separate from one another, are arranged such that the magnet apparatus is restrained from rotating beyond an initial amount within the body by the first and second plates, this being encompassed by the configuration that resists rotation as detailed herein.

Note further that in an exemplary embodiment of this exemplary embodiment, the magnet alone and/or the magnet coated with another material and/or the magnet located in a container making up the magnet apparatus can revolve relative to the longitudinal axis thereof. Accordingly, in an exemplary embodiment, the medical device is configured to not resist revolution of the magnet apparatus and/or the magnet, at least about one axis.

It is further noted that in an exemplary embodiment, the medical device is configured to resist movement of the magnet apparatus in all three directions of the Cartesian coordinate system. That said, in an alternate embodiment, the medical device is configured to resist movement of the magnet apparatus in only one or two directions of the Cartesian coordinate system. Corollary to this is that in an exemplary embodiment, the medical device is configured to resist rotation of the magnet apparatus about all three directions of the Cartesian coordinate system. That said, in an alternate embodiment, the medical device is configured to resist rotation of the magnet apparatus about only one or two directions of the Cartesian coordinate system.

Still further, as seen in FIG. 7A, the magnet apparatus has a width and height (e.g., the width is the long axis (largest diameter) of a circular magnet, and the height is the short axis of the circular magnet), wherein the height is less than the width, and the first plate 170 is located on a top side of the magnet apparatus, and the second plate 172 is located on a bottom side of the magnet apparatus opposite the top side, wherein the plates extend in a direction normal to the direction of the height (normal to the direction of the longitudinal axis of the magnet).

Corollary to this is that in an exemplary embodiment, the plates have a width and a height, wherein the height is less than the width, the width of the plates is greater than the width of the magnet apparatus, and the width of the plates is at least about parallel to the width of the magnet apparatus (consistent with FIG. 7A). As can be seen in the figures, one or both of the plates can extend past outer peripheries of the magnet apparatus with respect to a direction parallel to the width of the magnet apparatus.

In view of FIGS. 7B and 7C and 16, in an exemplary embodiment, an elastomeric material is located at opposite locations relative to the height direction of the magnet apparatus, and the elastomeric material that is located at opposite locations is located between the first plate and the second plate relative to the direction of extension of the height of the magnet apparatus. In an exemplary embodiment, the aforementioned elastomeric material can correspond to the elastomeric material of the body encompassing the plates (the housing 199). In an exemplary embodiment, the aforementioned elastomeric material can correspond to material separate from the material of the body (spring material, separate silicone where the body is also silicone, springiness built into the plates, etc.).

In an exemplary embodiment, the elastomeric material of the body (housing 199) resists movement of the first plate away from the second plate due to rotational torque applied to the magnet apparatus by the external magnetic field, thereby resisting rotation of the magnet apparatus. Again, the term "resists" encompasses a modicum of movement of the plates away from one another (and note that movement of the first plate away from the second plate also includes movement of the second plate away from the first plate as well, providing that there is movement of the first plate away from the second plate).

Figure 18A:
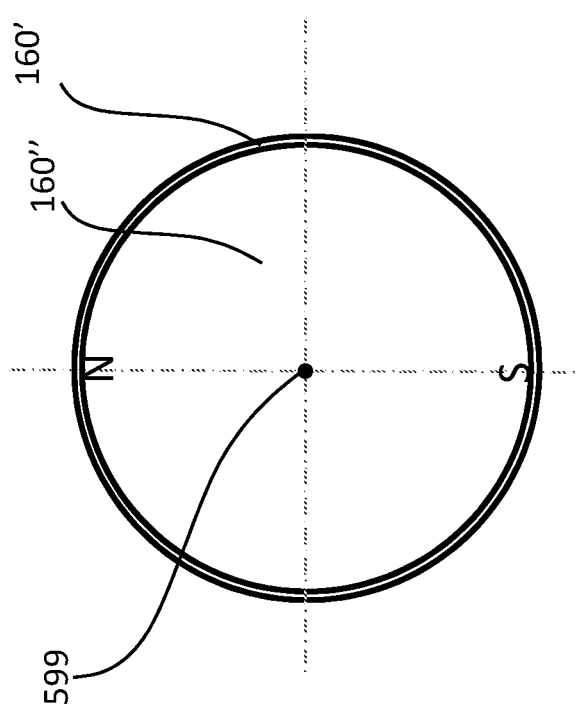
FIG. 18A represents an exemplary conceptual schematic of an assembly according to an exemplary embodiment.
Figure 18B:
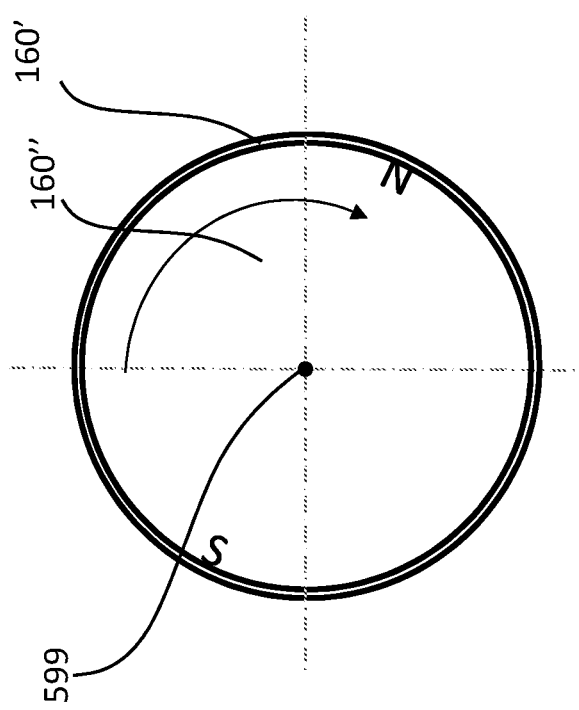
FIG. 18B and FIG. 18C, represent an exemplary scenarios of conceptual use according to an exemplary embodiment.
Figure 18C:
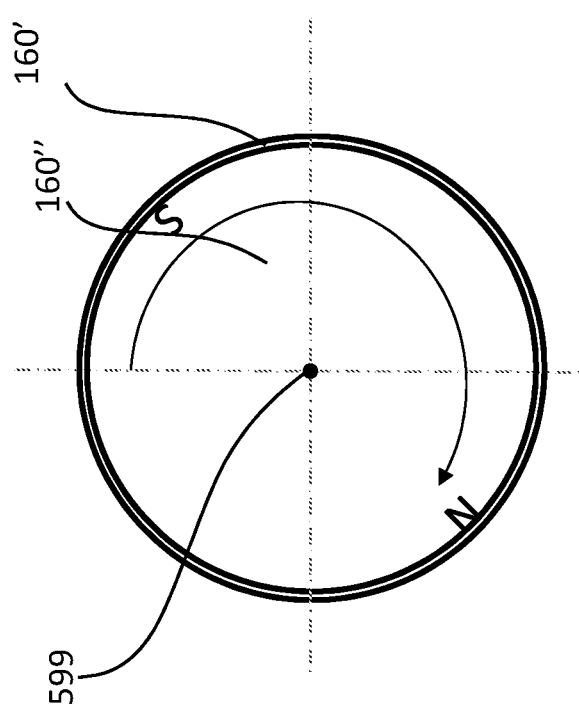

As noted above, in an exemplary embodiment, the magnet apparatus comprises a magnet located in a container, wherein the magnet is free to revolve relative to the container. FIG. 17 provides an exemplary schematic of such an exemplary environment, depicting magnet apparatus 160 (and, accordingly, any disclosure herein of magnet 160 corresponds to a disclosure of magnet apparatus of FIG. 17), including container 160' and magnet 160". FIG. 17 depicts magnet 160" subjected to an external magnetic field that imparts a torque thereon about an axis normal to the longitudinal axis 599 of the magnet 160", the torque represented by arrow 17T, causing the magnet to rotate about the axis normal to the longitudinal axis 599 of the magnet. The torque 17T depicted in FIG. 17 may represent the entire torque imparted on the magnet 160" by the external magnetic field or the component of the entire torque that causes the magnet to rotate—i.e. the component of the imparted torque that is centered about an axis normal to the longitudinal axis 599 of the magnet 160". The rotation of the magnet 160" is limited by the inner walls of container 160', and the torque applied to the container 160' by the magnet 160" is opposed by the plates as detailed herein, which are not shown in FIG. 17, but the function thereof is represented by arrows 17A and 17B, which applies the counter torque to the magnet, thereby resisting the torque 17T. However, the magnet 160" is configured to revolve about a longitudinal axis 599, even though the magnet is restrained from rotating beyond that permitted by the plate/housing assembly. In this regard, FIGS. 18A-18C depict an exemplary revolution of magnet 160" within container 160', where the container 160' remains stationary in each of the FIGS., but the magnet 160" revolves about axis 599. It is further noted that in this exemplary embodiment, the magnet 160" is a magnet having the north-south pole on the lateral sides of the magnet (i.e., the pole is aligned normal to the longitudinal axis 599). In an exemplary alternative embodiment, the magnet 160" can be a magnet having the north-south pole axis aligned with the longitudinal axis.

Accordingly, in an exemplary embodiment, the magnet apparatus comprises a magnet 160" located in a container 160', wherein the magnet is free to revolve relative to the container.

In an exemplary embodiment, the elastomeric material of the body extends around a majority of a circumference of the container in face to face relationship with the circumference of the container. By "face to face relationship," it is meant that there is no other component of the implantable component 100 in between the elastomeric material and the container, such as a chassis or the like. In an exemplary embodiment, the silicone of the silicone body extends completely around the magnet apparatus in face to face relationship with the circumference of the magnet apparatus.

It is noted that in an exemplary embodiment, the container can include a low friction coating such as PTFE and/or a lubricant, such as an oil or the like, that reduces friction between the magnet 160" and the inner surface of the container 160'. Alternatively or in addition to this, the magnet apparatus 160 can utilize ball bearings or an axle with bushes, or the like. Indeed, in an exemplary embodiment, this can prevent substantially all (including all) rotation of the magnet 160" relative to the container 160', while permitting the magnet 160" to revolve relative to the container 160'. FIG. 19 depicts such an exemplary embodiment.

Figure 20:
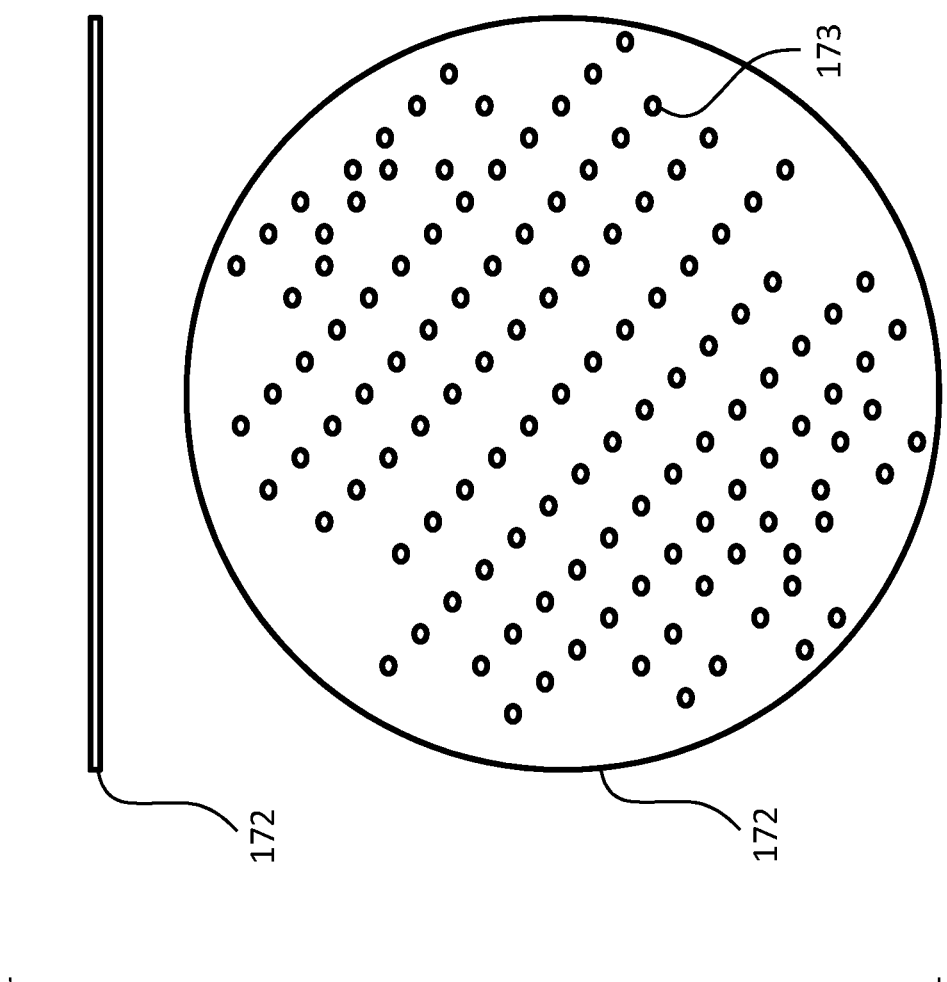
FIGS. 20-23E variously represent various exemplary conceptual schematics of various exemplary assemblies according to various exemplary embodiments.

FIG. 20 depicts an exemplary embodiment of a plate 172, depicting a side view (top) and a top view (bottom). As can be seen, in an exemplary embodiment, the plate 172 has holes 173 into which the silicone material of the body (housing) can enter, thereby interlocking the elastomeric material with the plate. The configuration of plate 172 of FIG. 20 can be used as plate 170 as well.

It is noted that while in some embodiments, the holes 173 extend completely through the plate 172, in an alternate embodiment, the holes 173 only extended a portion of the way through the plate 172, so as to preserve a smooth surface on one side of the plate (e.g., the side facing the magnet). Still further by way of example, the holes 173 can be dovetailed or the like, so that the elastomeric material, during a molding process, can flow into the holes and then be quasi trapped therein. It is noted that while the embodiment of FIG. 20 presents an abundance of holes 173, alternate embodiments may utilize fewer holes 173. Alternatively, some embodiments may utilize more holes than those depicted in FIG. 20.

Note further that while the arrangement of holes 173 depicted in FIG. 20 corresponds to an array of holes located across the entire surface of the plate 172, in some alternate embodiments, the holes are more specifically located. In an exemplary embodiment, the holes can be arrayed about the outer periphery of the plate 172. This can have utilitarian value in embodiments where, for example, the holes 173 extend all the way through the plate 172, and it is desired to have a smooth surface at locations inboard of the holes along which the magnet apparatus will slide relative to the plate. Corollary to this is that there can instead be utilitarian value to having the holes 173 located in the center portion of the plates, where the tips of the magnet apparatuses do not reach because the rotation thereof is limited. Indeed, in an exemplary embodiment, this can permit maximum stretchability of the elastomeric material about the plates, because the elastomeric material is only anchored to the plates at the center. That said, in some embodiments, such may not have utilitarian value, and the former arrangement can be applied so as to permit minimum stretchability of the elastomeric material about the plates (because the elastomeric material is anchored to the plates about the periphery). Alternatively, combinations can exist where the holes on the outer periphery extend all the way through the plate, and the holes inboard thereof only extend a portion of the way through the plate, or visa-versa, etc.

Figure 21:
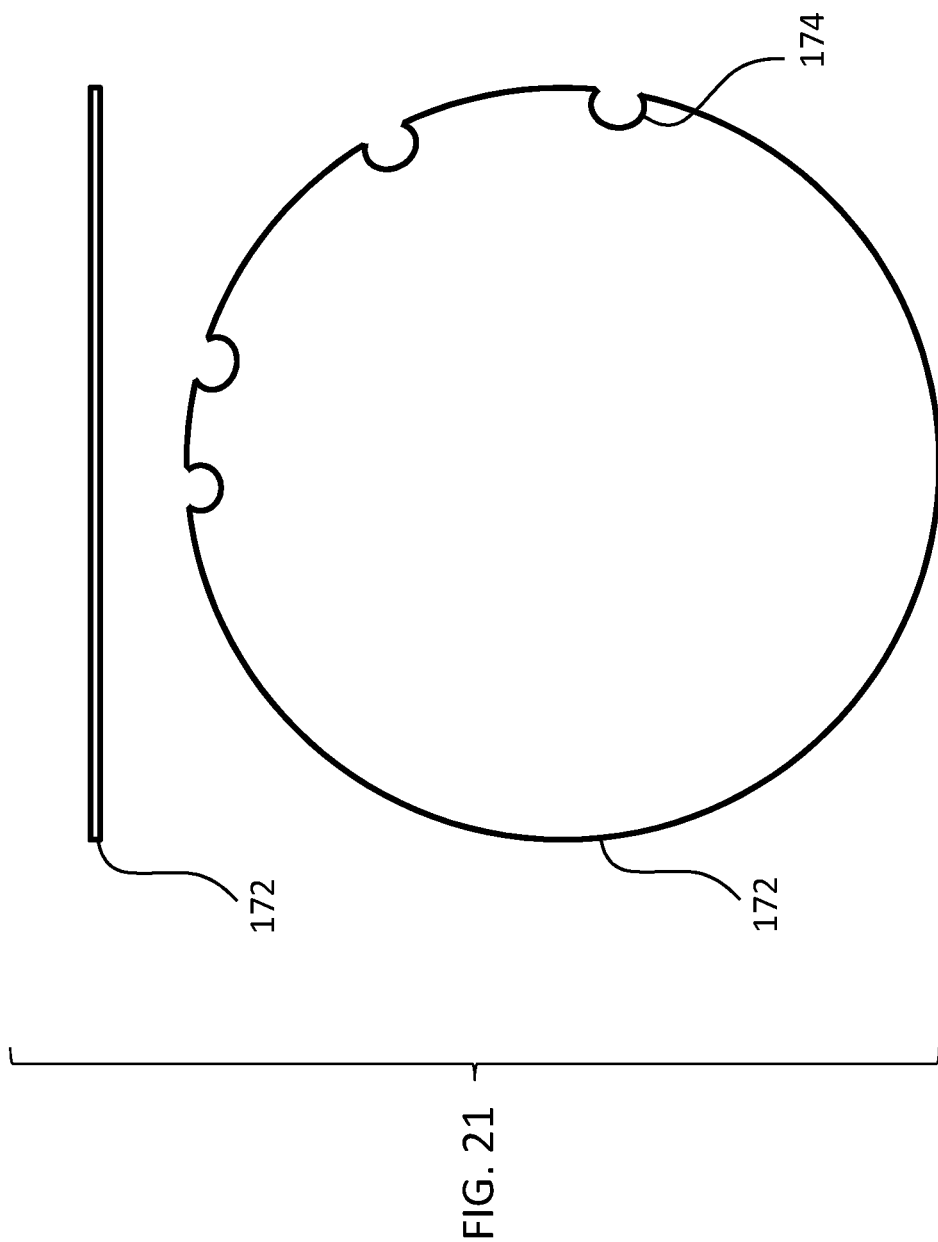

Note further that the holes do not have to be completely surrounded holes, as seen in FIG. 21, where holes 174 are arrayed about the periphery (not all holes are depicted).

Any combination of holes that can enable the teachings detailed herein and/or variations thereof to be practiced can be utilized in at least some exemplary embodiments. This includes by way of example and not by way of limitation, tracks, channels or notches formed in the outward facing surface of the plate(s) with a dovetail groove or overhang that mechanically engages with the elastomeric housing.

In an exemplary embodiment, the plates can be made of PEEK, and can have a 0.3 mm thickness (the dimension of the top reproduction of 172 in FIG. 20) and a spanwise diameter (the dimension of the bottom reproduction of 172 in FIG. 20) of 19 mm. Larger or smaller plates can be utilized. For example, the plates can have a thickness ranging from 0.1 mm to 0.5 mm, 0.2 mm to 0.4 mm or 0.25 to 0.35 mm and a spanwise diameter ranging from 15 mm to 24 mm, 16 mm to 23 mm or 17 mm to 21 mm. Still further, while the embodiments depicted in the FIGS. depict circular plates, alternative embodiments can utilize plates having oval shaped or generally rectangular (including square) shaped plates (with respect to the view looking at the surface facing towards or away from the magnet apparatus). Also, plates having complex boundaries can be utilized (star shapes, combination of rectangular and circular shapes, etc.). Indeed, the shapes of the plates can be tailored to achieve a given performance feature, as the shape of the plate will impact the resistance to separation of the plates away from one another for a given torque applied to a given magnet, all other things being equal. Still further, the bottom plate can be of a different configuration than the top plate.

In an exemplary embodiment, the plates can be made of any nonmagnetic material. Still further, and an exemplary embodiment, the plates can be made of any material that is conducive to the transfer of the magnetic flux generated by the magnet of the magnet apparatus 160 through the plates. Still further, any material or configuration of the plates that is conducive to the use of the coils 137 can be utilized.

In an exemplary embodiment, the plates are made from PTFE, PPSU, ceramic, or other materials or combinations of these materials. It is further noted that in an exemplary embodiment, the elastomeric body is molded about the plates. Thus, in an exemplary embodiment, the implantable component 100 is configured such that the plates are not removable from the body except in a scenario where the body is purposely being destroyed.

Figure 22:
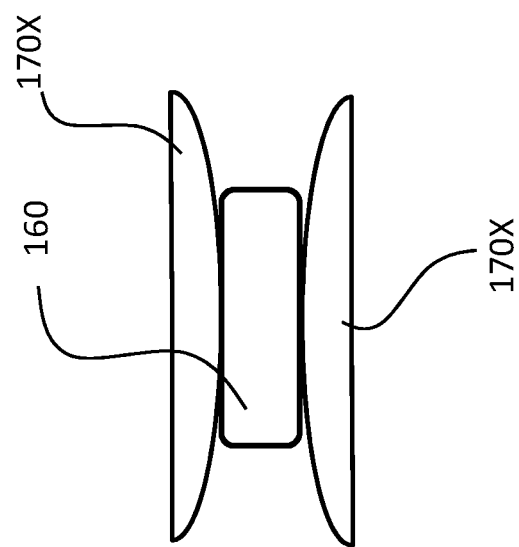

As noted above, the plates do not have to have parallel surfaces. While in some embodiments, the surface facing the magnet can be a flat surface, in other embodiments, the surface facing the magnet can be curved. Indeed, in an exemplary embodiment, curvature can be utilized to achieve a nonlinear "force" to "distance between plates" curve irrespective of the material properties of the elastomeric material utilized with the plates. Such an exemplary embodiment is seen in FIG. 22, where plates 170X are utilized. In an exemplary embodiment, because of the curved surfaces of plates 170X, the more that the magnet 160 rotates, the resistance to the rotation thereof owing to the curvature of the surface increases in a non-linear manner for a given plate separation.

In an exemplary embodiment, a flat surface is utilized on one of the bottom or top plates, so as to provide stability to the magnet (e.g., to reduce any tendencies of the magnet 160 to rock owing to the fact that curved surfaces support the magnet), while a curved surface is utilized with one the other of the plates so as to achieve the above noted nonlinear force curve.

Figure 23A:
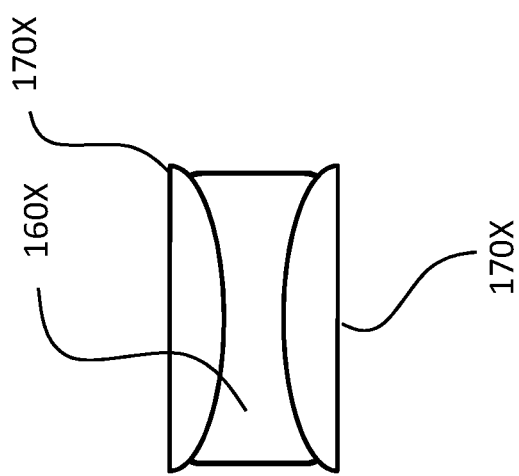

That said, in an alternate embodiment, the magnet is contoured to the curves. In this regard, FIG. 23A depicts magnet apparatus 160X, which has an upper surface and a lower surface that is contoured to the negative of the curved surfaces of the plates 170X. In an exemplary embodiment, magnet apparatus 160X is rotationally symmetric about the longitudinal axis thereof (i.e., it has bowl-like depressions on either side of the magnet apparatus). In an exemplary embodiment, this can have utilitarian value in that the contact between the magnet apparatus 160X and the plates 170X is always located at the outboard portions of the magnet 160X during rotation of the magnet 160X relative to the plates 170X (as opposed to possible embodiments of the embodiment of FIG. 22).

Figure 23B:
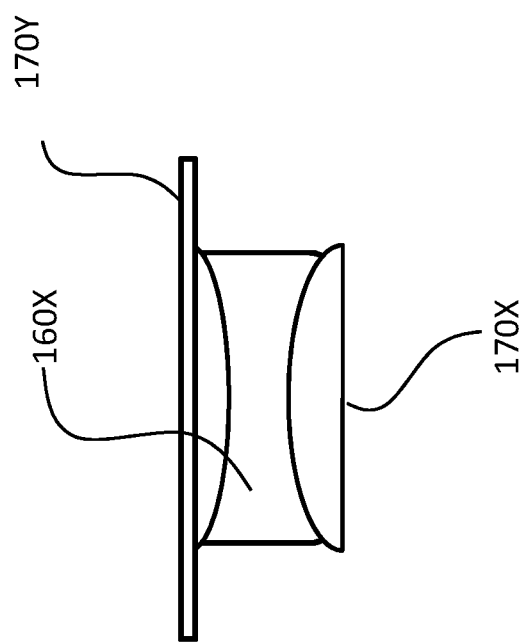

FIG. 23B depicts magnet apparatus 160 X in conjunction with plates 170Y and 170X. Plate 170Y includes the magnet apparatus contact surface corresponding to that of plate 170X, except with the additional feature that the plate 170Y extends further away from the longitudinal axis of the system than that of plate 170X. In an exemplary embodiment, this could have utilitarian value with respect to the fact that the bottom plate 170X is supported by the mastoid bone (in the example of a cochlear implant or other medical device having an inductance coil located thereabove), albeit through the body 199, while the top plate 170Y is not supported by any structure of the human body (or supported by soft tissue—skin, fat muscle). In this regard, the forces resulting from the application of the torque to the magnet apparatus are reacted against by bone on the bottom. Thus, the "footprint" of the bottom plate 170X can be smaller than that of the top plate 170Y, at least in some embodiments.

Figure 23C:
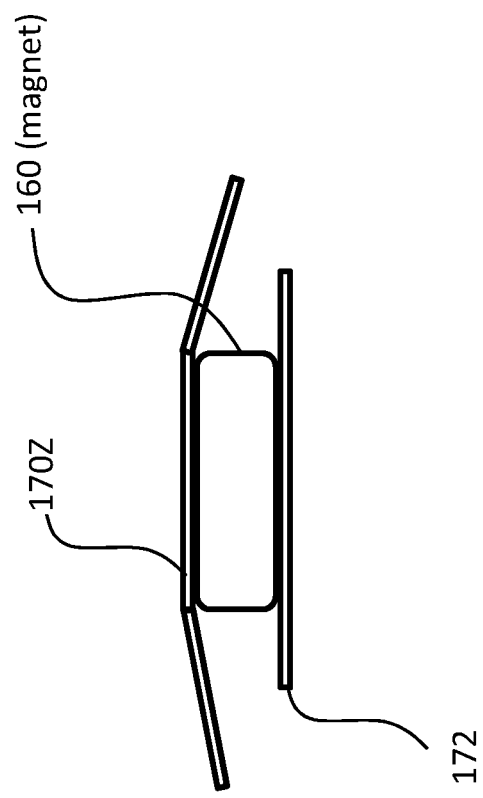

Corollary to the concept of FIG. 23B is seen in FIG. 23C, which uses flat parallel surfaces for the locations where the magnet apparatus will slide relative to the plates, but includes a plate 170Z that uses canted surfaces for the portions that do not come into contact with the magnet apparatus 160 during rotation of the magnet. These canted surfaces can be utilitarian in that the plate 170Z can be contoured to the outer geometry of the body of the implantable component 100, to the extent that the body of the implantable component 100 slopes downward from the center to the sides. By canting the plate 170Z as seen, a wider footprint can be achieved, while also permitting the implantable component to have a lower profile relative to that which would be the case if a perfectly flat plate having a similar footprint is utilized. Further as can be seen, the plate 170Z need not be symmetric about its longitudinal axis.

Figure 23D:
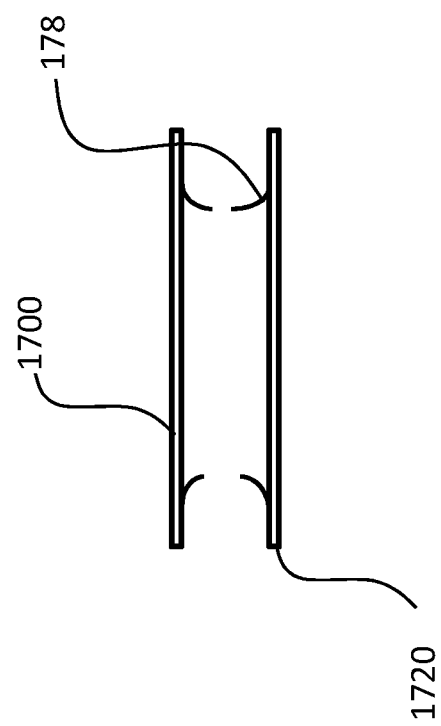
Figure 23E:
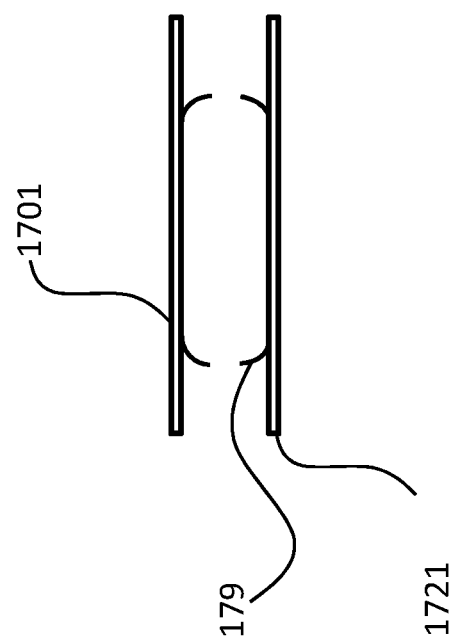

As noted above, not all of the surface of the plates is sliding surface. Accordingly, an exemplary embodiment, such as seen in FIG. 23D, includes plates 1700 and 1720 (the magnet apparatus 160 has been removed for clarity) that include bumpers 178 that align the magnet upon its return to the relaxed/no torque state after rotating due to exposure to the external magnetic field. The bumpers 178 can prevent the magnet from moving to a location beyond which is deemed permissible. FIG. 23E depicts an alternate embodiment, where plates 1701 and 1721 include tracks 179 that guide the magnet as it rotates, thus ensuring, or at least reducing the likelihood that the magnet will move to a location that is less utilitarian when subjected to the magnetic field and were after the magnetic field is removed (such functionality is also achievable in the embodiments utilizing the bumpers 178 in at least some embodiments). Note further that while the tracks and bumpers detailed herein are presented in terms of fixed components, these components can be configured to move with the magnet. Indeed, in exemplary embodiments, the magnet can have a system akin to a rack and pinion system that permits the magnet to move according to the teachings detailed herein while also preventing the magnet from moving outside the local geographic coordinates of the plate system.

It is noted that the exemplary embodiments presented in FIGS. 23A-23E, as with all embodiments herein, are presented in terms of concept. Variations from the specific disclosure herein can be practiced while achieving utilitarian value according the teachings detailed herein. To be clear, any device, system and/or method that can enable any of the teachings detailed herein and/or variations thereof to be practiced can be utilized at least some embodiments.

Any device, system and/or method of enabling the teachings detailed herein and/or variations thereof utilizing one or more structures (e.g., the plates) located in an elastomeric body can be utilized in at least some embodiments.

In view of the above, in an exemplary embodiment, there is an implantable medical device, such as any of those detailed herein and/or variations thereof, including a magnet, such as any of the magnets detailed herein and/or variations thereof, and a body encompassing the magnet, again such as any of the bodies detailed herein and/or variations thereof. In this exemplary embodiment, the implantable medical device includes structural components in the body configured to move away from one another upon initial rotation of the magnet relative to the body when the magnet is subjected to an externally generated magnetic field, thereby limiting rotation of the magnet beyond the initial rotation.

Also, in an exemplary embodiment, there is an implantable medical device, such as any of those detailed herein and/or variations thereof, including a magnet and a body encompassing the magnet. The implantable medical device includes structural components in the body configured to move away from one another due to torque applied to the magnet when the magnet is subjected to an externally generated magnetic field, thereby resisting rotation of the magnet at least beyond an initial rotation.

In an exemplary embodiment of these exemplary embodiments, the implantable medical device is configured to resist movement of the structural components away from one another. In an exemplary embodiment, the movement away of the structural components from one another tensions an elastomeric material making up at least a portion of the body, thereby limiting further movement of the structural components away from one another, which in turn limits further rotation of the magnet beyond any initial rotation.

Note further, in an exemplary embodiment, the structural components include surfaces facing one another in between which the magnet is located. The rotation of the magnet applies a force in a first direction against a first surface of one of the structural components and a force in a second direction against a second surface of one other of the structural components, thereby exerting forces on the components pushing the components away from one another, which force is at least partially resisted by the body, thereby limiting rotation of the magnet. Also, in an exemplary embodiment, the magnet is part of a magnet apparatus, and the implantable medical device is configured such that the magnet apparatus is slidable against the structural components, thereby encouraging rotation of the magnet relative to the structural components when the magnet is subjected to the externally generated magnetic field, relative to that which would exist with a configuration where the magnet apparatus was not slidable against the structural components.

Further, in an exemplary embodiment, the structural components comprise plates that sandwich the magnet, wherein torque applied to the magnet that imparts the rotation of the magnet imparts a camming action on the plates, thereby driving the plates away from one another, which camming action is counterbalanced when the plates have reached an equilibrium condition due to resistance to movement of the plates by the body.

As noted above, in at least some embodiments, there is utilitarian value with respect to enhancing the slidability of the magnet apparatus 160 relative to the plates. In this regard, in at least some embodiments, the surfaces facing the magnet apparatus/surfaces that contact the magnet apparatus are low friction surfaces. Alternatively and/or in addition to this, the surfaces of the magnet apparatus that contact the plates are also low friction surfaces. In an exemplary embodiment, a material that enhances slidability between the components can be utilized.

In at least some embodiments, the force profiles on the plates, or, more accurately, the change in the force profiles on the plates, due to movement of the plates away from one another, can be tuned by varying various properties of the plate-magnet-body combination. In an exemplary embodiment, the size of the plates (e.g., span) can be different depending on the desired change in the force profile. Alternatively and/or in addition to this, the elastomeric material making up the body can have different elastic moduluses. Alternatively and/or in addition to this, the stiffness of the plates can be changed. It is noted that in an exemplary embodiment, the stiffness can be varied by changing the thickness of the plate while using the same material, changing the material of the plate while maintaining the same thickness, or changing the material and thickness of the plate, all changes being relative to a given baseline (as is the case with all changes detailed herein). Still further, as detailed above, plates having different geometries can be utilized. With respect to the embodiment of FIG. 7D, the plate 170D will be less rigid at the outboard locations in a non-linear manner, owing to the fact that the thickness of the plates increases with distance towards the inboard location. That said, in an alternative embodiment, the structure of the plates can be such that the thickness of the plates thins with location closer to the inboard location.

Any arrangement of plates that can be utilized to implement the teachings detailed herein and/or variations thereof can be utilized in at least some embodiments.

With reference to FIG. 1B, as noted above, in an exemplary embodiment, the implantable component 100 includes a slit 180 configured to provide access through the exterior of the implantable component 100 to the location between the plates 170 and 172. Thus, according to an exemplary embodiment, there is an implantable medical device, such as a cochlear implant, or other medical device that utilizes a magnet, for whatever reason, comprising a magnet and a body encompassing the magnet, wherein the silicone body has a slit configured to enable passage of the magnet therethrough. Accordingly, an exemplary embodiment includes a side entry pocket for the magnet apparatus.

Figure 24:
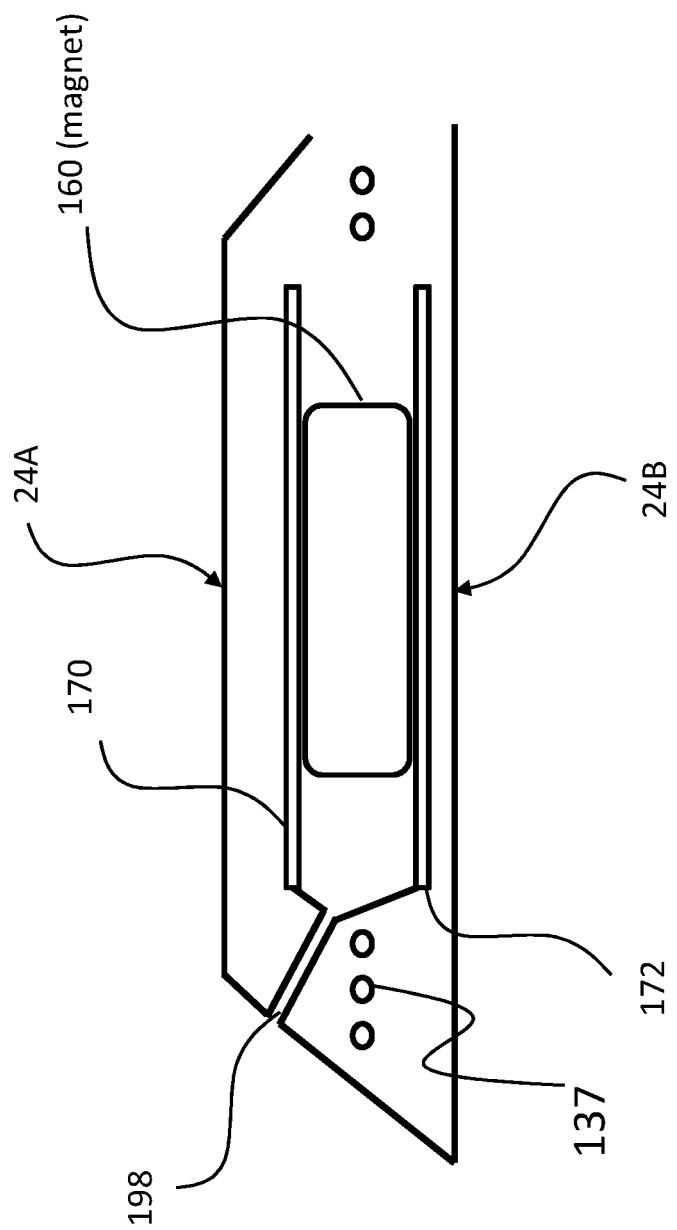
FIGS. 24-28C variously represent various exemplary conceptual schematics of various exemplary assemblies according to various exemplary embodiments.

More specifically, as can be seen in FIG. 24, which corresponds to an exploded view of a portion of the structure shown in FIG. 1C above, slit 198, which corresponds to slit 180 of FIG. 1B, in some embodiments, is located in a side wall of the housing made of elastomeric material 199. The slit 198 leads through the elastomeric material of the housing made thereof to a location between the plates 170 and 172. In an exemplary embodiment, in its relaxed state, the slit has a major axis that is at least about the width of the magnet apparatus 160, whereas the minor axis of the slit can be negligible, if not zero. That is, owing to the resiliency of the elastomeric material from which the housing is made, the slit 198 can be expanded to an expanded state so as to provide an opening of sufficient size to slide the magnet apparatus 160 into the housing and through the slit 198 to the location in between the plates.

Thus, with reference to FIG. 24, in an exemplary embodiment, the medical device includes a first surface and a second surface of an anti-rotation apparatus (e.g., plates 172 and 170), wherein the magnet is located between the first surface and the second surface, and wherein a path exists from ends of the surfaces to the slit 198 through which the magnet can travel to reach the slit 198.

It is noted that in some embodiments, the slit 198 is not provided in the implantable component 100 when implanted in the recipient. In an exemplary embodiment, the slit is provided in the implantable component at the time that the magnet is needed to be removed, via a surgery procedure. Accordingly, in an exemplary embodiment, there is a method of removing the magnet, which entails accessing the implantable component 100 while the implantable component is implanted in a recipient via a surgical procedure, optionally cutting into the body to form the slit 198, or opening the slit 198 if already present (and closed), removing the magnet apparatus 160, optionally temporarily closing the slit or otherwise sealing the slit, or replacing the magnet with a non magnetic blank (e.g., a dummy magnet) of similar outer dimensions, conducting an MRI method, reaccessing the implantable component 100, reopening the slit formed therein if the optional temporary closing thereof was executed, replacing the magnet apparatus 160, and closing the slit or otherwise sealing the slit (which closing/sealing can be a compost according to the teachings detailed below in at least some embodiments). Note further that in an exemplary embodiment, the implantable component 100 can include an embryonic slit. That is, the implantable component can include an area that is depressed or otherwise thin relative to other components, which area is proximate a path through the body to a location between the plates. Because the section is relatively thin, it will be relatively straightforward for the surgeon to cut through the thinned area to reach the path. Alternatively and/or in addition to this, the body can be marked or otherwise provided on the outside with a curve or a line (dye or with a raised or depressed area) indicating to the surgeon where he or she should cut to form the slit.

In an exemplary embodiment, the aforementioned features regarding the embryonic slits and/or markings can be molded into the silicone.

Figure 25:
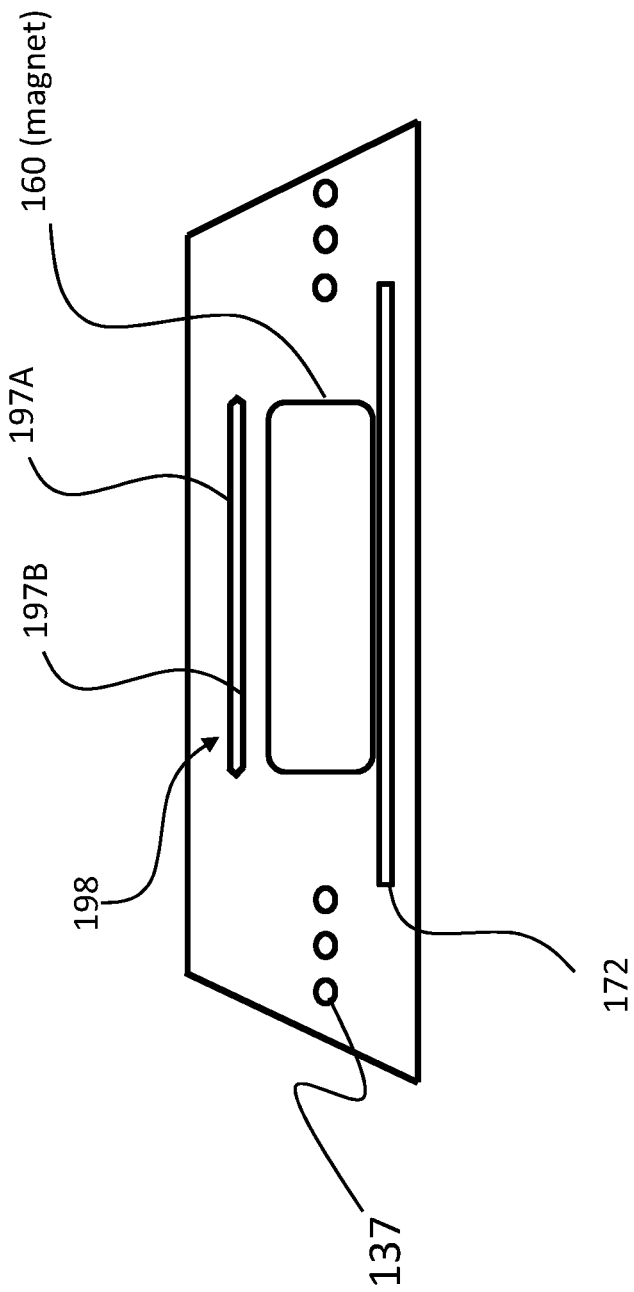

Now with reference to FIG. 25, which depicts a view looking from the right side of FIG. 24 down the longitudinal axis of the implantable component 100, with the top plate 198 removed for clarity, in an exemplary embodiment, the slit 198 includes two opposite surfaces 197A and 197B, the two opposite surfaces extending along the major axis of the slit (the axis parallel to the horizontal of FIG. 25). The two opposite surfaces are level in a plane extending normal to a thickness direction (the vertical direction of FIG. 25) of the magnet (when the slit is in the relaxed position). Further, the two opposite surfaces 197A and 197B are smooth, and the two opposite surfaces are in close proximity to one another (again, in the relaxed state). In an exemplary embodiment, the opposite surfaces 197A and 197B are in such close proximity to one another that they contact one another, again in the relaxed state. That said, in an alternative embodiment, the opposite surfaces are about 0.1, 0.2, 0.3, 0.4, 0.5, 0.6, 0.7, 0.8, 0.9 1.0, 1.1, 1.2, 1.3, 1.4, 1.5 mm or more away from each other in the relaxed state.

Figure 26:
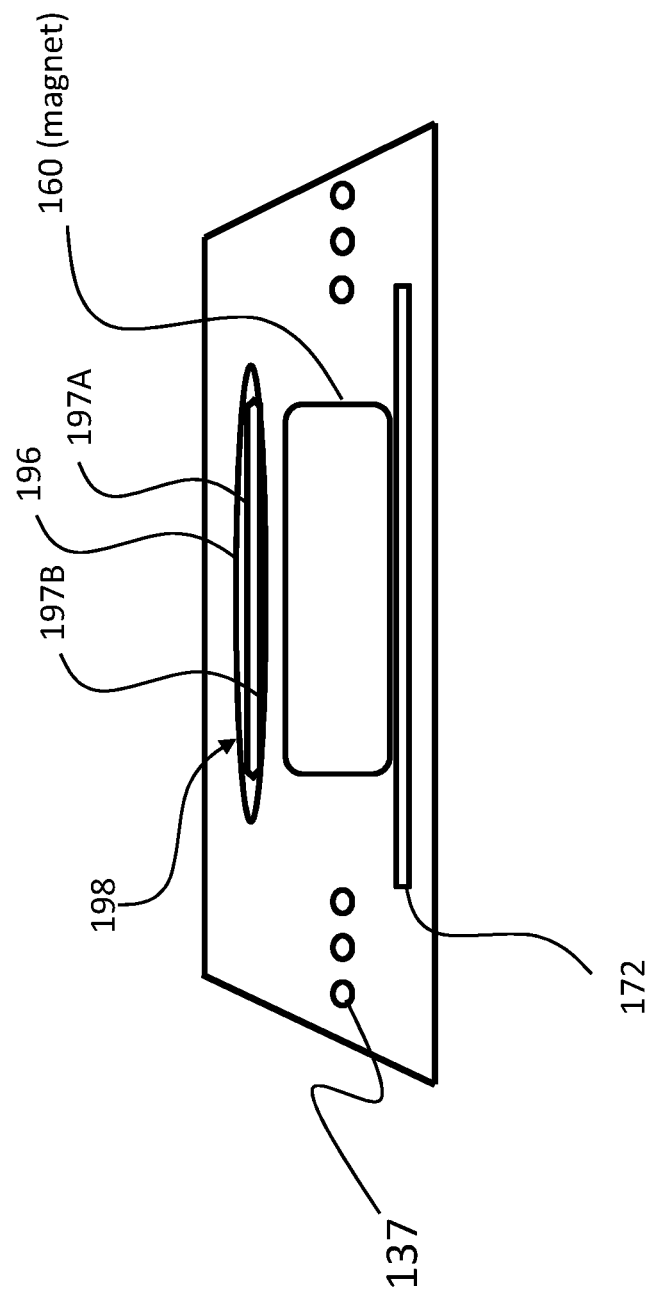
Figure 27A:
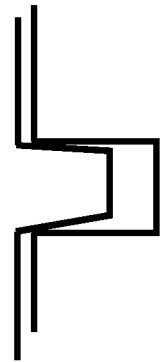
Figure 27B:
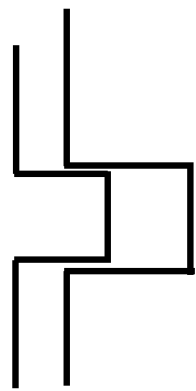
Figure 27C:
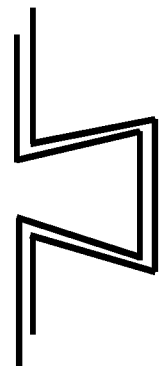

In an exemplary embodiment, the implantable component 100 is configured such that the two opposite surfaces 197A and 197B are urged towards each other, sometimes such that the surfaces contact one another. In an exemplary embodiment, this can be achieved via the general resilient/elastomeric nature of the material of the housing. Alternatively and/or in addition to this, this can be achieved via a spring embedded in the elastomeric body. In an exemplary embodiment, the implantable component 100 is configured such that the two opposite surfaces 197A and 197B are maintained in contact with each other. In an exemplary embodiment, this can be achieved via the general resilient/elastomeric nature of the material of the housing. Alternatively and/or in addition to this, this can be achieved via a spring 196 embedded in the elastomeric body, as conceptually depicted in FIG. 26, where the oval-shaped spring 196 has a memory that drives the spring 196 to have minor axis as short as possible (i.e., the upper and lower portions desire to head towards each other). Still further, by way of example only and not by way of limitation, this can be achieved via one or more sutures (applied after the magnet apparatus is inserted into the slit). Further, adhesives can be utilized to close the slit. Also, in an exemplary embodiment, a tongue and groove fit can be utilized, such as seen in FIGS. 27A, 27B and 27C, depicting a cross-sectional view of the slit 198 taken on a plane normal to the view of FIG. 25 in the vertical direction, where the top structure corresponds to the upper lip/surface of the slit, and the bottom structure corresponds to the lower lip/surface of the slit or vice versa. FIGS. 27B and 27C depict interference fits, with FIG. 27C depicting a dovetail fit.

In an exemplary embodiment, the slit 198 can be configured with a structure corresponding to a zip lock structure utilized in sandwich bags or sterile bags of the like.

Accordingly, in an exemplary embodiment, the slit is held at least one of closed or constrained against further opening using at least one of sutures, an interference fit between two opposite sides of the slit, or a spring embedded in the silicone body.

It is noted that any of these manners of closing or otherwise providing a force against the slit 198 from opening further can be combined with each other. Any device, system, and/or method that will enable the slit to be closed or otherwise provide a force against the slit 198 from opening further can be utilized in at least some embodiments. In this regard, in an exemplary embodiment, there is a device embedded or otherwise enclosed within the body that provides a compressive force on the surfaces of the slit.

Figure 28A:
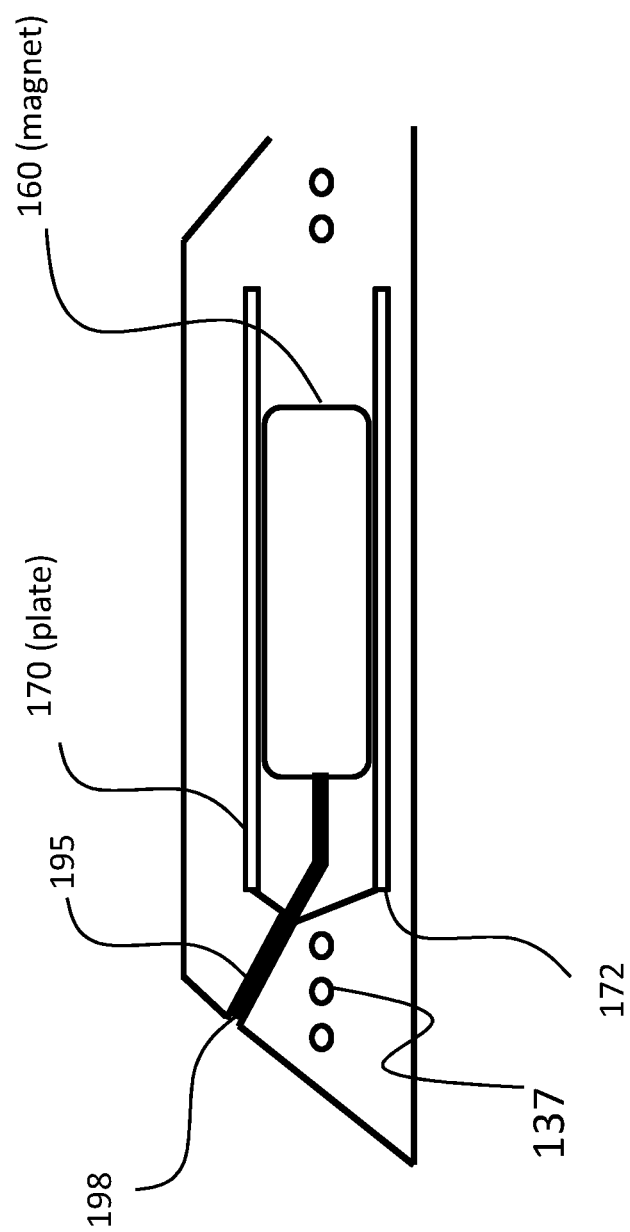

Note further that there are other manners in which the slit can be managed. Instead of or in addition to driving the surfaces of the slit towards each other or providing a force resisting opening of the slit, the slit can be plugged in a manner analogous to utilizing a cork to plug a bottle of wine or the like. In this regard, FIG. 28A duplicates FIG. 24, except depicting the plug 195 plugging the slit 198. As can be seen, the plug 195 is connected to the magnet apparatus 160. In this regard, the plug can have dual utilitarian value in that it can be utilized to aid in extracting and/or placing the magnet 160 between the plates. That said, in an alternative embodiment, plug 195 can be a separate component to the magnet. It is further noted that in an exemplary embodiment, the plug 195 is configured such that the magnet apparatus 160 can rotate according to the teachings detailed herein without adjusting or otherwise interfering with the location of the plug in the slit 198.

In view of the above, it can be seen that in an exemplary embodiment, no part of the magnet apparatus 160 forms an outer surface of the implantable component 100. In this regard, in an exemplary embodiment, this ensures that only the elastomeric material of the body is exposed. In exemplary embodiment, this can have utilitarian value in that less bacterial attachment will occur as bacterial attachment is lower with respect to silicone them with respect to titanium or other materials forming the outer boundary of the magnet apparatus 160. In an exemplary embodiment, utilitarian biofilm resistance can be achieved through maintaining the opposite surfaces of the slit 198 smooth, at the same level (no step), and in close proximity to one another.

Figure 28B:
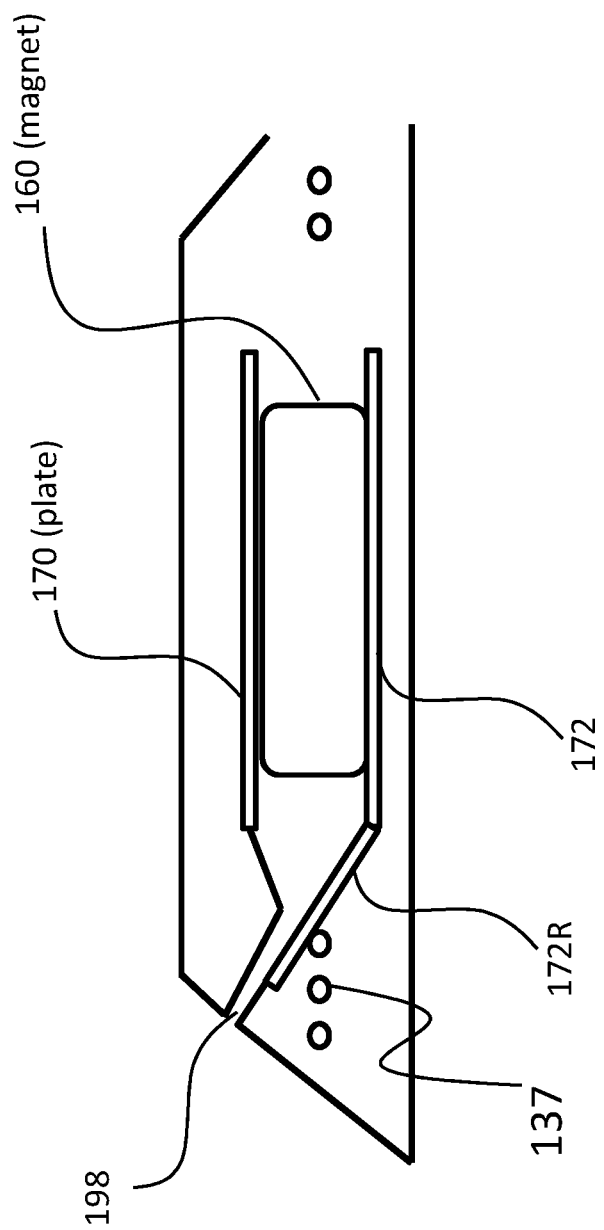

FIG. 28B presents another exemplary embodiment which has a ramp structure 172R, wherein the ramp structure 172R is configured to guide the magnet (and thus the magnet apparatus), during removal thereof from the body, towards the slit 198. In an exemplary embodiment, the ramp structure 172R is a separate component from the plate 172. In an exemplary embodiment, the two are linked by additional structure, or otherwise joined together by a suitable mechanical joining system (e.g., welding). Alternatively, the two are simply embedded or otherwise supported within the body as separate components. In an alternative embodiment, the ramp 172R is a portion of the bottom plate. That is, the bottom plate has a first portion that is configured to be parallel with the upper plate, and a portion that is angled, bent or otherwise canted relative to that first portion.

Figure 28C:
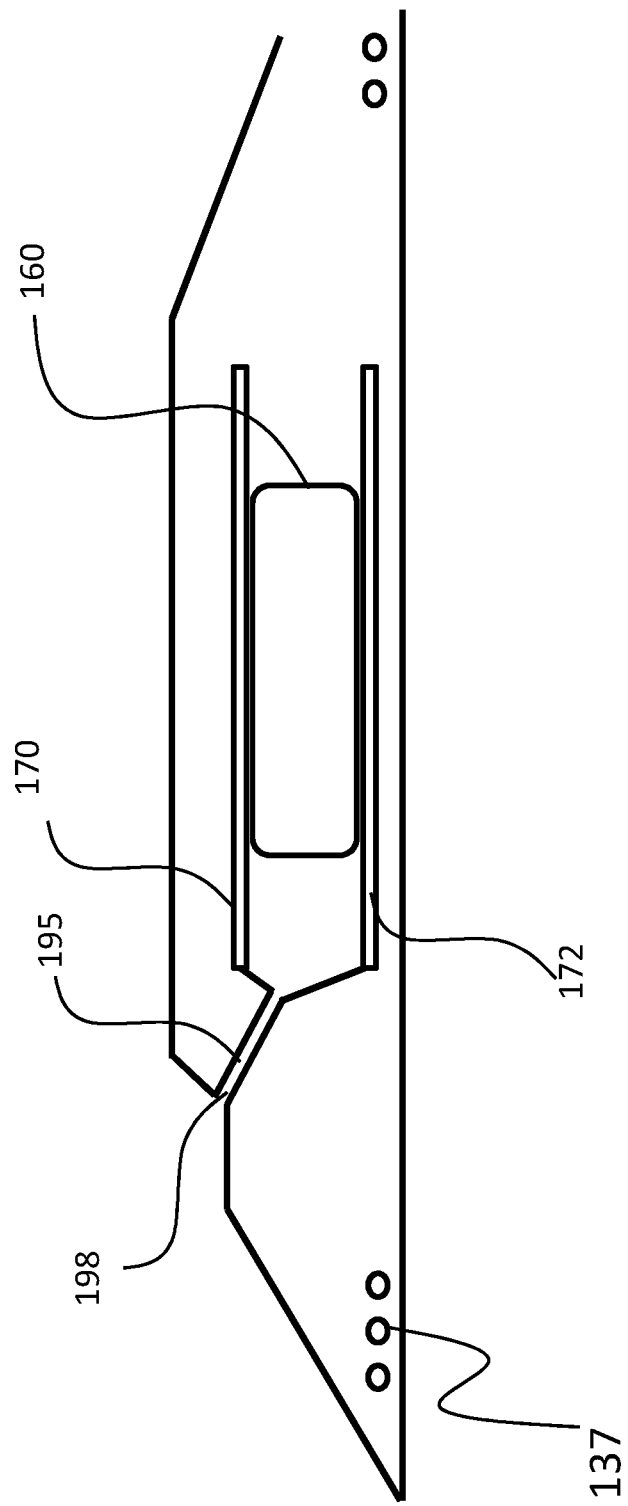

FIG. 28C presents a portion of the implantable component 100 according to a slightly alternate exemplary embodiment, with the view thereof generally corresponding to the view of FIG. 24, except that the coil 137 is located further away from the plates and the slit 198. In this regard, it can be seen that the body portion extends further away from the plates than in the exemplary embodiment of FIG. 24, and thus the coil 137 also is located further away from the plates and the slit 198 than an exemplary embodiment of FIG. 24.

Figure 29:
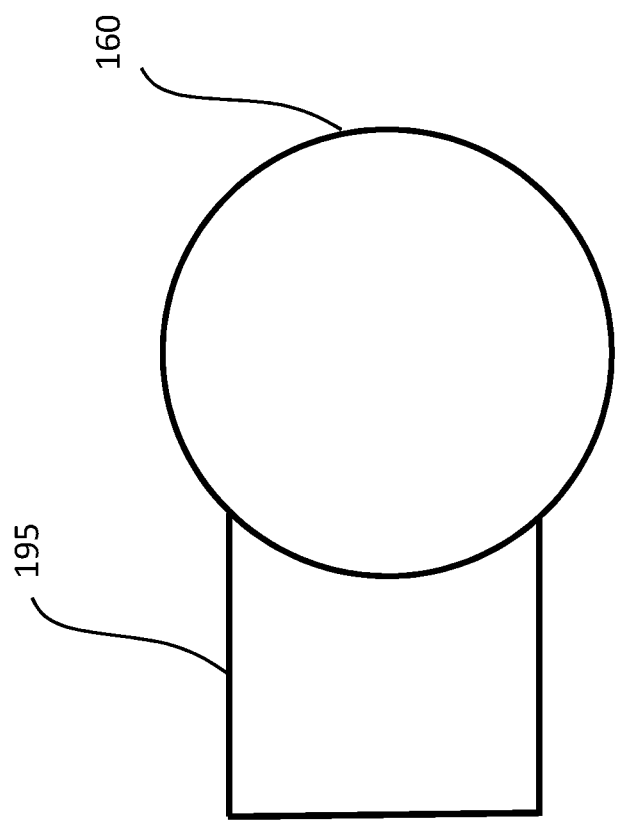
FIG. 29 represents an exemplary embodiment of a magnet apparatus according to an exemplary embodiment.

FIG. 29 depicts a top view of an exemplary plug-magnet apparatus combination. In this exemplary embodiment, it can be seen that the plug has a relative diameter that is smaller than the maximum diameter of the magnet apparatus. This can have utilitarian value with respect to slits 198 that have a major axis that is smaller than the maximum diameter of the plug. That said, in an alternate embodiment, the relative diameter can be larger than the maximum diameter of the magnet apparatus or can be the same as the maximum diameter of the magnet apparatus.

Accordingly, in an exemplary embodiment of the embodiments utilizing the slits detailed herein and/or variations thereof, the magnet is part of a magnet apparatus, the magnet apparatus including a first portion (e.g., the plug 195), wherein the first portion is located in the slit 198, resisting further closure of the slit, thereby creating a seal between the slit 198 and the first portion 195. Corollary to this is that in at least some embodiments, the plug 195 is configured to expand the slit, at least slightly, beyond the size of the slit in a relaxed position, thereby establishing the seal. It is further noted that in at least some embodiments, any of the aforementioned features utilized with the slits detailed herein can be utilized to seal the slit 198. Note that by seal, it is not meant that a hermetic seal is established. That said, in an alternative embodiment, a hermetic seal can be established according to some implementations of the teachings detailed herein, if not with silicone, with some other material (or a composite material can be utilized, where the slit is formed by a material that can form a hermetic seal, and that material is bonded or otherwise attached to the silicone or other material). That said, the slit can be configured to prevent "larger" matter from entering, an/or can establish a seal that is concomitant with any permeability features of the body in general (e.g., the overall body effectively performs as if the body does not have a slit). It is further noted that while the ends of the slits are depicted as tapering towards each other from the respective upper and lower surfaces thereof, in an alternative embodiment, the ends of the slit can encompass a slightly wider circular area so as to relieve stress and/or avoid "tearing" of the elastomeric material of the housing.

FIGS. 24 and 25 depict the slit 198 being located in a sidewall of the body of the implantable component 100, as opposed to the top wall or the bottom wall (the walls configured to be located parallel to the skin, and in the case of a cochlear implant, the mastoid bone of the recipient when the medical devices is implanted). More generally, the outer dimensions of the body 199 have a length (the direction along the longitudinal axis of the body (the horizontal direction of FIGS. 1B and 1C)), a width (the vertical direction of FIG. 1B), and a height (the thickness/the vertical direction of FIG. 1C), wherein the height is measured through the magnet, wherein the height is the smallest dimension, and wherein the slit 198 is located between points on the two surfaces establishing the height dimension (e.g., points 24A and 24B, as shown in FIG. 24). Still further, as can be seen from the FIGS., the slit 198 is configured to enable ingress and egress of the magnet 160 in a direction having a major component in a Cartesian coordinate system in at least one of the X or Z direction, wherein the Y direction is normal to a surface of the body configured to lie against a mastoid bone of a recipient of the implantable medical device (the surface of point 24B of FIG. 24). In this regard, as can be seen from FIG. 24, for magnet 160 to be removed, it must extend a greater distance in the X direction (the horizontal of FIG. 24) than in the Y direction (the vertical of FIG. 24), and thus the direction of Y is a minor component of the movement of the magnet 160 during ingress and egress (as it is smaller than the X component—the Z component is zero, as the Z component extends out of the page of FIG. 24, but in an embodiment where the slits 198 is located on the lateral sides of the body (as opposed to the longitudinal side), or in between, the Z component would be non-zero).

Note further that in the embodiment of FIGS. 24 and 25, the medical device includes an electromagnetic communication coil 137 extending about the magnet 160. The medical device includes a functional component (stimulator 122) communicatively linked to the communication coil 137, the functional component 122 and the slit 198 being located opposite one another relative to the magnet 160. This is opposed to a scenario where the slit was located at point 24A or 24B.

It is noted that embodiments include methods of utilizing the teachings detailed herein and/or variations. In this regard, it is noted that any disclosure of any device or system corresponds to a disclosure of a method of using and a method of making that device and/or system. Further, any disclosure of any method detailed herein also corresponds to a disclosure of a device for executing the method and/or a system for executing the method. In this regard, an exemplary method will now be described, where, as just noted, embodiments include a device configured to execute any or all of the method actions that follow.

Figure 30:
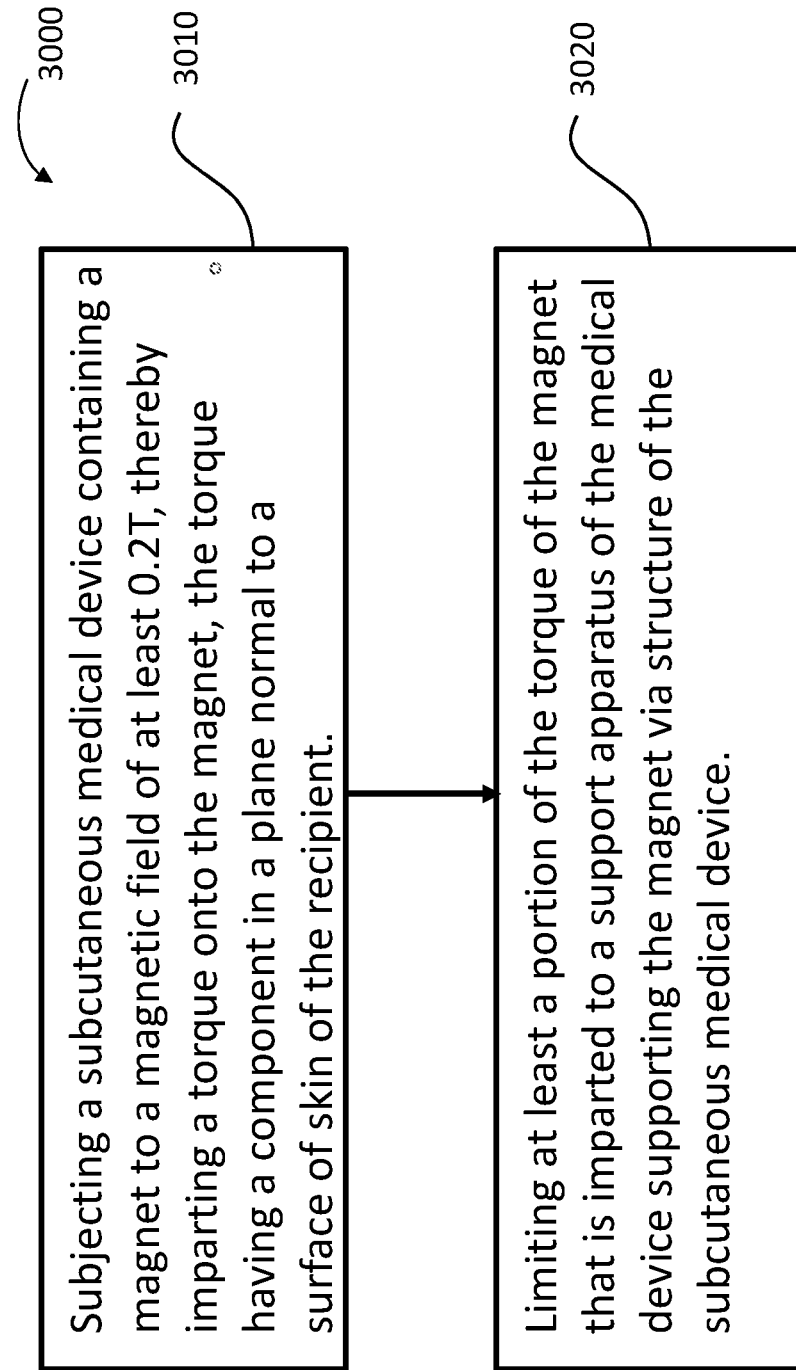
FIG. 30 represents an exemplary flowchart according to an exemplary method of an exemplary embodiment.

Referring now to FIG. 30, there is an exemplary flowchart 3000, which corresponds to an exemplary method. Flowchart 3000 includes method action 3010, which entails subjecting a subcutaneous medical device containing a magnet, such as any of the medical devices detailed herein and/or variations thereof, to a magnetic field of at least 0.2 T, such as that resulting from an MRI machine, thereby imparting a torque onto the magnet, the torque having a component in a plane normal to a surface of skin of the recipient. It is noted that the at least 0.2 Tesla magnetic field is a threshold value. Exemplary embodiments can entail subjecting the magnet to a magnetic field of at least 0.2 T, 0.5 T, 1.0 T, 1.5 T, 2.0 T, 2.5 T, 3 T or 4 T or 7 T or more. It is further noted that with respect to the component of the torque, this means that if the torque is divided up into planes lying on the Cartesian coordinate system, a component of the torque will lie on the plane that is normal to the skin of the recipient (e.g., of the X and Z axis are located on the tangent surfaces of the skin, the Y axis is normal to the surface of the skin). There may be a component of the torque imparted onto other planes, but there will be at least a torque component located on the aforementioned plane. An exemplary embodiment, this is the major torque component. That is, of all of the torque components, the component lying on this plane will be the largest.

Method 3000 further includes method action 3020, which entails limiting and/or opposing at least a portion of the torque of the magnet that is imparted to a support apparatus (e.g., the plates) of the medical device supporting the magnet (either directly or indirectly) via structure of the subcutaneous medical device. In an exemplary embodiment, the elimination of all torque that is imparted into the support apparatus can meet this method action, providing that such an arrangement can be manufactured in a utilitarian manner. In an exemplary embodiment, the limitation of the amount of torque that is applied to the magnet that is imparted into the support apparatus can be limited and/or opposed to/by about 35%, 40%, 45%, 50%, 55%, 60%, 65%, 70%, 75%, 80%, 85%, 90%, 95% and/or 100% or an value or range of values in between in about 1% increments of the torque applied to the magnet (e.g., at 50%, half the torque applied to the magnet is imparted into the support apparatus, at 10%, only $1/10^{th}$ of the torque applied to the magnet is imparted into the support apparatus, etc.).

In an exemplary embodiment, the action of limiting at least a portion of the torque of the magnet that is imparted to support apparatus of the medical device entails permitting the magnet to rotate at least about 5° in the plane relative to a position of the magnet in the absence of the external magnetic field. In an exemplary embodiment, this entails permitting the magnet to rotate at least about 10°, 15°, 20°, 25°, and/or about 30°, or more, or any value or range of values therebetween in about 1° increments. Still further, in an alternate embedment, this entails preventing the magnet from rotating any more than at least about 5°, about 10°, about 15°, about 20°, about 25°, and/or about 30°, and/or about 35° or any value or range of values therebetween in about 1° increments.

In an exemplary embodiment, the action of limiting at least a portion of the torque of the magnet that is imparted to the support apparatus of the medical device entails permitting the magnet to slide relative to the support apparatus such that the support apparatus expands from a contracted state (e.g., the plates 170 and 172 move away from one another), thereby transferring energy from the torque into a body of the implanted medical device (e.g., the body made from elastomeric material 199 as detailed above) which transferred energy is absorbed by the body. This as opposed to a scenario where the torque is transferred into the body, and the body transfers the torque into the tissue of the recipient, where the energy transferred into the tissue is absorbed by the tissue. That said, it is noted that owing to the expansion of the support structure, and thus the expansion of the body, a force will be imparted onto the tissue of the recipient. However, the energy absorbed by the body of the implanted medical device can be more than the energy transferred to the skin of the recipient as a result of the torque. In an exemplary embodiment, over 50% of the energy that is transferred from the magnet is absorbed by the body of the implanted device, and thus less than 50% of the energy that is transferred from the magnet is available to be absorbed by the tissue/skin of the recipient. In an exemplary embodiment, over about 55%, 60%, 65%, 70%, 75%, 80%, 85%, 90%, 95%, or more of the energy that is transferred from and/or into the magnet is absorbed by the body of the implanted device.

In an exemplary embodiment, the magnet is permitted to partially rotate so that the poles of the magnet are more aligned with the external magnetic field, while not necessarily being completely aligned, so as to reduce the torque on the implant resulting from the interaction of the external magnetic field with the magnetic field of the permanent magnet, relative to that which would be the case if the magnet was restrained from rotating relative to the body of the implant. The amount of rotation that is permitted is within the boundaries of the design of the implant so as to substantially ensure that upon the removal of the external magnetic field, the magnet returns to its at rest position, and the implant is not permanently damaged.

Corollary to the above, it is noted that in an exemplary embodiment, method 3000 further includes limiting at least a portion of the torque of the magnet that is imparted into tissue of the recipient of the medical device via structure of the subcutaneous medical device. In an exemplary embodiment, about 50%, 55%, 60%, 65%, 70%, 75%, 80%, 85%, 90%, 95%, or more of the energy that is transferred into the magnet is prevented from being transferred to tissue of the recipient. Thus, as will be understood from the aforementioned examples, in at least some embodiments, the methods according to the teachings detailed herein include limiting effectively all of the torque of the magnet that is imparted into tissue of the recipient of the medical device via structure of the subcutaneous medical device.

It is further noted that in at least some of these exemplary methods, the magnet is restrained from rotating more than a quarter revolution (90°) relative to the position of the magnet and the absence of the magnetic field, and in some embodiments the magnet is restrained from rotating more than an eighth of a revolution (45°) relative to the position of the magnet absence of the magnetic field. Still further, in some embodiments the magnet is restrained from rotating more than about 10°, 15°, 20°, 25°, 30°, 35°, or 40° relative to the position of the magnet absence of the magnetic field.

In view of the above, in at least some exemplary embodiments, implantable component is configured such that the plates generally remain parallel to one another as the magnet apparatus rotates when exposed to the magnetic field(s) having the strengths detailed herein, at least with respect to some of those magnetic fields. In an exemplary embodiment, the plates remain parallel to one another over one or more or all or any of the aforementioned rotational angles detailed herein of the magnet apparatus. In an exemplary embodiment, the plates remain parallel to one another over one or more or all or any of the aforementioned separation distances (D1 to D2) and/or changes in the separation distances (D2–D1) detailed herein.

In at least some exemplary embodiments, the implantable component is configured to convert the rotational motion of the magnet apparatus to the translational movement of the plates detailed herein. In an exemplary embodiment, the implantable component is configured to disperse or otherwise diffuse the energy across a greater area of the resilient material of the body than that which would be the case if the rotation of the magnet apparatus was directly resisted by the elastomeric body (e.g., in a scenario where the magnet support structure rotated in a one-to-one relationship with the magnet (with respect to at least one plane of rotation).) That is, by way of example only and not by way of limitation, a comparison between the teachings detailed herein can be made to a scenario where the plates 170 and 172 are rigidly attached to the magnet apparatus/magnet such that any rotation of the magnet also corresponds to an equal rotation of the plates, at least with respect to at least one of plane of rotation. In this regard, in exemplary embodiments, instead of transferring the torque imparted onto the plates by way of the rotation of the magnet (which causes rotation of the plates by an amount that is limited by the resistance to the rotation of the plates by the body), as would be the case in the aforementioned control scenario, the torque is converted into a linear movement of the plates away from one another, where the energy of the torque is dissipated into the elastomeric body via the stretching of the elastomeric body in a linear direction.

In an exemplary embodiment, the teachings detailed herein and/or variations thereof avoid localized loading, or at least reduce the localized, which can occur with a structure having the same outer dimensions as the plates (albeit when rigidly connected to the magnet apparatus/magnet, at least such that any rotation of the magnet results in rotation of the plates at least in one plane of rotation)—the control structure. In this regard, in this exemplary control scenario where the plates are rigidly linked to the magnet apparatus, the energy/force resisting rotation of the magnet apparatus (and thus the plates) is concentrated at the edges of the plates. (The adjacent parts of the elastomeric body remained relatively unloaded relative to the portions of the elastomeric body near the upper/lower edges of the plates.) Conversely, because in at least some exemplary embodiments, the plates do not rotate, or at least rotate less than they would in the aforementioned scenario where the plates are rigidly attached to the magnet apparatus, the energy/force resisting movement of the plates is diffused over a larger area of the plates (or at least any concentrations of energy are located further away from the edges of the plates or otherwise located over a greater area). (The adjacent parts of the elastomeric body relative to the portions of the elastomeric body near the upper/lower edges of the plates are more loaded as compared to the aforementioned example.)

Figure 31:
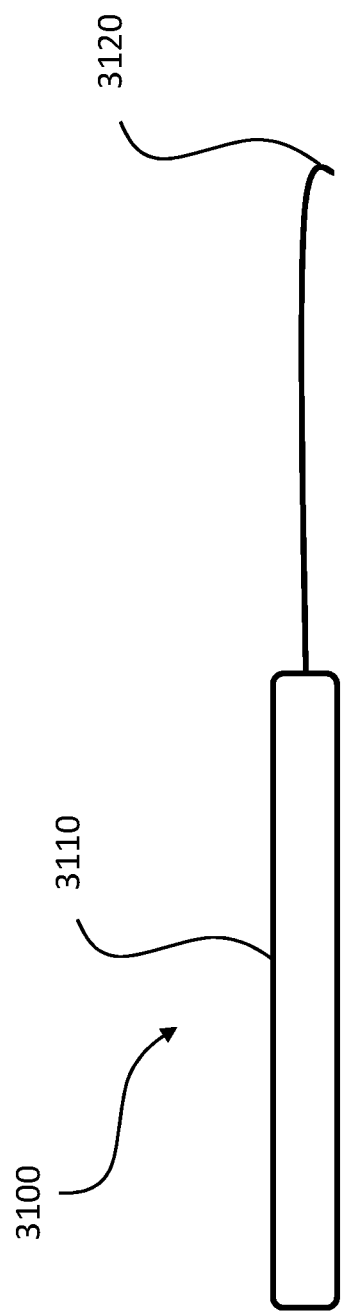
FIG. 31 represents an exemplary tool according to an exemplary embodiment utilized in some exemplary methods according to the teachings detailed herein.
Figure 34:
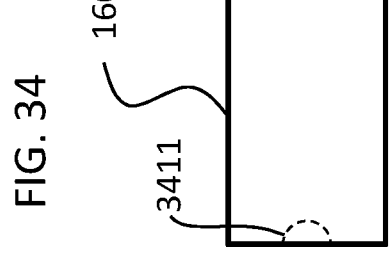
FIG. 34 represents an exemplary magnet apparatus according to an exemplary embodiment.
Figure 32:
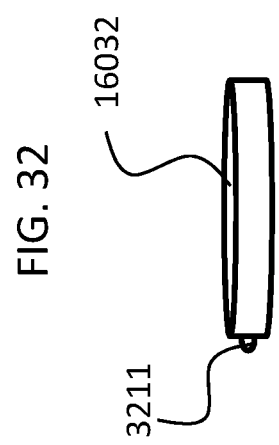
FIG. 32 represents an exemplary magnet apparatus according to an exemplary embodiment.
Figure 33:
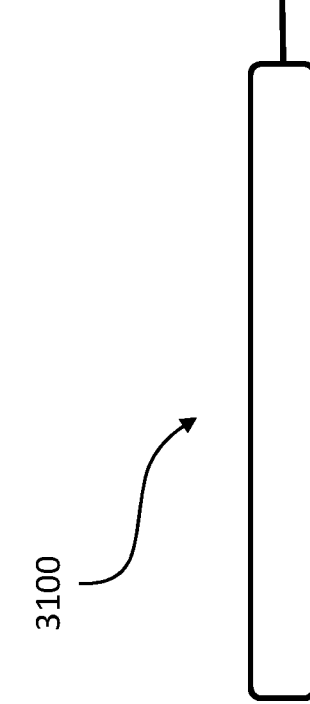
FIG. 33 depicts use of the tool of FIG. 31 with the exemplary magnet apparatus of FIG. 32 according to an exemplary embodiment.

FIG. 31 presents an exemplary tool usable in an exemplary embodiment to remove and/or install exemplary magnet apparatuses in an exemplary embodiment. FIG. 31 depicts a tool 3100, which includes a handle 3110, and a hook 3120 extending therefrom. In an exemplary embodiment, the hook 3120 is sized and dimensioned to fit between the slit noted above and extend therethrough through the path to reach the magnet apparatus located between the aforementioned plates/to push the magnet down the path to the location between the aforementioned plates. Corollary to this is that FIG. 32 depicts an exemplary magnet apparatus 16032, including a handle 3211 sized and dimensioned to receive the hook of the tool 3100, as is depicted by way of example only and not by way of limitation in FIG. 33. In at least some embodiments, as noted above, the tool 3100 can be used to push the magnet 16032 through the path to the location between the plates. FIG. 34 depicts an alternate embodiment of a magnet apparatus 16034, where the magnet apparatus includes a rectangular plate magnet instead of a circular magnet simply in the interests of conveying the fact that a wide arrangement of magnets and magnet apparatuses can be utilized in at least some embodiments. As can be seen, the apparatus 16034 includes a looped path 3411 in the magnet that is sized and dimensioned to receive the hook of the tool 3100. While the openings of the looped path 3411, and the looped path in general, is depicted lying in the plane of FIG. 34, in an alternate embodiment, the path can extend through the plane of FIG. 34 (e.g., into the page). Any arrangement of a handle device that can enable the teachings detailed herein and or variations thereof to be practice can be utilized at least some exemplary embodiments.

Figure 35:
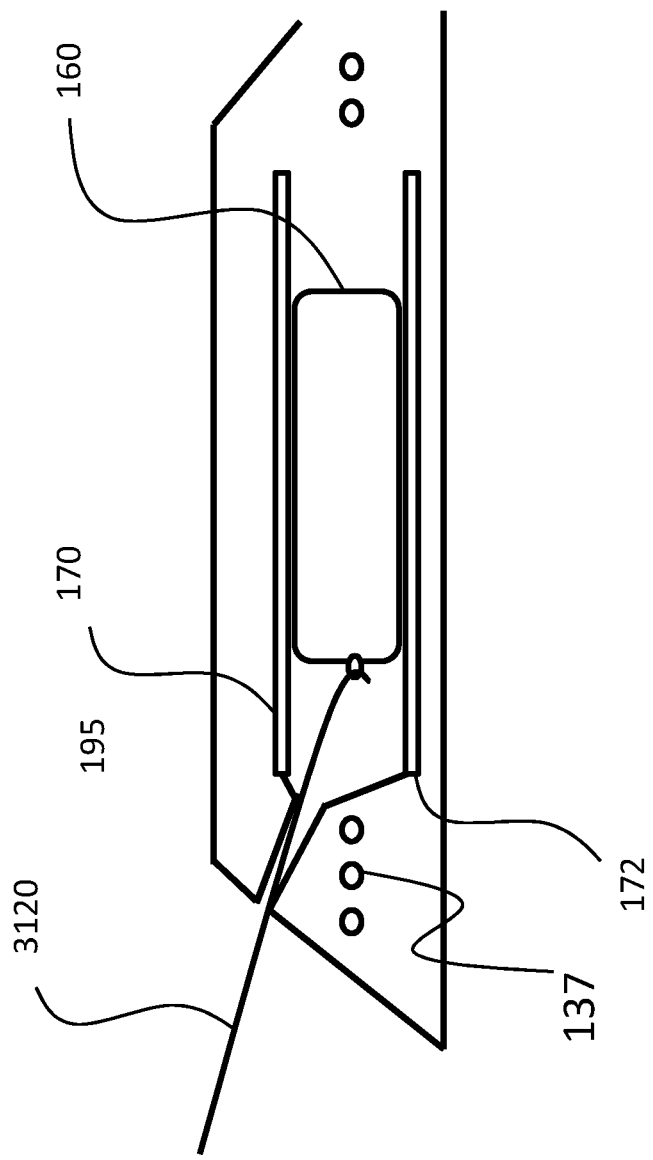
FIG. 35 represents an exemplary use of the tool of FIG. 31 with the embodiment of FIG. 25.

FIG. 35 presents an exemplary scenario of utilizing the tool 3100 to position and/or remove the magnet 160. As can be seen, the hook 3120 extends through the path leading from the slit to the magnet 160. Also as can be seen, the elastomeric material of the body 198 can be seen to be deformed at the location proximate the upper plate 170 by the hook 3120, thus giving an example of how the elastomeric material of the body can accommodate the insertion and/or removal process of the magnet.

It is noted that any method detailed herein also corresponds to a disclosure of a device and/or system configured to execute one or more or all of the method actions detailed herein. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system.

It is noted that in at least some exemplary embodiments, any feature disclosed herein can be utilized in combination with any other feature disclosed herein unless otherwise specified. Accordingly, exemplary embodiments include a medical device including one or more or all of the teachings detailed herein, in any combination.

Note that exemplary embodiments include components detailed herein and in the figures that are rotationally symmetric about an axis thereof (e.g., the magnet apparatus 160, the plates, etc.). Accordingly, any disclosure herein corresponds to a disclosure in an alternate embodiment of a rotationally symmetric component about an axis thereof. Moreover, the exemplary embodiments include components detailed in the figures that have cross-sections that are constant in and out of the plane of the figure. Thus, the magnet apparatus 160 can correspond to a bar or box magnet apparatus, etc.).

While various embodiments of the present invention have been described above, it should be understood that they have been presented by way of example only, and not limitation. It will be apparent to persons skilled in the relevant art that various changes in form and detail can be made therein without departing from the spirit and scope of the invention.

What is claimed is:

1. A hearing prosthesis, comprising:
an external device including a magnet; and
an implantable device including a disk magnet, wherein
the implantable device is configured such that the disk magnet revolves in a first plane normal to a longitudinal axis of the disk magnet and such that the disk magnet rotates in a second plane that is parallel to the longitudinal axis, and
the hearing prosthesis is configured to utilize the magnet of the external device and the disk magnet to retain the external device to a recipient of the hearing prosthesis.

2. The hearing prosthesis of claim 1, further comprising:
a container containing the disk magnet, wherein
the disk magnet includes an axis that is normal to the longitudinal axis of the disk magnet, wherein the second plane is normal to the axis that is normal to the longitudinal axis of the disk magnet, and the axis of the disk magnet that is normal to the longitudinal axis of the disk magnet is normal to a longitudinal axis of an interior of the container.

3. The hearing prosthesis of claim 1, further comprising:
a container containing the disk magnet, wherein
the disk magnet includes an axis that is normal to the longitudinal axis of the disk magnet, wherein the second plane is normal to the axis that is normal to the longitudinal axis of the disk magnet, and
the rotation in the second plane also corresponds to rotation relative to the container, and the revolving in the first plane also corresponds to revolving relative to the container, and
the implantable device is configured so that the rotation relative to the container in the second plane is limited and the revolving in the first plane is unlimited.

4. The hearing prosthesis of claim 1, wherein:
the disk magnet includes a North-South magnetic axis that extends diametrically.

5. The hearing prosthesis of claim 1, further comprising:
a container containing the disk magnet, wherein
the rotation of the disk magnet in the second plane is limited by interior walls of the container.

6. The hearing prosthesis of claim 5, wherein:
the limited rotation is due to contact of lateral portions of the disk magnet with portions of the interior walls of the container.

7. The hearing prosthesis of claim 6, wherein:
the disk magnet is free to revolve within the container in the first plane even when the disk magnet is limited by the interior walls of the container from rotating in the second plane.

8. The hearing prosthesis of claim 5, wherein:
the disk magnet is configured to revolve in the container in the first plane even when the disk magnet is limited by the interior walls of the container from rotating in the second plane.

9. The hearing prosthesis of claim 1, wherein:
the implantable device includes a stimulator unit and an electrode assembly including an array of electrodes; and
the hearing prosthesis includes a sound processor and a microphone.

10. The hearing prosthesis of claim 1, wherein:
the external device includes a wire antenna coil; and
the implantable device includes a wire antenna coil.

11. The hearing prosthesis of claim 1, further comprising:
a container containing the disk magnet; and
a lubricant in the container that reduces friction between the disk magnet and an inner surface of the container.

12. The hearing prosthesis of claim 1, wherein:
the implantable device is configured so that the rotation of the disk magnet is partially around an axis that is normal to the longitudinal axis, wherein the rotation can be at least 10 degrees and the revolving of the disk magnet is unlimited around the longitudinal axis.

13. A hearing prosthesis, comprising:
an external device including a first magnet; and
an implantable device including a second magnet with a flat surface configured to face the first magnet, wherein
the implantable device is configured such that the second magnet revolves around a longitudinal axis of the second magnet and such that the second magnet rotates partially around an axis that is normal to the longitudinal axis, and the hearing prosthesis is configured to utilize the first magnet and the second magnet to retain the external device to a recipient of the hearing prosthesis.

14. The hearing prosthesis of claim 13, wherein:
the implantable device further comprises a magnet apparatus, the magnet apparatus including the second magnet and a container containing the second magnet, and
the magnet apparatus is configured such that the second magnet revolves relative to the container around the longitudinal axis of the second magnet and such that rotation of the second magnet partially around the axis that is normal to the longitudinal axis is limited by inner walls of the container.

15. The hearing prosthesis of claim 14, wherein:
the implantable device includes an inductance coil; and
the longitudinal axis of the second magnet rocks relative to the inductance coil when the second magnet rotates; and
when the implantable device is implanted in a recipient above a skull of the recipient, the longitudinal axis extends through the skull.

16. The hearing prosthesis of claim 14, wherein:
the second magnet has a compound top face and a compound bottom face opposite the top face, wherein the bottom face faces bone of a recipient of the hearing prosthesis when the implantable device is implanted in the recipient.

17. The hearing prosthesis of claim 16, wherein:
the second magnet has a circular outer profile with respect to a cross-section lying on a plane normal to the longitudinal axis.

18. The hearing prosthesis of claim 14, wherein:
the implantable device includes a stimulator unit and an electrode assembly including an array of electrodes.

19. The hearing prosthesis of claim 13, wherein:
the implantable device further comprises a magnet apparatus, the magnet apparatus including the second magnet and a container containing the second magnet, and
the magnet apparatus is configured such that the second magnet revolves relative to the container around the longitudinal axis of the second magnet and such that the second magnet rotates relative to the container partially around the axis that is normal to the longitudinal axis.

20. The hearing prosthesis of claim 19, wherein the axis that is normal to the longitudinal axis is parallel to a width of an interior of the container, the width being the largest dimension of the interior of the container.

21. The hearing prosthesis of claim 19, wherein:
with respect to a cross-section of the second magnet lying on a plane lying on and perpendicular to the longitudinal axis, the cross-section of the second magnet is circular.

22. The hearing prosthesis of claim 21, wherein:
with respect to a second cross-section of the second magnet lying on a plane lying on and parallel to the longitudinal axis, the second cross-section of the second magnet has a curved portion.

23. The hearing prosthesis of claim 19, wherein:
the external device includes a wire antenna coil; and
the implantable device includes a wire antenna coil.

24. The hearing prosthesis of claim 19, wherein:
the implantable device includes a stimulator unit and an electrode assembly including an array of electrodes; and
the hearing prosthesis includes a sound processor and a microphone.

25. The hearing prosthesis of claim 19, wherein:
the implantable device is configured so that the flat surface remains facing the first magnet when rotated relative to the container by a maximum amount of rotation permitted by the container.

26. The hearing prosthesis of claim 13, wherein:
the second magnet has a north-south axis offset from the longitudinal axis.

27. The hearing prosthesis of claim 26, wherein:
the second magnet includes a north-south axis aligned with a lateral axis of the second magnet.

28. The hearing prosthesis of claim 13, wherein:
the external device includes a wire antenna coil;
the implantable device includes a wire antenna coil; and
the hearing prosthesis includes a sound processor and a microphone.

29. The hearing prosthesis of claim 13, wherein:
the second magnet is polarized to have a north pole and a south pole positioned away from the longitudinal axis.

30. The hearing prosthesis of claim 13, wherein:
the flat surface is parallel with a flat surface of the first magnet when there is zero rotation of the second magnet partially around the axis that is normal to the longitudinal axis.

* * * * *